US008900820B2

(12) United States Patent
Muraca

(10) Patent No.: US 8,900,820 B2
(45) Date of Patent: *Dec. 2, 2014

(54) GENE AND PROTEIN EXPRESSION PROFILES ASSOCIATED WITH THE THERAPEUTIC EFFICACY OF EGFR-TK INHIBITORS

(75) Inventor: Patrick J. Muraca, Pittsfield, MA (US)

(73) Assignee: Nuclea Biotechnologies, Inc., Pittsfield, MA (US)

( * ) Notice: Subject to any disclaimer, the term of this patent is extended or adjusted under 35 U.S.C. 154(b) by 364 days.

This patent is subject to a terminal disclaimer.

(21) Appl. No.: 13/334,881

(22) Filed: Dec. 22, 2011

(65) Prior Publication Data

US 2012/0094311 A1  Apr. 19, 2012

Related U.S. Application Data

(60) Continuation of application No. 12/284,397, filed on Sep. 22, 2008, now Pat. No. 8,129,125, which is a division of application No. 12/072,651, filed on Feb. 27, 2008, now abandoned.

(60) Provisional application No. 60/903,694, filed on Feb. 27, 2007.

(51) Int. Cl.
*G01N 33/53* (2006.01)
*C12Q 1/68* (2006.01)
*G01N 33/574* (2006.01)

(52) U.S. Cl.
CPC ........ *G01N 33/57423* (2013.01); *C12Q 1/6886* (2013.01); *G01N 2333/71* (2013.01); *C12Q 2600/118* (2013.01); *C12Q 2600/106* (2013.01)
USPC ......................................................... 435/7.1

(58) Field of Classification Search
CPC ..................................................... A61K 39/00
See application file for complete search history.

(56) References Cited

U.S. PATENT DOCUMENTS

| 5,288,477 | A  | 2/1994  | Bacus et al.    |
| 5,587,458 | A  | 12/1996 | King et al.     |
| 6,004,755 | A  | 12/1999 | Wang            |
| 6,218,114 | B1 | 4/2001  | Peck et al.     |
| 6,218,122 | B1 | 4/2001  | Friend et al.   |
| 6,271,002 | B1 | 8/2001  | Linsley et al.  |
| 6,465,618 | B1 | 10/2002 | Nishida et al.  |
| 6,582,946 | B1 | 6/2003  | Webster et al.  |
| 6,653,084 | B1 | 11/2003 | King et al.     |
| 6,727,072 | B2 | 4/2004  | Spaulding et al.|
| 7,129,040 | B2 | 10/2006 | Steck et al.    |
| 2003/0194734 | A1 | 10/2003 | Jatkoe        |
| 2007/0202496 | A1 | 8/2007  | Beretta       |

FOREIGN PATENT DOCUMENTS

WO  9944062  9/1999

OTHER PUBLICATIONS

Borczuk, A.C. et al., Molecular signatures in biopsy specimens of lung cancer. Am J Respir Crit Care Med. Jul. 15, 2004;170(2):167-74.
Freije, W.A. et al., Gene expression profiling of gliomas strongly predicts survival. Cancer Res. Sep. 15, 2004;64 (18):6503-10.
Shai, R. et al., Gene expression profiling identifies molecular subtypes of gliomas. Oncogene. Jul. 31, 2003;22 (31):4918-23.
Gordon, G.J. et al., Translation of microarray data into clinically relevant cancer diagnostic tests using gene expression ratios in lung cancer and mesothelioma. Cancer Res. Sep. 1, 2002;62(17):4963-7.
Bild, A.H. et al., Oncogenic pathway signatures in human cancers as a guide to targeted therapies. Nature. Jan. 19, 2006;439(7074):353-7.
Chen, H. et al., Aberrant methylation of FBN2 in human non-small cell lung cancer. Lung Cancer. Oct. 2005;50 (1):43-9.
International search report for PCT/US08/02602, dated Sep. 4, 2008.
Chen, H.Y. et al., A five-gene signature and clinical outcome in non-small-cell lung cancer. N Engl J Med. Jan. 4, 2007;356(1):11-20.
Lu, Y. et al., A gene expression signature predicts survival of patients with stage I non-small cell lung cancer. PLoS Med. Dec. 2006;3(12):e467.
Montesano, R. et al., Genetic alterations in esophageal cancer and their relevance to etiology and pathogenesis: a review. Int J Cancer. Jun. 21, 1996;69(3):225-35.
Burmer, G.C. et al., Frequency and spectrum of c-Ki-ras mutations in human sporadic colon carcinoma, carcinomas arising in ulcerative colitis, and pancreatic adenocarcinoma. Environ Health Perspect. Jun. 1991;93:27-31.
Kibel, A.S. et al., Loss of heterozygosity at 12P12-13 in primary and metastatic prostate adenocarcinoma. J Urol. Jul. 2000;164(1):192-6.
Miyakawa, M. et al., Increased expression of phosphorylated p70S6 kinase and Akt in papillary thyroid cancer tissues. Endocr J. Feb. 2003;50(1):77-83.
Greenbaum, D. et al., Comparing protein abundance and mRNA expression levels on a genomic scale. Genome Biol. 2003;4(9):117.
Hell, K. et al., Hodgkin cells accumulate mRNA for bcl-2. Lab Invest. Oct. 1995;73(4):492-6.
Fu, L. et al., Translational regulation of human p53 gene expression. EMBO J. Aug. 15, 1996;15(16):4392-401.
Tockman, M.S. et al., Considerations in bringing a cancer biomarker to clinical application. Cancer Res. May 1, 1992;52(9 Suppl):2711s-2718s.

(Continued)

*Primary Examiner* — Sean Aeder
(74) *Attorney, Agent, or Firm* — Donna T. Ward; Lingyun Jia; DT Ward P.C.

(57) ABSTRACT

The present invention provides protein and gene expression profiles indicative of whether a patient afflicted with non-small cell lung cancer is likely to be responsive to treatment with a therapeutic compound that is a EGFR-TK inhibitor. By identifying such responsiveness, a treatment provider may determine in advance those patients who would benefit from such treatment, as well as identify alternative therapies for non-responders. The present invention further provide methods of using the gene and protein expression profiles, and assays for identifying the presence of a gene or protein expression profile in a patient sample.

14 Claims, No Drawings

(56) References Cited

OTHER PUBLICATIONS

Yilmaz, A. et al., Distribution of Bcl-2 gene expression and its prognostic value in non-small cell lung cancer. Tuberk Toraks. 2005;53(4):323-9.
Balko, J.M. et al., Gene expression patterns that predict sensitivity to epidermal growth factor receptor tyrosine kinase inhibitors in lung cancer cell lines and human lung tumors. BMC Genomics. Nov. 10, 2006;7:289.
Minami, K. et al., Prognostic significance of p53, Ki-67, VEGF and Glut-1 in resected stage I adenocarcinoma of the lung. Lung Cancer. Oct. 2002;38(1):51-7.
Dong, J.T. et al., Deletion at 13q21 is associated with aggressive prostate cancers. Cancer Res. Jul. 15, 2000;60 (14):3880-3.
Russo, V. et al., Expression of the MAGE gene family in primary and metastatic human breast cancer: implications for tumor antigen-specific immunotherapy. Int J Cancer. Jun. 22, 1995;64(3):216-21.
Yamasaki, F. et al., Acquired resistance to erlotinib in A-431 epidermoid cancer cells requires down-regulation of MMAC1/PTEN and up-regulation of phosphorylated Akt. Cancer Res. Jun. 15, 2007;67(12):5779-88.
Hsieh, A.C. et al., Targeting HER proteins in cancer therapy and the role of the non-target HER3. Br J Cancer. Aug. 20, 2007;97(4):453-7. Epub Jul. 31, 2007.
Schmid, S. et al., Expression of AMPA receptor subunit flip/flop splice variants in the rat auditory brainstem and inferior colliculus. J Comp Neurol. Feb. 5, 2001;430(2):160-71.
Conner, B. et al., Trk receptor alterations in Alzheimer's disease. Brain Res Mol Brain Res. Nov. 1996;42(1):1-17.
Zembutsu, H. et al., Gene-expression profiles of human tumor xenografts in nude mice treated orally with the EGFR tyrosine kinase inhibitor ZD1839. Int J Oncol. Jul. 2003;23(1):29-39.
Busken, C et al, Digestive Disease Week Abstracts and Itinerary Planner, 2003, abstract No. 850.
Bhattacharjee, A. et al., Classification of human lung carcinomas by mRNA expression profiling reveals distinct adenocarcinoma subclasses. Proc Natl Acad Sci U S A. Nov. 20, 2001;98(24):13790-5.
Garber, M.E. et al., Diversity of gene expression in adenocarcinoma of the lung. Proc Natl Acad Sci U S A. Nov. 20, 2001;98(24):13784-9.
Tsao, M.S. et al., Erlotinib in lung cancer—molecular and clinical predictors of outcome. N Engl J Med. Jul. 14, 2005;353(2):133-44.
Muller-Tidow, C. et al., Identification of metastasis-associated receptor tyrosine kinases in non-small cell lung cancer. Cancer Res. Mar. 1, 2005;65(5):1778-82.
Beer, D.G. et al., Gene-expression profiles predict survival of patients with lung adenocarcinoma. Nat Med. Aug. 2002;8(8):816-24.
Sun, Z. et al., Can gene expression profiling predict survival for patients with squamous cell carcinoma of the lung? Mol Cancer. Dec. 3, 2004;3(1):35.
Wigle, D.A. et al., Molecular profiling of non-small cell lung cancer and correlation with disease-free survival. Cancer Res. Jun. 1, 2002;62(11):3005-8.
Golub T.R. et al., Molecular classification of cancer: class discovery and class prediction by gene expression monitoring. Science. Oct. 15, 1999;286(5439):531-7.
Wang, Y. et al., Gene expression profiles and molecular markers to predict recurrence of Dukes' B colon cancer. J Clin Oncol. May 1, 2004;22(9):1564-71.
Schena, M. et al., Quantitative monitoring of gene expression patterns with a complementary DNA microarray. Science. Oct. 20, 1995;270(5235):467-70.
Saviozzi, S. et al., Selection of suitable reference genes for accurate normalization of gene expression profile studies in non-small cell lung cancer. BMC Cancer. Jul. 26, 2006;6:200.
Lee, P.D. et al., Control genes and variability: absence of ubiquitous reference transcripts in diverse mammalian expression studies. Genome Res. Feb. 2002;12(2):292-7.
Zhang, X. et al., Selection of reference genes for gene expression studies in human neutrophils by real-time PCR. BMC Mol Biol. Feb. 18, 2005;6(1):4.
Xu, H. et al., A smooth response surface algorithm for constructing a gene regulatory network. Physiol Genomics. Oct. 2, 2002;11(1):11-20.
Irizarry, R.A. et al., Summaries of Affymetrix GeneChip probe level data. Nucleic Acids Res. Feb. 15, 2003;31(4): e15.
Su, A.I. et al., Molecular classification of human carcinomas by use of gene expression signatures. Cancer Res. Oct. 15, 2001;61(20):7388-93.
Ramaswamy, S. et al., Multiclass cancer diagnosis using tumor gene expression signatures. Proc Natl Acad Sci U S A. Dec. 18, 2001;98(26):15149-54.
Van't Veer, L.J. et al., Gene expression profiling predicts clinical outcome of breast cancer. Nature. Jan. 31, 2002;415 (6871):530-6.
Hofer, M.D. et al., Identification of two molecular groups of seminomas by using expression and tissue microarrays. Clin Cancer Res. Aug. 15, 2005;11(16):5722-9.
Volm, M. et al., Protein expression profile of primary human squamous cell lung carcinomas indicative of the incidence of metastases. Clin Exp Metastasis. 2002;19(5):385-90.
Simon, R. et al., Tissue microarrays. Biotechniques. Jan. 2004;36(1):98-105.
Kononen, J. et al., Tissue microarrays for high-throughput molecular profiling of tumor specimens. Nat Med. Jul. 1998;4(7):844-7.
Jaiswal, J.K. et al. Long-term multiple color imaging of live cells using quantum dot bioconjugates. Nat Biotechnol. Jan. 2003;21(1):47-51.
Chan, W.C. et al., Luminescent quantum dots for multiplexed biological detection and imaging. Curr Opin Biotechnol. Feb. 2002;13(1):40-6.
Chan, W.C. et al., Quantum dot bioconjugates for ultrasensitive nonisotopic detection. Science. Sep. 25, 1998;281 (5385):2016-8.
Haedicke, W., et al. Automated evaluation and normalization of immunohistochemistry on tissue microarrays with a DNA microarray scanner. Biotechniques. Jul. 2003;35(1):164-8.
Signoretti, S. et al., Her-2-neu expression and progression toward androgen independence in human prostate cancer. J Natl Cancer Inst. Dec. 6, 2000;92(23):1918-25.
Gu, Z. et al., Prostate stem cell antigen (PSCA) expression increases with high gleason score, advanced stage and bone metastasis in prostate cancer. Oncogene. Mar. 2, 2000;19(10):1288-96.
Han et al., "Epidermal Growth Factor Receptor (EGFR) Downstream Molecules as Response Predictive Markers for Gefitinib (Iressa(R), ZD1839) in Chemotherapy-Resistant Non-Small Cell Lunch Cancer." Int. J. Cancer, vol. 113, No. 1, Jan. 1, 2005, pp. 109-115, XP002563767.
Cappuzzo et al., "Akt Phosphorylation and Gefitinib Efficacy in Patients With Advanced Non-Small-Cell Lung Cancer." Journal of the National Cancer Institute, vol. 96, No. 15, Aug. 4, 2004, pp. 1133-1141, XP002563768.
European Search Report for EP Application No. 11008690.7 dated Dec. 28, 2011, 5 pages.

SEQUENCE LISTING

```
<160> NUMBER OF SEQ ID NOS: 32

<210> SEQ ID NO 1
<211> LENGTH: 5332
<212> TYPE: DNA
<213> ORGANISM: Homo sapiens

<400> SEQUENCE: 1
gctgaacttt aggagccagt ctaaggccta ggcgcagacg cactgagcct aagcagccgg      60
tgatggcggc agcggctgtg gtggctgcgg cgggtccggg cccatgaggc gacgaaggag     120
gcgggacggc ttttacccag ccccggactt ccgagacagg gaagctgagg acatggcagg     180
agtgtttgac atagacctgg accagccaga ggacgcgggc tctgaggatg agctggagga     240 gggggtcag ttaaatgaaa gcatggacca tgggggagtt ggaccatatg aacttggcat     300
ggaacattgt gagaaatttg aaatctcaga aactagtgtg aacagagggc cagaaaaaat     360
cagaccagaa tgttttgagc tacttcgggt acttggtaaa gggggctatg gaaaggtttt     420
tcaagtacga aaagtaacag gagcaaatac tgggaaaata tttgccatga aggtgcttaa     480
aaaggcaatg atagtaagaa atgctaaaga tacagctcat acaaaagcag aacgaaatat     540
tctggaggaa gtaaagcatc ccttcatcgt ggatttaatt tatgcctttc agactggtgg     600
aaaactctac ctcatccttg agtatctcag tggaggagaa ctatttatgc agttagaaag     660
agagggaata tttatggaag acactgcctg cttttacttg gcagaaatct ccatggcttt     720
ggggcattta catcaaaagg ggatcatcta cagagacctg aagccggaga atatcatgct     780
taatcaccaa ggtcatgtga aactaacaga ctttggacta tgcaaagaat ctattcatga     840
tggaacagtc acacacacat tttgtggaac aatagaatac atggcccctg aaatcttgat     900
gagaagtggc cacaatcgtg ctgtggattg gtggagtttg ggagcattaa tgtatgacat     960
gctgactgga gcaccccat tcactgggga aatagaaag aaaacaattg acaaaatcct    1020
caaatgtaaa ctcaatttgc ctccctacct cacacaagaa gccagagatc tgcttaaaaa    1080
gctgctgaaa agaaatgctg cttctcgtct gggagctggt cctggggacg ctggagaagt    1140
tcaagctcat ccattcttta gacacattaa ctggaagaa cttctggctc gaaaggtgga    1200
gccccctttt aaacctctgt tgcaatctga agaggatgta agtcagtttg attccaagtt    1260
```

```
tacacgtcag acacctgtcg acagcccaga tgactcaact ctcagtgaaa gtgccaatca   1320
ggtcttctg ggttttacat atgtggctcc atctgtactt gaaagtgtga agaaaagtt    1380
ttcctttgaa ccaaaaatcc gatcacctcg aagatttatt ggcagcccac gaacacctgt   1440
cagcccagtc aaattttctc ctggggattt ctggggaaga ggtgcttcgg ccagcacagc   1500
aaatcctcag acacctgtgg aatacccaat ggaaacaagt ggcatagagc agatggatgt   1560
gacaatgagt ggggaagcat cggcaccact tccaatacga cagccgaact ctgggccata   1620
caaaaaacaa gcttttccca tgatctccaa acggccagag cacctgcgta tgaatctatg   1680
acagagcaat gcttttaatg aatttaaggc aaaaaggtg gagagggaga tgtgtgagca   1740
tcctgcaagg tgaaacgact caaaatgaca gtttcagaga gtcaatgtca ttacatagaa   1800
cacttcagac acaggaaaaa taaacgtgga ttttaaaaaa tcaatcaatg gtgcaaaaaa   1860
aaacttaaag caaaatagta ttgctgaact cttaggcaca tcaattaatt gattcctcgc   1920
gacatcttct caaccttatc aaggattttc atgttgatga ctcgaaactg acagtattaa   1980
gggtaggatg ttgcttctga atcactgttg agttctgatt gtgttgaaga agggttatcc   2040
tttcattagg caaagtacaa aattgcctat aatacttgca actaaggaca aattagcatg   2100
caagcttggt caaacttttt ccagcaaaat ggaagcaaag acaaagaaa cttaccaatt    2160
gatgttttac gtgcaaacaa cctgaatctt ttttttatat aaatatatat ttttcaaata   2220
gattttgat tcagctcatt atgaaaaaca tcccaaactt taaatgcga aattattggt     2280
tggtgtgaag aaagccagac aacttctgtt tcttctcttg gtgaaataat aaaatgcaaa   2340
tgaatcattg ttaccacag ctgtggctcg tttgagggat tggggtggac ctggggttta    2400
ttttcagtaa cccagctgca atacctgtct gtaatatgag aaaaaaaaaa tgaatctatt   2460
taatcatttc tacttgcagt actgctatgt gctaagctta actggaagcc ttggaatggg   2520
cataagttgt atgtcctaca tttcatcatt gtcccgggcc tgcattgcac tggaaaaaaa   2580
aatcgccacc tgttcttaca ccagtatttg gttcaagaca ccaaatgtct tcagcccatg   2640
gctgaagaac aacagaagag agtcaggata aaaaatacat actgtggtcg gcaaggtgag   2700
ggagataggg atatccaggg gaagagggtg ttgctgtggc ccactctctg tctaatctct   2760
ttacagcaaa ttggtaagat tttcagtttt acttcttct actgtttctg ctgtctacct    2820
tccttatatt ttttcctca acagttttaa aagaaaaaa aggtctattt ttttttctcc     2880
tatacttggg ctacattttt tgattgtaaa aatatttgat ggccttttga tgaatgtctt   2940
ccacagtaaa gaaaacttag tggcttaatt taggaaacat gttaacagga cactatgttt   3000
ttgaaattgt aacaaaatct acataaatga tttacaggtt aaaagaataa aataaaggt    3060
aactttacct ttcttaaata tttcctgcct taaagagagc atttccatga ctttagctgg   3120
tgaaagggtt taatatctgc agagctttat aaaaatatat ttcagtgcat actggtataa   3180
tagatgatca tgcagttgca gttgagttgt atcacctttt ttgtttgtct tttataatgt   3240
cttcagtctg agtgtgcaaa gtcaatttgt aatattttgc aaccctagga tttttttaaa   3300
tagatgctgc ttgctatgtt ttcaaacctt tttgagccat aggatccaag ccataaaatt   3360
ctttatgcat gttgaattca gtcagaaaag agcaaggctt tgcttttttga aattgcaact   3420
caaatgagat gggatgaaat cctatgacag taagcaaaaa cagaaccatg aaaaatgatt   3480
ggacatacac cttttcaatt gtggcaataa ttgaaagaat cgataaaagt tcatctttgg   3540
acagaaagcc tttaaaaaaa aaatcactcc ctcttccccc tcctccctta ttgcagcagc   3600
ctactgagaa cttgactgt tgctggtaaa ttagaagcta caataataat taagggcaga    3660
```

| | |
|---|---|
| aattatactt aaaaagtgca gatccttgtt ctttgacaat ttgtgatgtc tgaaaaaaca | 3720 |
| gaacccgaaa agctatggtg atatgtacag gcattatttc agactgtaaa tggcttgtga | 3780 |
| tactcttgat acttgttttc aaatatgttt actaactgta gtgttgactg cctgaccaaa | 3840 |
| ttccagtgaa acttatacac caaaatattc ttcctaggtc ctatttgcta gtaacatgag | 3900 |
| cactgtgatt ggctggctat aaccacccca gttaaaccat tttcataatt agtagtgcca | 3960 |
| gcaatagtgg caaacactgc aacttttctg cataaaaagc attaattgca cagctaccat | 4020 |
| ccacacaaat acatagtttt tctgacttca catttattaa gtgaaattta tttcccatgc | 4080 |
| tgtggaaagt ttattgagaa cttgtttcat aaatggatat ccctactatg actgtgaaaa | 4140 |
| catgtcaagt gtcacattag tgtcacagac agaaagcaca cacctatgca atatggctta | 4200 |
| tctatattta tttgtaaaaa tccaagcata gtttaaaata tgatgtcgat attactagtc | 4260 |
| ttgagtttct aagagggttc tttatgttat accaggtaag tgtataaaag agattaagtg | 4320 |
| cttttttttc atcacttgat tattttcttt aaaatcagct attacaggat attttttat | 4380 |
| tttatacatg ctgttttta attaaaatat aatcactgaa gtttactaat ttgattttat | 4440 |
| aaggtttgta gcattacaga ataactaaac tgggatttat aaaccagctg tgattaacaa | 4500 |
| tgtaaagtat taattattga actttgaacc agattttag gaaaattatg ttcttttcc | 4560 |
| ccctttatgg tcttaactaa tttgaatcct tcaagaagga ttttttccata ctattttta | 4620 |
| agatagaaga taatttgtgg gcagggtgg aggatgcatg tatgatactc cataaattca | 4680 |
| acattcttta ctataggtaa tgaatgatta taaacaagat gcatcttaga tagtattaat | 4740 |
| atactgagcc ttggattata tatttaatat aggaccctatt ttgaatattc agttaatcat | 4800 |
| atggttccta gcttacaagg gctagatcta agattattcc catgagaaat gttgaattta | 4860 |
| tgaagaatag attttaaggc tttgaaaatg gttaatttct caaaaacatc aatgtccaaa | 4920 |
| catctacctt ttttcatagg agtagacact agcaagctgg acaaactatc acaaaagtat | 4980 |
| ttgtcacaca taacctgtgg tctgttgctg attaatacag tacttttcct tgtgtgattc | 5040 |
| ttaacattat agcacaagta ttatctcagt ggattatccg gaataacatc tgaaagatgg | 5100 |
| gttcatctat gtttgtgttt gctcttaaaa ctattgtttc tcctatccca agttcgcttt | 5160 |
| gcatctatca gtaaataaaa ttcttcagct gccttattag gagtgctatg agggtaacac | 5220 |
| ctgttctgct tttcatcttg tatttagttg actgtattat ttgatttcgg attgaatgaa | 5280 |
| tgtaaataga aattaaatgc aaatttgaat gaacataaaa aaaaaaaaa aa | 5332 |

<210> SEQ ID NO 2
<211> LENGTH: 829
<212> TYPE: DNA
<213> ORGANISM: Homo sapiens

<400> SEQUENCE: 2

| | |
|---|---|
| cctctttcc gtggcgcctc ggaggcgttc agctgcttca agatgaagct gaacatctcc | 60 |
| ttcccagcca ctggctgcca gaaactcatt gaagtggacg atgaacgcaa acttcgtact | 120 |
| ttctatgaga agcgtatggc cacagaagtt gctgctgacg ctctgggtga agaatggaag | 180 |
| ggttatgtgg tccgaatcag tggtgggaac gacaaacaag gtttccccat gaagcagggt | 240 |
| gtcttgaccc atggccgtgt ccgcctgcta ctgagtaagg ggcattcctg ttacagacca | 300 |
| aggagaactg gagaaagaaa gagaaaatca gttcgtggtt gcattgtgga tgcaaatctg | 360 |
| agcgttctca acttggttat tgtaaaaaaa ggagagaagg atattcctgg actgactgat | 420 |

-continued

| | |
|---|---|
| actacagtgc ctcgccgcct gggccccaaa agagctagca gaatccgcaa acttttcaat | 480 |
| ctctctaaag aagatgatgt ccgccagtat gttgtaagaa agcccttaaa taaagaaggt | 540 |
| aagaaaccta ggaccaaagc acccaagatt cagcgtcttg ttactccacg tgtcctgcag | 600 |
| cacaaacggc ggcgtattgc tctgaagaag cagcgtacca agaaaaataa agaagaggct | 660 |
| gcagaatatg ctaaactttt ggccaagaga atgaaggagg ctaaggagaa gcgccaggaa | 720 |
| caaattgcga agagacgcag actttcctct ctgcgagctt ctacttctaa gtctgaatcc | 780 |
| agtcagaaat aagattttt gagtaacaaa taaataagat cagactctg | 829 |

<210> SEQ ID NO 3
<211> LENGTH: 3008
<212> TYPE: DNA
<213> ORGANISM: Homo sapiens

<400> SEQUENCE: 3

| | |
|---|---|
| taattatggg tctgtaacca ccctggactg ggtgctcctc actgacggac ttgtctgaac | 60 |
| ctctctttgt ctccagcgcc cagcactggg cctggcaaaa cctgagacgc ccggtacatg | 120 |
| ttggccaaat gaatgaacca gattcagacc ggcaggggcg ctgtggttta ggaggggcct | 180 |
| ggggtttctc ccaggaggtt tttggccttg cgctggaggg ctctggactc ccgtttgcgc | 240 |
| cagtggcctg catcctggtc ctgtcttcct catgtttgaa tttctttgct ttcctagtct | 300 |
| ggggagcagg gaggagccct gtgccctgtc ccaggatcca tgggtaggaa caccatggac | 360 |
| agggagagca acggggcca tctgtcacca ggggcttagg aaggccgag ccagcctggg | 420 |
| tcaaagaagt caaaggggct gcctggagga ggcagcctgt cagctggtgc atcagaggct | 480 |
| gtggccaggc cagctgggct cggggagcgc cagcctgaga ggagcgcgtg agcgtcgcgg | 540 |
| gagcctcggg caccatgagc gacgtggcta ttgtgaagga gggttggctg cacaaacgag | 600 |
| gggagtacat caagacctgg cggccacgct acttcctcct caagaatgat ggcaccttca | 660 |
| ttggctacaa ggagcggccg caggatgtgg accaacgtga ggctcccctc aacaacttct | 720 |
| ctgtggcgca gtgccagctg atgaagacgg agcggccccg gcccaacacc ttcatcatcc | 780 |
| gctgcctgca gtggaccact gtcatcgaac gcaccttcca tgtggagact cctgaggagc | 840 |
| gggaggagtg gacaaccgcc atccagactg tggctgacgg cctcaagaag caggaggagg | 900 |
| aggagatgga cttccggtcg ggctcaccca gtgacaactc aggggctgaa gagatggagg | 960 |
| tgtccctggc caagcccaag caccgcgtga ccatgaacga gtttgagtac ctgaagctgc | 1020 |
| tgggcaaggg cactttcggc aaggtgatcc tggtgaagga aaggccaca ggccgctact | 1080 |
| acgccatgaa gatcctcaag aaggaagtca tcgtggccaa ggacgaggtg gcccacacac | 1140 |
| tcaccgagaa ccgcgtcctg cagaactcca ggcacccctt cctcacagcc tgaagtact | 1200 |
| ctttccagac ccacgaccgc ctctgctttg tcatggagta cgccaacggg ggcgagctgt | 1260 |
| tcttccacct gtcccgggag cgtgtgttct ccgaggaccg ggcccgcttc tatgcgctg | 1320 |
| agattgtgtc agccctggac tacctgcact cggagaagaa cgtggtgtac cgggacctca | 1380 |
| agctggagaa cctcatgctg gacaaggacg ggcacattaa gatcacagac ttcgggctgt | 1440 |
| gcaaggaggg gatcaaggac ggtgccacca tgaagacct ttgcggcaca cctgagtacc | 1500 |
| tggccccga ggtgctggag acaatgact acggccgtgc agtggactgg tgggggctgg | 1560 |
| gcgtggtcat gtacgagatg atgtgcggtc gcctgccctt ctacaaccag gaccatgaga | 1620 |
| agcttttga gctcatcctc atggaggaga tccgcttccc gcgcacgctt ggtcccgagg | 1680 |
| ccaagtcctt gctttcaggg ctgctcaaga aggaccccaa gcagaggctt ggcggggct | 1740 |

```
ccgaggacgc caaggagatc atgcagcatc gcttctttgc cggtatcgtg tggcagcacg   1800
tgtacgagaa gaagctcagc ccaccttca agccccaggt cacgtcggag actgacacca    1860
ggtattttga tgaggagttc acggcccaga tgatcaccat cacaccacct gaccaagatg   1920
acagcatgga gtgtgtggac agcgagcgca ggccccactt cccccagttc tcctactcgg   1980
ccagcggcac ggcctgaggc ggcggtggac tgcgctggac gatagcttgg agggatggag   2040
aggcggcctc gtgccatgat ctgtatttaa tggtttttat ttctcgggtg catttgagag   2100
aagccacgct gtcctctcga gcccagatgg aaagacgttt tgtgctgtg ggcagcaccc    2160 tcccccgcag cggggtaggg aagaaaacta tcctgcgggt tttaatttat ttcatccagt   2220
ttgttctccg ggtgtggcct cagccctcag aacaatccga ttcacgtagg gaaatgttaa   2280
ggacttctgc agctatgcgc aatgtggcat tgggggccg gcaggtcct gcccatgtgt     2340 cccctcactc tgtcagccag ccgccctggg ctgtctgtca ccagctatct gtcatctctc   2400
tggggccctg gcctcagtt caacctggtg gcaccagatg caacctcact atggtatgct    2460
ggccagcacc ctctcctggg ggtggcaggc acacagcagc cccccagcac taaggccgtg   2520
tctctgagga cgtcatcgga ggctgggccc ctgggatggg accagggatg gggatgggc    2580 cagggtttac ccagtgggac agaggagcaa ggtttaaatt tgttattgtg tattatgttg   2640
ttcaaatgca ttttgggggt ttttaatctt tgtgacagga aagccctccc ccttccctt    2700 ctgtgtcaca gttcttggtg actgtccac cgggagcctc cccctcagat gatctctcca    2760
cggtagcact tgaccttttc gacgcttaac ctttccgctg tcgccccagg ccctcccctga  2820 ctccctgtgg gggtggccat ccctgggccc ctccacgcct cctggccaga cgctgccgct   2880
gccgctgcac cacggcgttt ttttacaaca ttcaactta gtattttac tattataata     2940 taatatggaa ccttccctcc aaattcttca ataaagttg cttttcaaaa aaaaaaaaa     3000 aaaaaaaa                                                            3008
```

<210> SEQ ID NO 4
<211> LENGTH: 8680
<212> TYPE: DNA
<213> ORGANISM: Homo sapiens

<400> SEQUENCE: 4

```
acggggcctg aagcggcggt accggtgctg gcggcggcag ctgaggcctt ggccgaagcc   60
gcgcgaacct cagggcaaga tgcttggaac cggacctgcc gccgccacca ccgctgccac   120
cacatctagc aatgtgagcg tcctgcagca gtttgccagt ggcctaaaga gccggaatga   180
ggaaaccagg gccaaagccg ccaaggagct ccagcactat gtcaccatgg aactccgaga   240
gatgagtcaa gaggagtcta ctcgcttcta tgaccaactg aaccatcaca ttttgaatt    300 ggtttccagc tcagatgcca atgagaggaa aggtggcatc ttggccatag ctagcctcat   360
aggagtggaa ggtgggaatg ccacccgaat tggcagattt gccaactatc tcggaacct    420 cctcccctcc aatgacccag ttgtcatgga aatggcatcc aaggccattg ccgtcttgc    480 catggcaggg gacacttta ccgctgagta cgtggaattt gaggtgaagc gagccctgga    540
atggctgggt gctgaccgca atgagggccg agacatgca gctgtcctgg ttctccgtga    600
gctggccatc agcgtcccta ccttcttctt ccagcaagtg caaccctttct ttgacaacat  660 ttttgtggcc gtgtgggacc ccaaacaggc catccgtgag ggagctgtag ccgcccttcg   720
tgcctgtctg attctcacaa cccagcgtga gccgaaggag atgcagaagc ctcagtggta   780
```

| | |
|---|---|
| caggcacaca tttgaagaag cagagaaggg atttgatgag accttggcca aagagaaggg | 840 |
| catgaatcgg gatgatcgga tccatggagc cttgttgatc cttaacgagc tggtccgaat | 900 |
| cagcagcatg gagggagagc gtctgagaga agaaatggaa gaaatcacac agcagcagct | 960 |
| ggtacacgac aagtactgca aagatctcat gggcttcgga acaaaacctc gtcacattac | 1020 |
| cccttcacc agtttccagg ctgtacagcc ccagcagtca aatgccttgg tggggctgct | 1080 |
| ggggtacagc tctcaccaag gcctcatggg atttgggacc tcccccagtc cagctaagtc | 1140 |
| caccctggtg gagagccggt gttgcagaga cttgatggag gagaaatttg atcaggtgtg | 1200 |
| ccagtgggtg ctgaaatgca ggaatagcaa gaactcgctg atccaaatga caatccttaa | 1260 |
| tttgttgccc cgcttggctg cattccgacc ttctgccttc acagataccc agtatctcca | 1320 |
| agataccatg aaccatgtcc taagctgtgt caagaaggag aaggaacgta cagcggcctt | 1380 |
| ccaagccctg gggctacttt ctgtggctgt gaggtctgag tttaaggtct atttgcctcg | 1440 |
| cgtgctggac atcatccgag cggccctgcc cccaaaggac ttcgcccata gaggcagaa | 1500 |
| ggcaatgcag gtggatgcca cagtcttcac ttgcatcagc atgctggctc gagcaatggg | 1560 |
| gccaggcatc cagcaggata tcaaggagct gctggagccc atgctggcag tgggactaag | 1620 |
| ccctgccctc actgcagtgc tctacgacct gagccgtcag attccacagc taagaagga | 1680 |
| cattcaagat gggctactga aaatgctgtc cctggtcctt atgcacaaac cccttcgcca | 1740 |
| cccaggcatg cccaagggcc tgcccatca gctggcctct cctggcctca cgaccctccc | 1800 |
| tgaggccagc gatgtgggca gcatcactct tgccctccga acgcttggca gctttgaatt | 1860 |
| tgaaggccac tctctgaccc aatttgttcg ccactgtgcg gatcatttcc tgaacagtga | 1920 |
| gcacaaggag atccgcatgg aggctgcccg cacctgctcc cgcctgctca caccctccat | 1980 |
| ccacctcatc agtggccatg ctcatgtggt tagccagacc gcagtgcaag tggtggcaga | 2040 |
| tgtgcttagc aaactgctcg tagttgggat aacagatcct gaccctgaca ttcgctactg | 2100 |
| tgtcttggcg tccctggacg agcgcttttga tgcacacctg gcccaggcgg agaacttgca | 2160 |
| ggccttgttt gtggctctga atgaccaggt gtttgagatc cgggagctgg ccatctgcac | 2220 |
| tgtgggccga ctcagtagca tgaacccttgc cttttgtcatg cctttcctgc gcaagatgct | 2280 |
| catccagatt ttgacagagt tggagcacag tgggattgga agaatcaaag agcagagtgc | 2340 |
| ccgcatgctg gggcacctgg tctccaatgc cccccgactc atccgcccct acatggagcc | 2400 |
| tattctgaag gcattaattt tgaaactgaa agatccagac cctgatccaa acccaggtgt | 2460 |
| gatcaataat gtcctggcaa caataggaga attggcacag gttagtggcc tggaaatgag | 2520 |
| gaaatgggtt gatgaacttt ttattatcat catggacatg ctccaggatt cctctttgtt | 2580 |
| ggccaaaagg caggtggctc tgtggaccct gggacagttg gtggccagca ctggctatgt | 2640 |
| agtagagccc tacaggaagt accctacttt gcttgaggtg ctactgaatt ttctgaagac | 2700 |
| tgagcagaac cagggtacac gcagagaggc catccgtgtg ttagggcttt tagggctttt | 2760 |
| ggatccttac aagcacaaag tgaacattgg catgatagac cagtcccggg atgcctctgc | 2820 |
| tgtcagcctg tcagaatcca agtcaagtca ggattcctct gactatagca ctagtgaaat | 2880 |
| gctggtcaac atgggaaact gcctctgga tgagttctac ccagctgtgt ccatggtggc | 2940 |
| cctgatgcgg atcttccgag accagtcact ctctcatcat cacaccatgg ttgtccaggc | 3000 |
| catcaccttc atcttcaagt ccctgggact caaatgtgtg cagttcctgc cccaggtcat | 3060 |
| gcccacgttc cttaacgtca ttcgagtctg tgatggggcc atccgggaat ttttgttcca | 3120 |
| gcagctggga atgttggtgt cctttgtgaa gagccacatc agaccttata tggatgaaat | 3180 |

```
agtcaccctc atgagagaat tctgggtcat gaacacctca attcagagca cgatcattct   3240
tctcattgag caaattgtgg tagctcttgg gggtgaattt aagctctacc tgccccagct   3300
gatcccacac atgctgcgtg tcttcatgca tgacaacagc ccaggccgca ttgtctctat   3360
caagttactg gctgcaatcc agctgtttgg cgccaacctg gatgactacc tgcatttact   3420
gctgcctcct attgttaagt tgtttgatgc ccctgaagct ccactgccat ctcgaaaggc   3480
agcgctagag actgtggacc gcctgacgga gtccctggat ttcactgact atgcctcccg   3540
gatcattcac cctattgttc gaacactgga ccagagccca gaactgcgct ccacagccat   3600
ggacacgctg tcttcacttg ttttcagct ggggaagaag taccaaattt tcattccaat   3660
ggtgaataaa gttctggtgc gacaccgaat caatcatcag cgctatgatg tgctcatctg   3720
cagaattgtc aagggataca cacttgctga tgaagaggag gatcctttga tttaccagca   3780
tcggatgctt aggagtggcc aaggggatgc attggctagt ggaccagtgg aaacaggacc   3840
catgaagaaa ctgcacgtca gcaccatcaa cctccaaaag gcctgggggcg ctgccaggag   3900 ggtctccaaa gatgactggc tggaatggct gagacggctg agcctggagc tgctgaagga   3960
ctcatcatcg ccctccctgc gctcctgctg ggccctggca caggcctaca cccgatggc    4020 cagggatctc ttcaatgctg catttgtgtc ctgctggtct gaactgaatg aagatcaaca   4080
ggatgagctc atcagaagca tcgagttggc cctcacctca caagacatcg ctgaagtcac   4140
acagaccctc ttaaacttgg ctgaattcat ggaacacagt gacaagggcc cctgccact   4200 gagagatgac aatggcattg ttctgctggg tgagagagct gccaagtgcc gagcatatgc   4260
caaagcacta cactacaaag aactggagtt ccagaaaggc cccacccctg ccattctaga   4320
atctctcatc agcattaata ataagctaca gcagccggag gcagcggccg gagtgttaga   4380
atatgccatg aaacactttg gagagctgga gatccaggct acctggtatg agaaactgca   4440
cgagtgggag gatgcccttg tggcctatga caagaaaatg gacaccaaca aggacgaccc   4500
agagctgatg ctgggccgca tgcgctgcct cgaggccttg ggggaatggg gtcaactcca   4560
ccagcagtgc tgtgaaaagt ggaccctggt taatgatgag acccaagcca agatggcccg   4620
gatggctgct gcagctgcat ggggtttagg tcagtgggac agcatggaag aatacacctg   4680
tatgatccct cgggacaccc atgatggggc attttataga gctgtgctgg cactgcatca   4740
ggacctcttc tccttggcac aacagtgcat tgacaaggcc agggacctgc tggatgctga   4800
attaactgcg atggcaggag agagttacag tcgggcatat ggggccatgg tttcttgcca   4860
catgctgtcc gagctggagg aggttatcca gtacaaactt gtccccgagc gacgagagat   4920
catccgccag atctggtggg agagactgca gggctgccag cgtatcgtag aggactggca   4980
gaaaatcctt atggtgcggt cccttgtggt cagcccctcat gaagacatga aacctggct    5040 caagtatgca agcctgtgcg gcaagagtgg caggctggct cttgctcata aactttagt    5100 gttgctcctg ggagttgatc cgtctccggca acttgaccat cctctgccaa cagttcaccc   5160
tcaggtgacc tatgcctaca tgaaaaacat gtggaagagt gcccgcaaga tcgatgcctt   5220
ccagcacatg cagcattttg tccagaccat gcagcaacag gcccagcatg ccatcgctac   5280
tgaggaccag cagcataagc aggaactgca caagctcatg gcccgatgct tcctgaaact   5340
tggagagtgg cagctgaatc tacagggcat caatgagagc acaatcccca aagtgctgca   5400
gtactacagc gccgccacag agcacgaccg cagctggtac aaggcctggc atgcgtgggc   5460
agtgatgaac ttcgaagctg tgctacacta caaacatcag aaccaagccc gcgatgagaa   5520
```

```
gaagaaactg cgtcatgcca gcggggccaa catcaccaac gccaccactg ccgccaccac    5580
ggccgccact gccaccacca ctgccagcac cgagggcagc aacagtgaga gcgaggccga    5640
gagcaccgag aacagcccca ccccatcgcc gctgcagaag aaggtcactg aggatctgtc    5700
caaaaccctc ctgatgtaca cggtgcctgc cgtccagggc ttcttccgtt ccatctcctt    5760
gtcacgaggc aacaacctcc aggatacact cagagttctc accttatggt ttgattatgg    5820
tcactggcca gatgtcaatg aggccttagt ggaggggtg aaagccatcc agattgatac    5880
ctggctacag gttataccte agctcattgc aagaattgat acgcccagac ccttggtggg    5940
acgtctcatt caccagcttc tcacagacat tggtcggtac cacccccagg ccctcatcta    6000
cccactgaca gtggcttcta agtctaccac gacagcccgg cacaatgcag ccaacaagat    6060
tctgaagaac atgtgtgagc acagcaacac cctggtccag caggccatga tggtgagcga    6120
ggagctgatc cgagtggcca tcctctggca tgagatgtgg catgaaggcc tggaagaggc    6180
atctcgtttg tactttgggg aaaggaacgt gaaaggcatg tttgaggtgc tggagcccett    6240
gcatgctatg atggaacggg gcccccagac tctgaaggaa acatccttta atcaggccta    6300
tggtcgagat ttaatggagg cccaagagtg gtgcaggaag tacatgaaat cagggaatgt    6360
caaggaccct cacccaagcct gggacctcta ttatcatgtg ttccgacgaa tctcaaagca    6420
gctgcctcag ctcacatcct tagagctgca atatgtttcc ccaaaacttc tgatgtgccg    6480
ggaccttgaa ttggctgtgc caggaacata tgaccccaac cagccaatca ttcgcattca    6540
gtccatagca ccgtctttgc aagtcatcac atccaagcag aggccccgga attgacact    6600
tatgggcagc aacggacatg agtttgttt ccttctaaaa ggccatgaag atctgcgcca    6660
ggatgagcgt gtgatgcagc tcttcggcct ggttaacacc cttctggcca atgacccaac    6720
atctcttcgg aaaaacctca gcatccgag atacgctgtc atccctttat cgaccaactc    6780
gggcctcatt ggctgggtc cccactgtga cacactgcac gccctcatcc gggactacag    6840
ggagaagaag aagatccttc tcaacatcga gcatcgcatc atgttgcgga tggctccgga    6900
ctatgaccac ttgactctga tgcagaaggt ggaggtgttt gagcatgccg tcaataatac    6960
agctggggac gacctggcca agctgctgtg gctgaaaagc cccagctccg aggtgtggtt    7020
tgaccgaaga accaattata cccgttcttt agcggtcatg tcaatggttg ggtatattt    7080
aggcctggga gatagacacc catccaacct gatgctggac cgtctgagtg gaagatcct    7140
gcacattgac tttgggact gctttgaggt tgctatgacc cgagagaagt tccagagaa    7200
gattccattt agactaacaa gaatgttgac caatgctatg gaggttacag gcctggatgg    7260
caactacaga atcacatgcc acacagtgat ggaggtgctg cgagagcaca aggacagtgt    7320
catgccgtg ctgaagcct ttgtctatga ccccttgctg aactggaggc tgatggacac    7380
aaataccaaa ggcaacaagc gatcccgaac gaggacggat tcctactctg ctggccagtc    7440
agtcgaaatt ttggacggtg tggaacttgg agagccagcc cataagaaaa cggggaccac    7500
agtgccagaa tctattcatt ctttcattgg agacggtttg gtgaaaccag aggccctaaa    7560
taagaaagct atccagatta ttaacagggt tcgagataag ctcactggtc gggacttctc    7620
tcatgatgac actttggatg ttccaacgca agttgagctg ctcatcaaac aagcgacatc    7680
ccatgaaaac ctctgccagt gctatattgg ctggtgccct ttctggtaac tggaggccca    7740
gatgtgccca tcacgttttt tctgaggctt ttgtacttta gtaaatgctt ccactaaact    7800
gaaaccatgg tgagaaagtt tgactttgtt aaatattttg aaatgtaaat gaaaagaact    7860
actgtatatt aaaagttggt ttgaaccaac tttctagctg ctgttgaaga atatattgtc    7920
```

| | |
|---|---|
| agaaacacaa ggcttgattt ggttcccagg acagtgaaac aatagtaata ccacgtaaat | 7980 |
| caagccattc attttgggga acagaagatc cataacttta gaaatacggg ttttgactta | 8040 |
| actcacaaga gaactcatca taagtacttg ctgatggaag aatgacctag ttgctcctct | 8100 |
| caacatgggt acagcaaact cagcacagcc aagaagcctc aggtcgtgga gaacatggat | 8160 |
| taggatccta gactgtaaag acacagaaga tgctgacctc accctgcca cctatcccaa | 8220 |
| gacctcactg gtctgtggac agcagcagaa atgtttgcaa gataggccaa aatgagtaca | 8280 |
| aaaggtctgt cttccatcag acccagtgat gctgcgactc acacgcttca attcaagacc | 8340 |
| tgaccgctag tagggaggtt tattcagatc gctggcagcc tcggctgagc agatgcacag | 8400 |
| aggggatcac tgtgcagtgg gaccaccctc actggccttc tgcagcaggg ttctgggatg | 8460 |
| ttttcagtgg tcaaaatact ctgtttagag caagggctca gaaaacagaa atactgtcat | 8520 |
| ggaggtgctg aacacaggga aggtctggta catattggaa attatgagca gaacaaatac | 8580 |
| tcaactaaat gcacaaagta taaagtgtag ccatgtctag acaccatgtt gtatcagaat | 8640 |
| aatttttgtg ccaataaatg acatcagaat tttaaacata | 8680 |

<210> SEQ ID NO 5
<211> LENGTH: 5572
<212> TYPE: DNA
<213> ORGANISM: Homo sapiens

<400> SEQUENCE: 5

| | |
|---|---|
| cctcccctcg cccggcgcgg tcccgtccgc ctctcgctcg cctcccgcct ccctcggtc | 60 |
| ttccgaggcg cccgggctcc cggcgcggcg gcggaggggg cgggcaggcc ggcgggcggt | 120 |
| gatgtggcgg gactctttat gcgctgcggc aggatacgcg ctcggcgctg ggacgcgact | 180 |
| gcgctcagtt ctctcctctc ggaagctgca gccatgatgg aagtttgaga gttgagccgc | 240 |
| tgtgaggcga ggccgggctc aggcgaggga gatgagagac ggcggcggcc gcggcccgga | 300 |
| gcccctctca gcgcctgtga gcagccgcgg gggcagcgcc ctcggggagc cggccggcct | 360 |
| gcggcggcgg cagcggcggc gtttctcgcc tcctcttcgt cttttctaac cgtgcagcct | 420 |
| cttcctcggc ttctcctgaa agggaaggtg gaagccgtgg gctcgggcgg gagccggctg | 480 |
| aggcgcggcg gcggcggcgg cacctcccgc tcctggagcg gggggagaa gcggcggcgg | 540 |
| cggcggccgc ggcggctgca gctccaggga gggggtctga gtcgcctgtc accatttcca | 600 |
| gggctgggaa cgccggagag ttggtctctc cccttctact gcctccaaca cggcggcggc | 660 |
| ggcggcggca catccaggga cccgggccgg ttttaaacct cccgtccgcc gccgccgcac | 720 |
| cccccgtggc ccgggctccg gaggccgccg gcggaggcag ccgttcggag gattattcgt | 780 |
| cttctccca ttccgctgcc gccgctgcca ggcctctggc tgctgaggag aagcaggcc | 840 |
| agtcgctgca accatccagc agccgccgca gcagccatta cccggctgcg gtccagagcc | 900 |
| aagcggcgg agagcgaggg gcatcagcta ccgccaagtc cagagccatt tccatcctgc | 960 |
| agaagaagcc ccgccaccag cagcttctgc catctctctc ctccttttc ttcagccaca | 1020 |
| ggctcccaga catgacagcc atcatcaaag agatcgttag cagaaacaaa aggagatatc | 1080 |
| aagaggatgg attcgactta gacttgacct atatttatcc aaacattatt gctatgggat | 1140 |
| ttcctgcaga aagacttgaa ggcgtataca ggaacaatat tgatgatgta gtaaggtttt | 1200 |
| tggattcaaa gcataaaaac cattacaaga tatacaatct ttgtgctgaa agacattatg | 1260 |
| acaccgccaa atttaattgc agagttgcac aatatccttt tgaagaccat aacccaccac | 1320 |

-continued

```
agctagaact tatcaaaccc ttttgtgaag atcttgacca atggctaagt gaagatgaca    1380
atcatgttgc agcaattcac tgtaaagctg gaaagggacg aactggtgta atgatatgtg    1440
catatttatt acatcggggc aaatttttaa aggcacaaga ggccctagat ttctatgggg    1500
aagtaaggac cagagacaaa aagggagtaa ctattcccag tcagaggcgc tatgtgtatt    1560
attatagcta cctgttaaag aatcatctgg attatagacc agtggcactg ttgtttcaca    1620
agatgatgtt tgaaactatt ccaatgttca gtggcggaac ttgcaatcct cagtttgtgg    1680
tctgccagct aaaggtgaag atatattcct ccaattcagg acccacacga cgggaagaca    1740
agttcatgta ctttgagttc cctcagccgt tacctgtgtg tggtgatatc aaagtagagt    1800
tcttccacaa acagaacaag atgctaaaaa aggacaaaat gtttcacttt tgggtaaata    1860
cattcttcat accaggacca gaggaaacct cagaaaagt agaaaatgga agtctatgtg    1920
atcaagaaat cgatagcatt tgcagtatag agcgtgcaga taatgacaag gaatatctag    1980
tacttacttt aacaaaaaat gatcttgaca aagcaaataa agacaaagcc aaccgatact    2040
tttctccaaa ttttaaggtg aagctgtact tcacaaaaac agtagaggag ccgtcaaatc    2100
cagaggctag cagttcaact tctgtaacac cagatgttag tgacaatgaa cctgatcatt    2160
atagatattc tgcaccact gactctgatc cagagaatga accttttgat gaagatcagc    2220
atacacaaat tacaaaagtc tgaattttttt tttatcaaga gggataaaac accatgaaaa    2280
taaacttgaa taaactgaaa atggaccttt ttttttttaa tggcaatagg acattgtgtc    2340
agattaccag ttataggaac aattctcttt tcctgaccaa tcttgtttta ccctatacat    2400
ccacagggtt ttgacacttg ttgtccagtt gaaaaaggt tgtgtagctg tgtcatgtat    2460
ataccttttt gtgtcaaaag gacatttaaa attcaattag gattaataaa gatggcactt    2520
tcccgtttta ttccagtttt ataaaaagtg gagacagact gatgtgtata cgtaggaatt    2580 ttttccttt gtgttctgtc accaactgaa gtggctaaag gctttgtga tatactggtt    2640 cacatcctac ccctttgcac ttgtggcaac agataagttt gcagttggct aagagaggtt    2700
tccgaagggt tttgctacat tctaatgcat gtattcgggt taggggaatg gagggaatgc    2760
tcagaaagga aataattta tgctggactc tggaccatat accatctcca gctatttaca    2820
cacacctttc tttagcatgc tacagttatt aatctggaca ttcgaggaat tggccgctgt    2880
cactgcttgt tgtttgcgca ttttttttta aagcatattg gtgctagaaa aggcagctaa    2940
aggaagtgaa tctgtattgg ggtacaggaa tgaaccttct gcaacatctt aagatccaca    3000
aatgaaggga tataaaaata atgtcatagg taagaaacac agcaacaatg acttaaccat    3060
ataaatgtgg aggctatcaa caaagaatgg gcttgaaaca ttataaaaat tgacaatgat    3120
ttattaaata tgttttctca attgtaacga cttctccatc tcctgtgtaa tcaaggccag    3180
tgctaaaatt cagatgctgt tagtacctac atcagtcaac aacttacact tattttacta    3240
gttttcaatc ataatacctg ctgtggatgc ttcatgtgct gcctgcaagc ttcttttttc    3300
tcattaaata taaatatttt tgtaatgctg cacagaaatt ttcaatttga gattctacag    3360
taagcgtttt ttttctttga agatttatga tgcacttatt caatagctgt cagccgttcc    3420
acccttttga ccttacacat tctattacaa tgaattttgc agttttgcac attttttaaa    3480
tgtcattaac tgttagggaa ttttacttga atactgaata catataatgt ttatattaaa    3540
aaggacattt gtgttaaaaa ggaaattaga gttgcagtaa actttcaatg ctgcacacaa    3600 aaaaagaca tttgattttt cagtagaaat tgtcctacat gtgctttatt gatttgctat    3660
tgaaagaata gggttttttt tttttttttt ttttttttt ttaaatgtgc agtgttgaat    3720
```

```
catttcttca tagtgctccc ccgagttggg actagggctt caatttcact tcttaaaaaa    3780
aatcatcata tatttgatat gcccagactg catacgattt taagcggagt acaactacta    3840
ttgtaaagct aatgtgaaga tattattaaa aaggttttt tttccagaaa tttggtgtct     3900
tcaaattata ccttcacctt gacatttgaa tatccagcca ttttgtttct taatggtata    3960
aaattccatt ttcaataact tattggtgct gaaattgttc actagctgtg gtctgaccta    4020
gttaatttac aaatacagat tgaataggac ctactagagc agcatttata gagttttgatg   4080
gcaaatagat taggcagaac ttcatctaaa atattcttag taaataatgt tgacacgttt    4140
tccatacctt gtcagtttca ttcaacaatt tttaaatttt taacaaagct cttaggattt    4200
acacatttat atttaaacat tgatatatag agtattgatt gattgctcat aagttaaatt    4260
ggtaaagtta gagacaacta ttctaacacc tcaccattga aatttatatg ccaccttgtc    4320
tttcataaaa gctgaaaatt gttacctaaa atgaaaatca acttcatgtt ttgaagatag    4380
ttataaatat tgttctttgt tacaatttcg ggcaccgcat attaaaacgt aactttattg    4440
ttccaatatg taacatggag ggccaggtca taaataatga cattataatg gcttttgca     4500
ctgttattat ttttcctttg gaatgtgaag gtctgaatga gggttttgat tttgaatgtt    4560
tcaatgtttt tgagaagcct tgcttacatt ttatggtgta gtcattggaa atggaaaaat    4620
ggcattatat atattatata tataaatata tattatacat actctcctta ctttatttca    4680
gttaccatcc ccatagaatt tgacaagaat tgctatgact gaaaggtttt cgagtcctaa    4740
ttaaaacttt atttatggca gtattcataa ttagcctgaa atgcattctg taggtaatct    4800
ctgagtttct ggaatatttt cttagacttt ttggatgtgc agcagcttac atgtctgaag    4860
ttacttgaag gcatcacttt taagaaagct tacagttggg ccctgtacca tcccaagtcc    4920
tttgtagctc ctcttgaaca tgtttgccat acttttaaaa gggtagttga ataaatagca    4980
tcaccattct ttgctgtggc acaggttata aacttaagtg gagtttaccg gcagcatcaa    5040
atgtttcagc tttaaaaaat aaaagtaggg tacaagttta atgtttagtt ctagaaattt    5100
tgtgcaatat gttcataacg atggctgtgg ttgccacaaa gtgcctcgtt tacctttaaa    5160
tactgttaat gtgtcatgca tgcagatgga aggggtggaa ctgtgcacta aagtggggggc   5220
tttaactgta gtatttggca gagttgcctt ctacctgcca gttcaaaagt tcaacctgtt    5280
ttcatataga atatatatac taaaaaattt cagtctgtta aacagcctta ctctgattca    5340
gcctcttcag atactcttgt gctgtgcagc agtggctctg tgtgtaaatg ctatgcactg    5400
aggatacaca aaaataccaa tatgatgtgt acaggataat gcctcatccc aatcagatgt    5460
ccatttgtta ttgtgtttgt taacaaccct ttatctctta gtgttataaa ctccacttaa    5520
aactgattaa agtctcattc ttgtcaaaaa aaaaaaaaaa aaaaaaaaaa aa            5572
```

<210> SEQ ID NO 6
<211> LENGTH: 2222
<212> TYPE: DNA
<213> ORGANISM: Homo sapiens

<400> SEQUENCE: 6

```
attcggcacg agggaggaag cgagaggtgc tgccctcccc ccggagttgg aagcgcgtta     60
cccgggtcca aaatgcccaa gaagaagccg acgcccatcc agctgaaccc ggcccccgac    120
ggctctgcag ttaacgggac cagtctgcgg gagaccaact tggaggcctt gcagaagaag    180
ctggaggagc tagagcttga tgagcagcag cgaaagcgcc ttgaggcctt tcttacccag    240
```
aagcagaagg tgggagaact gaaggatgac gactttgaga agatcagtga gctgggggct        300
ggcaatggcg gtgtggtgtt caaggtctcc cacaagcctt ctggcctggt catggccaga        360
aagctaattc atctggagat caaacccgca atccggaacc agatcataag ggagctgcag        420
gttctgcatg agtgcaactc tccgtacatc gtgggcttct atggtgcgtt ctacagcgat        480
ggcgagatca gtatctgcat ggagcacatg gatggaggtt ctctggatca agtcctgaag        540
aaagctggaa gaattcctga acaaattta ggaaaagtta gcattgctgt aataaaaggc         600
ctgacatatc tgagggagaa gcacaagatc atgcacagag atgtcaagcc ctccaacatc        660
ctagtcaact cccgtgggga gatcaagctc tgtgactttg gggtcagcgg gcagctcatc        720
gactccatgg ccaactcctt cgtgggcaca aggtcctaca tgtcgccaga aagactccag        780
gggactcatt actctgtgca gtcagacatc tggagcatgg gactgtctct ggtagagatg        840
gcggttggga ggtatcccat ccctcctcca gatgccaagg agctggagct gatgtttggg        900
tgccaggtgg aaggagatgc ggctgagacc ccacccaggc caaggacccc cgggaggccc        960
cttagctcat acggaatgga cagccgacct cccatggcaa ttttgagtt gttggattac        1020 atagtcaacg agcctcctcc aaaactgccc agtggagtgt tcagtctgga atttcaagat       1080
tttgtgaata atgcttaat aaaaaacccc gcagagagag cagatttgaa gcaactcatg        1140
gttcatgctt ttatcaagag atctgatgct gaggaagtgg attttgcagg ttggctctgc       1200
tccaccatcg gccttaacca gcccagcaca ccaacccatg ctgctggcgt ctaagtgttt       1260
gggaagcaac aaagagcgag tccctgccc ggtggtttgc catgtcgctt ttgggcctcc        1320
ttcccatgcc tgtctctgtt cagatgtgca tttcacctgt gacaaaggat gaagaacaca       1380
gcatgtgcca agattctact cttgtcattt taatattac tgtctttatt cttattacta        1440
ttattgttcc cctaagtgga ttggctttgt gcttggggct atttgtgtgt atgctgatga       1500
tcaaaacctg tgccaggctg aattacagtg aaattttgg tgaatgtggg tagtcattct        1560
tacaattgca ctgctgttcc tgctccatga ctggctgtct gcctgtattt tcggactttg      1620
acatttgaca tttggtggac tttatcttgc tgggcatact ttctctctag agggagcct       1680 tgtgagatcc ttcacaggca gtgcatgtga agcatgcttt gctgctatga aaatgagcat      1740
cagagagtgt acatcatgtt attttattat tattatttgc ttttcatgta gaactcagca     1800
gttgacatcc aaatctagcc agagcccttc actgccatga tagctggggc ttcaccagtc     1860
tgtctactgt ggtgatctgt agacttctgg ttgtatttct atatttattt tcagtatact      1920
gtgtgggata cttagtggta tgtctcttta agttttgatt aatgtttctt aaatggaatt      1980
atttgaatgt cacaaattga tcaagatatt aaaatgtcgg atttatcttt ccccatatcc     2040
aagtaccaat gctgttgtaa acaacgtgta tagtgcctaa aattgtatga aaatccttt       2100 aaccatttta acctagatgt ttaacaaatc taatctctta ttctaataaa tatactatga     2160
aataaaaaaa aaaggagaaa gctaaaaaaa aaaaaaaaa aaaaaaaaa aaaaaaaaa          2220 aa                                                                      2222

<210> SEQ ID NO 7
<211> LENGTH: 5916
<212> TYPE: DNA
<213> ORGANISM: Homo sapiens

<400> SEQUENCE: 7
gcccctccct ccgcccgccc gccggcccgc ccgtcagtct ggcaggcagg caggcaatcg         60
gtccgagtgg ctgtcggctc ttcagctctc ccgctcggcg tcttccttcc tcctcccggt       120

```
cagcgtcggc ggctgcaccg gcggcggcgc agtccctgcg ggaggggcga caagagctga    180
gcggcggccg ccgagcgtcg agctcagcgc ggcggaggcg gcggcggccc ggcagccaac    240
atggcggcgg cggcggcggc gggcgcgggc ccggagatgg tccgcgggca ggtgttcgac    300
gtggggccgc gctacaccaa cctctcgtac atcggcgagg gcgcctacgg catggtgtgc    360
tctgcttatg ataatgtcaa caaagttcga gtagctatca agaaaatcag ccccttgag     420 caccagacct actgccagag aaccctgagg gagataaaaa tcttactgcg cttcagacat    480
gagaacatca ttggaatcaa tgacattatt cgagcaccaa ccatcgagca atgaaagat    540 gtatatatag tacaggacct catggaaaca gatctttaca agctcttgaa gacacaaacac   600 ctcagcaatg accatatctg ctattttctc taccagatcc tcagagggtt aaaatatatc    660
cattcagcta acgttctgca ccgtgacctc aagccttcca acctgctgct caacaccacc    720
tgtgatctca agatctgtga ctttggcctg gcccgtgttg cagatccaga ccatgatcac    780
acagggttcc tgacagaata tgtggccaca cgttggtaca gggctccaga aattatgttg    840
aattccaagg gctacaccaa gtccattgat atttggtctg taggctgcat tctggcagaa    900
atgctttcta acaggcccat ctttccaggg aagcattatc ttgaccagct gaaccacatt    960
ttgggtattc ttggatcccc atcacaagaa gacctgaatt gtataataaa tttaaaagct   1020
aggaactatt tgctttctct tccacacaaa aataaggtgc catggaacag gctgttccca   1080
aatgctgact ccaaagctct ggacttattg gacaaaatgt tgacattcaa cccacacaag   1140
aggattgaag tagaacaggc tctggcccac ccatatctgg agcagtatta cgacccgagt   1200
gacgagccca tcgccgaagc accattcaag ttcgacatgg aattggatga cttgcctaag   1260
gaaaagctca agaactaatt tttgaagag actgctagat ccagccagg atacagatct    1320 taaatttgtc aggacaaggg ctcagaggac tggacgtgct cagacatcgg tgttcttctt   1380
cccagttctt gacccctggt cctgtctcca gcccgtcttg gcttatccac tttgactcct   1440
ttgagccgtt tggaggggcg gtttctggta gttgtggctt ttatgctttc aaagaatttc   1500
ttcagtccag agaattcctc ctggcagccc tgtgtgtgtc acccattggt gacctgcggc   1560
agtatgtact tcagtgcacc tactgcttac tgttgcttta gtcactaatt gctttctggt   1620
ttgaaagatg cagtggttcc tccctctcct gaatcctttt ctacatgatg ccctgctgac   1680
catgcagccg caccagagag agattcttcc ccaattggct ctagtcactg gcatctcact   1740
ttatgatagg gaaggctact acctagggca ctttaagtca gtgacagccc cttatttgca   1800
cttcaccttt tgaccataac tgtttcccca gagcaggagc ttgtggaaat accttggctg   1860
atgttgcagc ctgcagcaag tgcttccgtc tccggaatcc ttggggagca cttgtccacg   1920
tcttttctca tatcatggta gtcactaaca tatataaggt atgtgctatt ggcccagctt   1980
ttagaaaatg cagtcatttt tctaaataaa aaggaagtac tgcacccagc agtgtcactc   2040
tgtagttact gtggtcactt gtaccatata gaggtgtaac acttgtcaag aagcgttatg   2100
tgcagtactt aatgtttgta agacttacaa aaaaagattt aaagtggcag cttcactcga   2160
catttggtga gagaagtaca aaggttgcag tgctgagctg tgggcggttt ctggggatgt   2220
cccagggtgg aactccacat gctggtgcat atacgccctt gagctacttc aaatgtgggt   2280
gtttcagtaa ccacgttcca tgcctgagga tttagcagag aggaacactg cgtctttaaa   2340
tgagaaagta tacaattctt tttccttcta cagcatgtca gcatctcaag ttcattttc    2400 aacctacagt ataacaattt gtaataaagc ctccaggagc tcatgacgtg aagcactgtt   2460
```

```
ctgtcctcaa gtactcaaat atttctgata ctgctgagtc agactgtcag aaaaagctag   2520
cactaactcg tgtttggagc tctatccata ttttactgat ctctttaagt atttgttcct   2580
gccactgtgt actgtggagt tgactcggtg ttctgtccca gtgcggtgcc tcctcttgac   2640
ttccccactg ctctctgtgg tgagaaattt gccttgttca ataattactg taccctcgca   2700
tgactgttac agctttctgt gcagagatga ctgtccaagt gccacatgcc tacgattgaa   2760
atgaaaactc tattgttacc tctgagttgt gttccacgga aaatgctatc cagcagatca   2820
tttaggaaaa ataattctat ttttagcttt tcatttctca gctgtccttt tttcttgttt   2880 gattttttgac agcaatggag aatgggttat ataaagactg cctgctaata tgaacagaaa   2940
tgcatttgta attcatgaaa ataaatgtac atcttctatc ttcacattca tgttaagatt   3000
cagtgttgct ttcctctgga tcagcgtgtc tgaatggaca gtcaggttca ggttgtgctg   3060
aacacagaaa tgctcacagg cctcactttg ccgcccaggc actggcccag cacttggatt   3120
tacataagat gagttagaaa ggtacttctg tagggtcctt tttacctctg ctcggcagag   3180
aatcgatgct gtcatgttcc tttattcaca atcttaggtc tcaaatattc tgtcaaaccc   3240
taacaaagaa gccccgacat ctcaggttgg attccctggt tctctctaaa gagggcctgc   3300
ccttgtgccc cagaggtgct gctgggcaca gccaagagtt gggaagggcc gccccacagt   3360
acgcagtcct caccacccag cccagggtgc tcacgctcac cactcctgtg gctgaggaag   3420
gatagctggc tcatcctcgg aaaacagacc cacatctcta ttcttgccct gaaatacgcg   3480
cttttcactt gcgtgctcag agctgccgtc tgaaggtcca cacagcattg acgggacaca   3540
gaaatgtgac tgttaccgga taacactgat tagtcagttt tcatttataa aaaagcattg   3600
acagttttat tactcttgtt tcttttttaaa tggaaagtta ctattataag gttaatttgg   3660
agtcctcttc taaatagaaa accatatcct tggctactaa catctggaga ctgtgagctc   3720
cttcccattc cccttcctgg tactgtggag tcagattggc atgaaaccac taacttcatt   3780
ctagaatcat tgtagccata agttgtgtgc tttttattaa tcatgccaaa cataatgtaa   3840
ctgggcagag aatggtccta accaaggtac ctatgaaaag cgctagctat catgtgtagt   3900
agatgcatca ttttggctct tcttacattt gtaaaaatgt acagattagg tcatcttaat   3960
tcatattagt gacacggaac agcacctcca ctatttgtat gttcaaataa gctttcagac   4020
taatagcttt tttggtgtct aaaatgtaag caaaaaattc ctgctgaaac attccagtcc   4080
tttcatttag tataaaagaa atactgaaca agccagtggg atggaattga agaactaat   4140 catgaggact ctgtcctgac acaggtcctc aaagctagca gagatacgca gacattgtgg   4200
catctgggta gaagaatact gtattgtgtg tgcagtgcac agtgtgtggt gtgtgcacac   4260
tcattccttc tgctcttggg cacaggcagt gggtgtagag gtaaccagta gctttgagaa   4320
gctacatgta gctcaccagt ggttttctct aaggaatcac aaaagtaaac tacccaacca   4380
catgccacgt aatatttcag ccattcagag gaaactgttt tctctttatt tgcttatatg   4440
ttaatatggt ttttaaattg gtaactttta tatagtatgg taacagtatg ttaatacaca   4500
catacatacg cacacatgct ttgggtcctt ccataatact tttatatttg taaatcaatg   4560
ttttggagca atcccaagtt taagggaaat attttttgtaa atgtaatggt tttgaaaatc   4620
tgagcaatcc ttttgcttat acatttttaa agcatttgtg ctttaaaatt gttatgctgg   4680
tgtttgaaac atgatactcc tgtggtgcag atgagaagct ataacagtga atatgtggtt   4740
tctcttacgt catccacctt gacatgatgg gtcagaaaca aatggaaatc cagagcaagt   4800
cctccagggt tgcaccaggt ttacctaaag cttgttgcct tttcttgtgc tgtttatgcg   4860
```

```
tgtagagcac tcaagaaagt tctgaaactg ctttgtatct gctttgtact gttggtgcct    4920
tcttggtatt gtaccccaaa attctgcata gattatttag tataatggta agttaaaaaa    4980
tgttaaagga agattttatt aagaatctga atgtttattc attatattgt tacaatttaa    5040
cattaacatt tatttgtggt atttgtgatt tggttaatct gtataaaaat tgtaagtaga    5100
aaggtttata tttcatctta attcttttga tgttgtaaac gtacttttta aaagatggat    5160
tatttgaatg tttatggcac ctgacttgta aaaaaaaaa actacaaaaa aatccttaga    5220
atcattaaat tgtgtccctg tattaccaaa ataacacagc accgtgcatg tatagtttaa    5280
ttgcagtttc atctgtgaaa acgtgaaatt gtctagtcct tcgttatgtt ccccagatgt    5340
cttccagatt tgctctgcat gtggtaactt gtgttagggc tgtgagctgt tcctcgagtt    5400
gaatggggat gtcagtgctc ctagggttct ccaggtggtt cttcagacct tcacctgtgg    5460 ggggggggt aggcggtgcc cacgcccatc tcctcatcct cctgaacttc tgcaacccca    5520
ctgctgggca gacatcctgg gcaaccccctt ttttcagagc aagaagtcat aaagatagga    5580
tttcttggac atttggttct tatcaatatt gggcattatg taatgactta tttacaaaac    5640
aaagatactg gaaaatgttt tggatgtggt gttatggaaa gagcacaggc cttggaccca    5700
tccagctggg ttcagaacta ccccctgctt ataactgcgg ctggctgtgg gccagtcatt    5760
ctgcgtctct gctttcttcc tctgcttcag actgtcagct gtaaagtgga agcaatatta    5820
cttgccttgt atatggtaaa gattataaaa atacatttca actgttcagc atagtacttc    5880
aaagcaagta ctcagtaaat agcaagtctt tttaaa                              5916
```

<210> SEQ ID NO 8
<211> LENGTH: 2230
<212> TYPE: DNA
<213> ORGANISM: Homo sapiens

<400> SEQUENCE: 8

```
cttggagaca acatgtggtt cttgacaact ctgctccttt gggttccagt tgatgggcaa      60
gtggacacca caaaggcagt gatcactttg cagcctccat gggtcagcgt gttccaagag    120
gaaaccgtaa ccttgcattg tgaggtgctc catctgcctg ggagcagctc tacacagtgg    180 ttttctcaatg gcacagccac tcagacctcg accccccagct acagaatcac ctctgccagt    240
gtcaatgaca gtggtgaata caggtgccag agaggtctct cagggcgaag tgaccccata    300
cagctggaaa tccacagagg ctggctacta ctgcaggtct ccagcagagt cttcacggaa    360 ggagaaccctc tggccttgag gtgtcatgcg tggaaggata agctggtgta caatgtgctt    420
tactatcgaa atggcaaagc ctttaagttt ttccactgga attctaacct caccattctg    480
aaaaccaaca taagtcacaa tggcacctac cattgctcag gcatgggaaa gcatcgctac    540
acatcagcag gaatatctgt cactgtgaaa gagctatttc cagctccagt gctgaatgca    600
tctgtgacat ccccactcct ggaggggaat ctggtcaccc tgagctgtga aacaaagttg    660
ctcttgcaga ggcctggttt gcagctttac ttctcctttc acatgggcag caagaccctg    720
cgaggcagga acatcctctc tgaataccaa atactaactg ctagaagaga agactctggg    780
ttatactggt gcgaggctgc cacagaggat ggaaatgtcc ttaagcgcag ccctgagttg    840
gagcttcaag tgcttggcct ccagttacca actcctgtct ggtttcatgt cctttttctat    900 ctggcagtgg gaataatgtt tttagtgaac actgttctct gggtgacaat acgtaaagaa    960
ctgaaaagaa agaaaaagtg ggatttagaa atctctttgg attctggtca tgagaagaag   1020
```

| | |
|---|---|
| gtaatttcca gccttcaaga agacagacat ttagaagaag agctgaaatg tcaggaacaa | 1080 |
| aaagaagaac agctgcagga aggggtgcac cggaaggagc cccagggggc cacgtagcag | 1140 |
| cggctcagtg ggtggccatc gatctggacc gtcccctgcc cacttgctcc ccgtgagcac | 1200 |
| tgcgtacaaa catccaaaag ttcaacaaca ccagaactgt gtgtctcatg gtatgtaact | 1260 |
| cttaaagcaa ataaatgaac tgacttcaac tgggatacat ttggaaatgt ggtcatcaaa | 1320 |
| gatgacttga atgaggcct actctaaaga attcttgaaa aacttacaag tcaagcctag | 1380 |
| cctgataatc ctattacata gtttgaaaaa tagtatttta tttctcagaa caaggtaaaa | 1440 |
| aggtgagtgg gtgcatatgt acagaagatt aagacagaga acagacaga agagacaca | 1500 |
| cacacagcca ggagtgggta gatttcaggg agacaagagg gaatagtata gacaataagg | 1560 |
| aaggaaatag tacttacaaa tgactcctaa gggactgtga gactgagagg gctcacgcct | 1620 |
| ctgtgttcag gatacttagt tcatggcttt tctctttgac tttactaaaa gagaatgtct | 1680 |
| ccatacgcgt tctaggcata caaggggta actcatgatg agaaatggat gtgttattct | 1740 |
| tgccctctct tttgaggctc tctcataacc cctctatttc tagagacaac aaaaatgctg | 1800 |
| ccagtcctag gcccctgccc tgtaggaagg cagaatgtaa ctgttctgtt tgtttaacga | 1860 |
| ttaagtccaa atctccaagt gcggcactgc aaagagacgc ttcaagtggg gagaagcggc | 1920 |
| gataccatag agtccagatc ttgcctccag agatttgctt taccttcctg attttctggt | 1980 |
| tactaattag cttcaggata cgctgctctc atacttgggc tgtagtttgg agacaaaata | 2040 |
| ttttcctgcc actgtgtaac atagctgagg taaaaactga actatgtaaa tgactctact | 2100 |
| aaaagtttag ggaaaaaaaa caggaggagt atgcacaaa aaaaaaaaa aaaaaaaaa | 2160 |
| aaaaaaaaaa aaaaaaaaa aaaaaaaaa aaaaaaaaa aaaaaaaaa aaaaaaaaa | 2220 |
| aaaaaaaaaa | 2230 |

<210> SEQ ID NO 9
<211> LENGTH: 5616
<212> TYPE: DNA
<213> ORGANISM: Homo sapiens

<400> SEQUENCE: 9

| | |
|---|---|
| ccccggcgca gcgcggccgc agcagcctcc gccccccgca cggtgtgagc gcccgacgcg | 60 |
| gccgaggcgg ccggagtccc gagctagccc cggcggccgc cgccgcccag accgacgac | 120 |
| aggccacctc gtcggcgtcc gcccgagtcc ccgcctcgcc gccaacgcca caaccaccgc | 180 |
| gcacggcccc ctgactccgt ccagtattga tcggagagc cggagcgagc tcttcgggga | 240 |
| gcagcgatgc gaccctccgg gacggccggg gcagcgctcc tggcgctgct ggctgcgctc | 300 |
| tgcccggcga gtcgggctct ggaggaaaag aaagtttgcc aaggcacgag taacaagctc | 360 |
| acgcagttgg gcacttttga agatcatttt ctcagcctcc agaggatgtt caataactgt | 420 |
| gaggtggtcc ttgggaattt ggaaattacc tatgtgcaga ggaattatga tctttccttc | 480 |
| ttaaagacca tccaggaggt ggctggttat gtcctcattg ccctcaacac agtggagcga | 540 |
| attcctttgg aaaacctgca gatcatcaga ggaaatatgt actacgaaaa ttcctatgcc | 600 |
| ttagcagtct tatctaacta tgatgcaaat aaaaccggac tgaaggagct gcccatgaga | 660 |
| aatttacagg aaatcctgca tggcgccgtg cggttcagca acaaccctgc cctgtgcaac | 720 |
| gtggagagca tccagtggcg ggacatagtc agcagtgact ttctcagcaa catgtcgatg | 780 |
| gacttccaga accaccctgg gcagctgcca agtgtgatc caagctgtcc caatgggagc | 840 |
| tgctggggtg caggagagga gaactgccag aaactgacca aaatcatctg tgcccagcag | 900 |

-continued

| | |
|---|---|
| tgctccgggc gctgccgtgg caagtccccc agtgactgct gccacaacca gtgtgctgca | 960 |
| ggctgcacag gcccccggga gagcgactgc ctggtctgcc gcaaattccg agacgaagcc | 1020 |
| acgtgcaagg acacctgccc cccactcatg ctctacaacc ccaccacgta ccagatggat | 1080 |
| gtgaaccccg agggcaaata cagctttggt gccacctgcg tgaagaagtg tcccgtaat | 1140 |
| tatgtggtga cagatcacgg ctcgtgcgtc cgagcctgtg gggccgacag ctatgagatg | 1200 |
| gaggaagacg gcgtccgcaa gtgtaagaag tgcgaagggc cttgccgcaa agtgtgtaac | 1260 |
| ggaataggta ttggtgaatt taaagactca ctctccataa atgctacgaa tattaaacac | 1320 |
| ttcaaaaact gcacctccat cagtggcgat ctccacatcc tgccggtggc atttaggggt | 1380 |
| gactccttca cacatactcc tcctctggat ccacaggaac tggatattct gaaaaccgta | 1440 |
| aaggaaatca cagggttttt gctgattcag gcttggcctg aaaacaggac ggacctccat | 1500 |
| gcctttgaga acctagaaat catacgcggc aggaccaagc aacatggtca gttttctctt | 1560 |
| gcagtcgtca gcctgaacat aacatccttg ggattacgct ccctcaagga gataagtgat | 1620 |
| ggagatgtga taatttcagg aaacaaaaat ttgtgctatg caaatacaat aaactggaaa | 1680 |
| aaactgtttg gaacctccgg tcagaaaacc aaaattataa gcaacagagg tgaaaacagc | 1740 |
| tgcaaggcca caggccaggt ctgccatgcc ttgtgctccc ccgagggctg ctggggcccg | 1800 |
| gagcccaggg actgcgtctc ttgccggaat gtcagccgag gcaggaatg cgtggacaag | 1860 |
| tgcaaccttc tggagggtga gccaagggag tttgtggaga actctgagtg catacagtgc | 1920 |
| cacccagagt gcctgcctca ggccatgaac atcacctgca caggacgggg accagacaac | 1980 |
| tgtatccagt gtgcccacta cattgacggc ccccactgcg tcaagacctg cccggcagga | 2040 |
| gtcatgggag aaaacaacac cctggtctgg aagtacgcag acgccggcca tgtgtgccac | 2100 |
| ctgtgccatc caaactgcac ctacggatgc actgggccag tcttgaagg ctgtccaacg | 2160 |
| aatgggccta agatcccgtc catcgccact gggatggtgg gggccctcct cttgctgctg | 2220 |
| gtggtggccc tggggatcgg cctcttcatg cgaaggcgcc acatcgttcg gaagcgcacg | 2280 |
| ctgcggaggc tgctgcagga gagggagctt gtggagcctc ttacacccag tggagaagct | 2340 |
| cccaaccaag ctctcttgag gatcttgaag gaaactgaat tcaaaaagat caagtgctg | 2400 |
| ggctccggtg cgttcggcac ggtgtataag ggactctgga tcccagaagg tgagaaagtt | 2460 |
| aaaattcccg tcgctatcaa ggaattaaga gaagcaacat ctccgaaagc caacaaggaa | 2520 |
| atcctcgatg aagcctacgt gatggccagc gtggacaacc cccacgtgtg ccgcctgctg | 2580 |
| ggcatctgcc tcacctccac cgtgcagctc atcacgcagc tcatgccctt cggctgcctc | 2640 |
| ctggactatg tccgggaaca caaagacaat attggctccc agtacctgct caactggtgt | 2700 |
| gtgcagatca caagggcat gaactacttg gaggaccgtc gcttggtgca ccgcgacctg | 2760 |
| gcagccagga acgtactggt gaaaacaccg cagcatgtca agatcacaga ttttgggctg | 2820 |
| gccaaactgc tgggtgcgga agagaaagaa taccatgcag aaggaggcaa agtgcctatc | 2880 |
| aagtggatgg cattggaatc aattttacac agaatctata cccaccagag tgatgtctgg | 2940 |
| agctacgggg tgaccgtttg ggagttgatg accttggat ccaagccata tgacggaatc | 3000 |
| cctgccagcg agatctcctc catcctggag aaaggagaac gctccctca gccacccata | 3060 |
| tgtaccatcg atgtctacat gatcatggtc aagtgctgga tgatagacgc agatagtcgc | 3120 |
| ccaaagttcc gtgagttgat catcgaattc tccaaaatgg cccgagaccc ccagcgctac | 3180 |
| cttgtcattc aggggatga agaatgcat ttgccaagtc ctacagactc caacttctac | 3240 |

```
cgtgccctga tggatgaaga agacatggac gacgtggtgg atgccgacga gtacctcatc      3300
ccacagcagg gcttcttcag cagcccctcc acgtcacgga ctcccctcct gagctctctg      3360
agtgcaacca gcaacaattc caccgtggct tgcattgata gaaatgggct gcaaagctgt      3420
cccatcaagg aagacagctt cttgcagcga tacagctcag accccacagg cgccttgact      3480
gaggacagca tagacgacac cttcctccca gtgcctgaat acataaacca gtccgttccc      3540
aaaaggcccg ctggctctgt gcagaatcct gtctatcaca atcagcctct gaaccccgcg      3600
cccagcagag acccacacta ccaggacccc cacagcactg cagtgggcaa cccgagtat       3660 ctcaacactg tccagcccac ctgtgtcaac agcacattcg acagccctgc ccactgggcc      3720
cagaaaggca gccaccaaat tagcctggac aaccctgact accagcagga cttctttccc      3780
aaggaagcca agccaaatgg catctttaag ggctccacag ctgaaaatgc agaataccta      3840
agggtcgcgc cacaaagcag tgaatttatt ggagcatgac cacggaggat agtatgagcc      3900
ctaaaaatcc agactctttc gatacccagg accagccac agcaggtcct ccatcccaac       3960
agccatgccc gcattagctc ttagacccac agactggttt tgcaacgttt acaccgacta      4020
gccaggaagt acttccacct cgggcacatt ttgggaagtt gcattccttt gtcttcaaac      4080
tgtgaagcat ttacagaaac gcatccagca agaatattgt ccctttgagc agaaatttat      4140
ctttcaaaga ggtatatttg aaaaaaaaaa aaagtatatg tgaggatttt tattgattgg      4200
ggatcttgga gttttcatt gtcgctattg attttactt caatgggctc ttccaacaag        4260
gaagaagctt gctggtagca cttgctaccc tgagttcatc caggcccaac tgtgagcaag      4320
gagcacaagc cacaagtctt ccagaggatg cttgattcca gtggttctgc ttcaaggctt      4380
ccactgcaaa acactaaaga tccaagaagg ccttcatggc cccagcaggc cggatcggta      4440
ctgtatcaag tcatggcagg tacagtagga taagccactc tgtcccttcc tgggcaaaga      4500
agaaacggag gggatggaat tcttccttag acttactttt gtaaaaatgt ccccacggta      4560
cttactcccc actgatggac cagtggtttc cagtcatgag cgttagactg acttgtttgt      4620
cttccattcc attgttttga aactcagtat gctgcccctg tcttgctgtc atgaaatcag      4680
caagagagga tgacacatca ataataact cggattccag cccacattgg attcatcagc       4740
atttggacca atagcccaca gctgagaatg tggaatacct aaggatagca ccgcttttgt      4800
tctcgcaaaa acgtatctcc taatttgagg ctcagatgaa atgcatcagg tcctttgggg      4860
catagatcag aagactacaa aaatgaagct gctctgaaat ctcctttagc catcaccca        4920 accccccaaa attagtttgt gttacttatg aagatagtt ttctcctttt acttcacttc       4980
aaaagctttt tactcaaaga gtatatgttc cctccaggtc agctgccccc aaaccccctc      5040
cttacgcttt gtcacacaaa aagtgtctct gccttgagtc atctattcaa gcacttacag      5100
ctctggccac aacagggcat tttacaggtg cgaatgacag tagcattatg agtagtgtgg      5160
aattcaggta gtaaatatga aactagggtt tgaaattgat aatgctttca caacatttgc      5220
agatgtttta gaaggaaaaa agttccttcc taaaataatt tctctacaat tggaagattg      5280
gaagattcag ctagttagga gcccacctt tttcctaatc tgtgtgtgcc ctgtaacctg       5340
actggttaac agcagtcctt tgtaaacagt gtttttaaact ctcctagtca atatccaccc     5400
catccaattt atcaaggaag aaatggttca gaaatatttt tcagcctaca gttatgttca     5460
gtcacacaca catacaaaat gttccttttg cttttaaagt aatttttgac tcccagatca     5520
gtcagagccc ctacagcatt gttaagaaag tatttgattt ttgtctcaat gaaaataaaa     5580
ctatattcat ttccactcta aaaaaaaaa aaaaaa                                5616
```

<210> SEQ ID NO 10
<211> LENGTH: 4816
<212> TYPE: DNA
<213> ORGANISM: Homo sapiens

<400> SEQUENCE: 10

```
gttcccggat ttttgtgggc gcctgccccg cccctcgtcc ccctgctgtg tccatatatc      60
gaggcgatag ggttaaggga aggcggacgc ctgatgggtt aatgagcaaa ctgaagtgtt     120
ttccatgatc ttttttgagt cgcaattgaa gtaccacctc ccgagggtga ttgcttcccc     180
atgcggggta gaacctttgc tgtcctgttc accactctac ctccagcaca gaatttggct     240
tatgcctact caatgtgaag atgatgagga tgaaaacctt tgtgatgatc cacttccact     300
taatgaatgg tggcaaagca aagctatatt caagaccaca tgcaaagcta ctccctgagc     360
aaagagtcac agataaaacg ggggcaccag tagaatggcc aggacaaacg cagtgcagca     420
cagagactca gaccctggca gccatgcctg cgcaggcagt gatgagagtg acatgtactg     480
ttgtggacat gcacaaaagt gagtgtgcac cggcacagac atgaagctgc ggctccctgc     540
cagtcccgag acccacctgg acatgctccg ccacctctac cagggctgcc aggtggtgca     600
gggaaacctg gaactcacct acctgcccac caatgccagc ctgtccttcc tgcaggatat     660
ccaggaggtg cagggctacg tgctcatcgc tcacaaccaa gtgaggcagg tcccactgca     720
gaggctgcgg attgtgcgag gcacccagct cttttgaggac aactatgccc tggccgtgct     780
agacaatgga gacccgctga caataccac ccctgtcaca ggggcctccc caggaggcct     840
gcgggagctg cagcttcgaa gcctcacaga gatcttgaaa ggaggggtct tgatccagcg     900
gaaccccag ctctgctacc aggacacgat tttgtggaag acatcttcc acaagaacaa     960
ccagctggct ctcacactga tagacaccaa ccgctctcgg gcctgccacc cctgttctcc    1020
gatgtgtaag ggctcccgct gctggggaga gagttctgag gattgtcaga gcctgacgcg    1080
cactgtctgt gccggtggct gtgcccgctg caaggggcca ctgcccactg actgctgcca    1140
tgagcagtgt gctgccggct gcacgggccc caagcactct gactgcctgg cctgcctcca    1200
cttcaaccac agtggcatct gtgagctgca ctgcccagcc ctggtcacct acaacacaga    1260
cacgtttgag tccatgccca tccccgaggg ccggtataca ttcggcgcca gctgtgtgac    1320
tgcctgtccc tacaactacc tttctacgga cgtgggatcc tgcaccctcg tctgccccct    1380
gcacaaccaa gaggtgacag cagaggatgg aacacagcgg tgtgagaagt gcagcaagcc    1440
ctgtgcccga gtgtgctatg gtctgggcat ggagcacttg cgagaggtga gggcagttac    1500
cagtgccaat atccaggagt tgctggctg caagaagatc tttgggagcc tggcatttct    1560
gccggagagc tttgatgggg acccagcctc caacactgcc ccgctccagc cagagcagct    1620
ccaagtgttt gagactctgg aagagatcac aggttaccta tacatctcag catggccgga    1680
cagcctgcct gacctcagcg tcttccagaa cctgcaagta atccggggac gaattctgca    1740
caatggcgcc tactcgctga cctgcaagg gctgggcatc agctggctgg gctgcgctc    1800
actgagggaa ctgggcagtg actggcccct catccaccat aacacccacc tctgcttcgt    1860
gcacacggtg ccctgggacc agctcttcg gaacccgcac aagctctgc tccacactgc    1920
caaccggcca gaggacgagt gtgtgggcga gggcctggcc tgccaccagc tgtgcgcccg    1980
agggcactgc tgggtccag ggcccaccca gtgtgtcaac tgcagccagt ccttcgggg    2040
ccaggagtgc gtggaggaat gccgagtact gcaggggctc cccagggagt atgtgaatgc    2100
```

```
caggcactgt tgccgtgcc ccctgagtg tcagcccag aatggctcag tgacctgttt      2160
tggaccggag gctgaccagt gtgtggcctg tgcccactat aaggaccctc ccttctgcgt      2220
ggcccgctgc cccagcggtg tgaaacctga cctctcctac atgcccatct ggaagtttcc      2280
agatgaggag ggcgcatgcc agccttgccc catcaactgc acccactcct gtgtggacct      2340
ggatgacaag ggctgccccg ccgagcagag agccagccct ctgacgtcca tcatctctgc      2400
ggtggttggc attctgctgg tcgtggtctt gggggtggtc tttggatcc tcatcaagcg      2460 acggcagcag aagatccgga gtacacgat gcggagactg ctgcaggaaa cggagctggt      2520
ggagccgctg acacctagcg gagcgatgcc caaccaggcg cagatgcgga tcctgaaaga      2580
gacggagctg aggaaggtga aggtgcttgg atctggcgct tttggcacag tctacaaggg      2640
catctggatc cctgatgggg agaatgtgaa aattccagtg gccatcaaag tgttgaggga      2700
aaacacatcc cccaaagcca caaagaaat cttagacgaa gcatacgtga tggctggtgt      2760
gggctcccca tatgtctccc gccttctggg catctgcctg acatccacgg tgcagctggt      2820
gacacagctt atgccctatg gctgcctctt agaccatgtc cggaaaaacc gcggacgcct      2880
gggctcccag gacctgctga actggtgtat gcagattgcc aagggggatga gctacctgga      2940 ggatgtgcgg ctcgtacaca gggacttggc cgctcggaac gtgctggtca agagtcccaa      3000
ccatgtcaaa attacagact tcgggctggc tcggctgctg gacattgacg agacagagta      3060
ccatgcagat gggggcaagg tgcccatcaa gtggatggcg ctggagtcca ttctccgccg      3120
gcggttcacc caccagagtg atgtgtggag ttatggtgtg actgtgtggg agctgatgac      3180 ttttgggcc aaaccttacg atgggatccc agcccgggag atccctgacc tgctggaaa      3240 gggggagcgg ctgccccagc cccccatctg caccattgat gtctacatga tcatggtcaa      3300
atgttggatg attgactctg aatgtcggcc aagattccgg gagttggtgt ctgaattctc      3360
ccgcatggcc agggacccccc agcgctttgt ggtcatccag aatgaggact gggcccagc      3420 cagtcccttg acagcacct tctaccgctc actgctggag gacgatgaca tggggggacct      3480 ggtggatgct gaggagtatc tggtaccca gcagggcttc ttctgtccag accctgcccc      3540
gggcgctggg gcatggtcc accacaggca ccgcagctca tctaccagga gtggcggtgg      3600
ggacctgaca ctagggctgg agccctctga agaggaggcc cccaggtctc cactggcacc      3660
ctccgaaggg gctggctccg atgtatttga tggtgacctg gaatggggg cagccaaggg      3720 gctgcaaagc ctccccacac atgaccccag ccctctacag cggtacagtg aggaccccac      3780
agtacccctg ccctctgaga ctgatggcta cgttgccccc ctgacctgca gcccccagcc      3840
tgaatatgtg aaccagccag atgttcggcc ccagccccct tcgccccgag agggccctct      3900
gcctgctgcc cgacctgctg gtgccactct ggaaaggccc aagactctct ccccagggaa      3960
gaatggggtc gtcaaagacg tttttgcctt tgggggtgcc gtggagaacc ccgagtactt      4020 gacacccccag ggaggagctg cccctcagcc ccacccctcct cctgccttca gcccagcctt      4080
cgacaacctc tattactggg accaggaccc accagagcgg ggggctccac ccagcacctt      4140
caaagggaca cctacggcag agaacccaga gtacctgggt ctggacgtgc agtgtgaac      4200 cagaaggcca agtccgcaga agccctgatg tgtcctcagg gagcagggaa ggcctgactt      4260
ctgctggcat caagaggtgg gagggccctc cgaccacttc caggggaacc tgccatgcca      4320
ggaacctgtc ctaaggaacc ttccttcctg cttgagttcc cagatggctg aaggggtcc      4380 agcctcgttg gaagaggaac agcactgggg agtctttgtg gattctgagg ccctgcccaa      4440
tgagactcta gggtccagtg gatgccacag cccagcttgg ccctttcctt ccagatcctg      4500
```

```
ggtactgaaa gccttaggga agctggcctg agaggggaag cggccctaag ggagtgtcta    4560
agaacaaaag cgacccattc agagactgtc cctgaaacct agtactgccc cccatgagga    4620
aggaacagca atggtgtcag tatccaggct ttgtacagag tgcttttctg tttagttttt    4680
actttttttg ttttgttttt ttaaagatga aataaagacc caggggggaga atgggtgttg    4740 tatggggagg caagtgtggg gggtccttct ccacacccac tttgtccatt tgcaaatata    4800
ttttggaaaa cagcta                                                   4816

<210> SEQ ID NO 11
<211> LENGTH: 6456
<212> TYPE: DNA
<213> ORGANISM: Homo sapiens

<400> SEQUENCE: 11
gagttgtgcc tggagtgatg tttaagccaa tgtcagggca aggcaacagt ccctggccgt      60
cctccagcac ctttgtaatg catatgagct cgggagacca gtacttaaag ttggaggccc     120
gggagcccag gagctggcgg agggcgttcg tcctgggact gcacttgctc ccgtcgggtc     180
gcccggcttc accggacccg caggctcccg ggcagggcc ggggccagag ctcgcgtgtc      240
ggcgggacat gcgctgcgtc gcctctaacc tcgggctgtg ctcttttttcc aggtggcccg    300 ccggtttctg agccttctgc cctgcgggga cacggtctgc accctgcccg cggccacgga    360
ccatgaccat gaccctccac accaaagcat ccgggatggc cctactgcat cagatccaag    420
ggaacgagct ggagccctg aaccgtccgc agctcaagat cccctggag cggcccctgg     480 gcgaggtgta cctggacagc agcaagcccg ccgtgtacaa ctaccccgag ggcgccgcct    540
acgagttcaa cgccgcggcc gccgccaacg cgcaggtcta cggtcagacc ggcctcccct    600
acggcccccg gtctgaggct gcggcgttcg gctccaacgg cctgggggt tccccccac      660 tcaacagcgt gtctccgagc ccgctgatgc tactgcaccc gccgccgcag ctgtcgcctt    720
tcctgcagcc ccacggccag caggtgccct actacctgga gaacgagccc agcggctaca    780
cggtgcgcga ggccggcccg ccggcattct acaggccaaa ttcagataat cgacgccagg    840
gtggcagaga aagattggcc agtaccaatg acaagggaag tatggctatg gaatctgcca    900
aggagactcg ctactgtgca gtgtgcaatg actatgcttc aggctaccat tatggagtct    960
ggtcctgtga gggctgcaag gccttcttca agagaagtat tcaaggacat aacgactata   1020
tgtgtccagc caccaaccag tgcaccattg ataaaaacag gaggaagagc tgccaggcct   1080
gccgactccg caaatgctac gaagtgggaa tgatgaaagg tggatacga aaagaccgaa    1140 gaggagggag aatgttgaaa cacaagcgcc agagagatga tggggagggc aggggtgaag   1200
tggggtctgc tggagacatg agagctgcca acctttggcc aagcccgctc atgatcaaac   1260
gctctaagaa gaacagcctg gccttgtccc tgacggccga ccagatggtc agtgccttgt   1320
tggatgctga gccccccata ctctattccg agtatgatcc taccagaccc ttcagtgaag   1380
cttcgatgat gggcttactg accaacctgg cagacaggga gctggttcac atgatcaact   1440
gggcgaagag ggtgccaggc tttgtggatt tgaccctcca tgatcaggtc caccttctag   1500
aatgtgcctg gctagagatc ctgatgattg gtctcgtctg gcgctccatg gagcacccag   1560
ggaagctact gtttgctcct aacttgctct tggacaggaa ccagggaaaa tgtgtagagg   1620
gcatggtgga gatcttcgac atgctgctgg ctacatcatc tcggttccgc atgatgaatc   1680
tgcagggaga ggagtttgtg tgcctcaaat ctattatttt gcttaattct ggagtgtaca   1740
```

```
catttctgtc cagcaccctg aagtctctgg aagagaagga ccatatccac cgagtcctgg    1800
acaagatcac agacactttg atccacctga tggccaaggc aggcctgacc ctgcagcagc    1860
agcaccagcg gctggcccag ctcctcctca tcctctccca catcaggcac atgagtaaca    1920
aaggcatgga gcatctgtac agcatgaagt gcaagaacgt ggtgcccctc tatgacctgc    1980
tgctggagat gctggacgcc caccgcctac atgcgcccac tagccgtgga ggggcatccg    2040
tggaggagac ggaccaaagc cacttggcca ctgcgggctc tacttcatcg cattccttgc    2100
aaaagtatta catcacgggg gaggcagagg gttttccctgc cacggtctga gagctccctg    2160
gctcccacac ggttcagata atccctgctg cattttaccc tcatcatgca ccactttagc    2220
caaattctgt ctcctgcata cactccggca tgcatccaac accaatggct ttctagatga    2280
gtggccattc atttgcttgc tcagttctta gtggcacatc ttctgtcttc tgttgggaac    2340
agccaaaggg attccaaggc taaatctttg taacagctct ctttcccct tgctatgtta    2400 ctaagcgtga ggattcccgt agctcttcac agctgaactc agtctatggg ttggggctca    2460
gataactctg tgcatttaag ctacttgtag agacccaggc ctggagagta gacattttgc    2520
ctctgataag cactttttaa atggctctaa gaataagcca cagcaaagaa tttaaagtgg    2580
ctcctttaat tggtgacttg gagaaagcta ggtcaagggt ttattatagc accctcttgt    2640
attcctatgg caatgcatcc ttttatgaaa gtggtacacc ttaaagcttt tatatgactg    2700
tagcagagta tctggtgatt gtcaattcat tccccctata ggaatacaag gggcacacag    2760
ggaaggcaga tcccctagtt ggcaagacta ttttaacttg atacactgca gattcagatg    2820
tgctgaaagc tctgcctctg gctttccggt catgggttcc agttaattca tgcctcccat    2880
ggacctatgg agagcagcaa gttgatctta gttaagtctc cctatatgag ggataagttc    2940 ctgattttg ttttatttt tgtgttacaa agaaagccc tccctccctg aacttgcagt    3000
aaggtcagct tcaggacctg ttccagtggg cactgtactt ggatcttccc ggcgtgtgtg    3060
tgccttacac aggggtgaac tgttcactgt ggtgatgcat gatgaggta aatggtagtt    3120 gaaaggagca ggggccctgg tgttgcattt agccctgggg catggagctg aacagtactt    3180
gtgcaggatt gttgtggcta ctagagaaca agagggaaag tagggcagaa actggataca    3240
gttctgaggc acagccagac ttgctcaggg tggccctgcc acaggctgca gctacctagg    3300
aacattcctt gcagacccg cattgccctt tgggggtgcc ctgggatccc tggggtagtc    3360
cagctcttct tcatttccca gcgtggccct ggttggaaga agcagctgtc acagctgctg    3420
tagacagctg tgttcctaca attggcccag caccctgggg cacggagaa gggtggggac    3480 cgttgctgtc actactcagg ctgactgggg cctggtcaga ttacgtatgc ccttggtggt    3540
ttagagataa tccaaaatca gggtttggtt tggggaagaa aatcctcccc cttcctcccc    3600
cgccccgttc cctaccgcct ccactcctgc cagctcattt ccttcaattt cctttgaacc    3660
tataggctaa aaaagaaagg ctcattccag ccacagggca gccttccctg ggcctttgct    3720
tctctagcac aattatgggt tacttccttt ttcttaacaa aaaagaatgt ttgatttcct    3780
ctgggtgacc ttattgtctg taattgaaac cctattgaga ggtgatgtct gtgttagcca    3840
atgacccagg tgagctgctc gggcttctct tggtatgtct tgtttggaaa agtgatttc    3900 attcatttct gattgtccag ttaagtgatc accaaaggac tgagaatctg ggagggcaaa    3960
aaaaaaaaaa aagtttttat gtgcacttaa attttgggac aattttatgt atctgtgtta    4020
aggatatgtt taagaacata attctttgt tgctgtttgt ttaagaagca ccttagtttg    4080
tttaagaagc accttatata gtataatata tattttttg aaattacatt gcttgtttat    4140
```

```
cagacaattg aatgtagtaa ttctgttctg gatttaattt gactgggtta acatgcaaaa    4200
accaaggaaa aatatttagt ttttttttt tttttgtat actttcaag ctaccttgtc       4260
atgtatacag tcatttatgc ctaaagcctg gtgattattc atttaaatga agatcacatt    4320
tcatatcaac ttttgtatcc acagtagaca aaatagcact aatccagatg cctattgttg    4380
gatattgaat gacagacaat cttatgtagc aaagattatg cctgaaaagg aaaattattc    4440
agggcagcta attttgcttt taccaaaata tcagtagtaa tattttggaa cagtagctaa    4500
tgggtcagtg ggttcttttt aatgtttata cttagatttt cttttaaaaa aattaaaata    4560
aaacaaaaaa aaatttctag gactagacga tgtaatacca gctaaagcca aacaattata    4620
cagtggaagg ttttacatta ttcatccaat gtgtttctat tcatgttaag atactactac    4680
atttgaagtg gcagagaac atcagatgat tgaaatgttc gcccagggt ctccagcaac      4740
tttggaaatc tctttgtatt tttacttgaa gtgccactaa tggacagcag atattttctg    4800
gctgatgttg gtattgggtg taggaacatg atttaaaaaa aaactcttgc ctctgctttc    4860
ccccactctg aggcaagtta aaatgtaaaa gatgtgattt atctgggggg ctcaggtatg    4920
gtggggaagt ggattcagga atctggggaa tggcaaatat attaagaaga gtattgaaag    4980
tatttggagg aaaatggtta attctgggtg tgcaccaggg ttcagtagag tccacttctg    5040
ccctggagac cacaaatcaa ctagctccat ttacagccat ttctaaaatg gcagcttcag    5100
ttctagagaa gaaagaacaa catcagcagt aaagtccatg gaatagctag tggtctgtgt    5160
ttcttttcgc cattgcctag cttgccgtaa tgattctata atgccatcat gcagcaatta    5220
tgagaggcta ggtcatccaa agagaagacc ctatcaatgt aggttgcaaa atctaaccc     5280
taaggaagtg cagtctttga tttgatttcc ctagtaacct tgcagatatg tttaaccaag    5340
ccatagccca tgccttttga gggctgaaca aataagggac ttactgataa tttacttttg    5400
atcacattaa ggtgttctca ccttgaaatc ttatacactg aaatggccat tgatttaggc    5460
cactggctta gagtactcct tcccctgcat gacactgatt acaaatactt tcctattcat    5520
actttccaat tatgagatgg actgtgggta ctgggagtga tcactaacac catagtaatg    5580
tctaatattc acaggcagat ctgcttgggg aagctagtta tgtgaaaggc aaatagagtc    5640
atacagtagc tcaaaaggca accataattc tctttggtgc aggtcttggg agcgtgatct    5700
agattacact gcaccattcc caagttaatc ccctgaaaac ttactctcaa ctggagcaaa    5760
tgaactttgg tcccaaatat ccatcttttc agtagcgtta attatgctct gtttccaact    5820
gcatttcctt tccaattgaa ttaaagtgtg gcctcgtttt tagtcattta aaattgtttt    5880
ctaagtaatt gctgcctcta ttatggcact tcaattttgc actgtctttt gagattcaag    5940
aaaaatttct attctttttt ttgcatccaa ttgtgcctga acttttaaaa tatgtaaatg    6000
ctgccatgtt ccaaacccat cgtcagtgtg tgtgtttaga gctgtgcacc ctagaaacaa    6060
catattgtcc catgagcagg tgcctgagac acagaccct ttgcattcac agagaggtca    6120
ttggttatag agacttgaat taataagtga cattatgcca gtttctgttc tctcacaggt    6180
gataaacaat gctttttgtg cactacatac tcttcagtgt agagctcttg ttttatggga    6240
aaaggctcaa atgccaaatt gtgtttgatg gattaatatg cccttttgcc gatgcatact    6300
attactgatg tgactcggtt ttgtcgcagc tttgctttgt ttaatgaaac acacttgtaa    6360
acctcttttg cactttgaaa aagaatccag cgggatgctc gagcacctgt aaacaatttt    6420
ctcaacctat ttgatgttca aataaagaat taaact                              6456
```

<210> SEQ ID NO 12
<211> LENGTH: 4314
<212> TYPE: DNA
<213> ORGANISM: Homo sapiens

<400> SEQUENCE: 12

| | | | | | |
|---|---|---|---|---|---|
| cgagatcccg | gggagccagc | ttgctgggag | agcgggacgg | tccggagcaa | gcccagaggc | 60 |
| agaggaggcg | acagagggaa | aaagggccga | gctagccgct | ccagtgctgt | acaggagccg | 120 |
| aagggacgca | ccacgccagc | cccagcccgg | ctccagcgac | agccaacgcc | tcttgcagcg | 180 |
| cggcggcttc | gaagccgccg | cccggagctg | ccctttcctc | ttcggtgaag | ttttaaaag | 240 |
| ctgctaaaga | ctcggaggaa | gcaaggaaag | tgcctggtag | gactgacggc | tgcctttgtc | 300 |
| ctcctcctct | ccaccccgcc | tcccccacc | ctgccttccc | ccctccccc | gtcttctctc | 360 |
| ccgcagctgc | ctcagtcggc | tactctcagc | caacccccct | caccacccctt | ctccccaccc | 420 |
| gcccccccgc | cccgtcggc | ccagcgctgc | cagcccgagt | ttgcagagag | gtaactccct | 480 |
| ttggctgcga | gcgggcgagc | tagctgcaca | ttgcaaagaa | ggctcttagg | agccaggcga | 540 |
| ctggggagcg | gcttcagcac | tgcagccacg | acccgcctgg | ttaggctgca | cgcggagaga | 600 |
| accctctgtt | ttccccccact | ctctctccac | ctcctcctgc | cttccccacc | ccgagtgcgg | 660 |
| agccagagat | caaagatga | aaaggcagtc | aggtcttcag | tagccaaaaa | acaaaacaaa | 720 |
| caaaacaaa | aaagccgaaa | taaagaaaa | agataataac | tcagttctta | tttgcaccta | 780 |
| cttcagtgga | cactgaattt | ggaaggtgga | ggattttgtt | ttttctttt | aagatctggg | 840 |
| catcttttga | atctaccctt | caagtattaa | gagacagact | gtgagcctag | cagggcagat | 900 |
| cttgtccacc | gtgtgtcttc | ttctgcacga | gactttgagg | ctgtcagagc | gcttttgcg | 960 |
| tggttgctcc | cgcaagtttc | cttctctgga | gcttcccgca | ggtgggcagc | tagctgcagc | 1020 |
| gactaccgca | tcatcacagc | ctgttgaact | cttctgagca | agagaagggg | aggcggggta | 1080 |
| agggaagtag | gtggaagatt | cagccaagct | caaggatgga | agtgcagtta | gggctgggaa | 1140 |
| gggtctaccc | tcggccgccg | tccaagacct | accgaggagc | tttccagaat | ctgttccaga | 1200 |
| gcgtgcgcga | agtgatccag | aacccgggcc | ccaggcaccc | agaggccgcg | agcgcagcac | 1260 |
| ctcccggcgc | cagtttgctg | ctgctgcagc | agcagcagca | gcagcagcag | cagcagcagc | 1320 |
| agcagcagca | gcagcagcag | cagcagcagc | agcaagagac | tagccccagg | cagcagcagc | 1380 |
| agcagcaggg | tgaggatggt | tctccccaag | cccatcgtag | aggccccaca | ggctacctgg | 1440 |
| tcctggatga | ggaacagcaa | ccttcacagc | cgcagtcggc | cctggagtgc | accccgaga | 1500 |
| gaggttgcgt | cccagagcct | ggagccgccg | tggccgccag | caaggggctg | ccgcagcagc | 1560 |
| tgccagcacc | tccggacgag | gatgactcag | ctgccccatc | cacgttgtcc | ctgctgggcc | 1620 |
| ccactttccc | cggcttaagc | agctgctccg | ctgaccttaa | agacatcctg | agcgaggcca | 1680 |
| gcaccatgca | actccttcag | caacagcagc | aggaagcagt | atccgaaggc | agcagcagcg | 1740 |
| ggagagcgag | ggaggcctcg | ggggctccca | cttcctccaa | ggacaattac | ttaggggca | 1800 |
| cttcgaccat | ttctgacaac | gccaaggagt | tgtgtaaggc | agtgtcggtg | tccatgggcc | 1860 |
| tgggtgtgga | ggcgttggag | catctgagtc | caggggaaca | gcttcggggg | gattgcatgt | 1920 |
| acgccccact | tttgggagtt | ccacccgctg | tgcgtccac | tccttgtgcc | ccattggccg | 1980 |
| aatgcaaagg | ttctctgcta | gacgacagcg | caggcaagag | cactgaagat | actgctgagt | 2040 |
| attcccctt | caagggaggt | tacaccaaag | gctagaagg | cgagagccta | ggctgctctg | 2100 |
| gcagcgctgc | agcagggagc | tccgggacac | ttgaactgcc | gtctaccctg | tctctctaca | 2160 |

```
agtccggagc actggacgag gcagctgcgt accagagtcg cgactactac aactttccac    2220
tggctctggc cggaccgccg ccccctccgc cgcctcccca tccccacgct cgcatcaagc    2280
tggagaaccc gctggactac ggcagcgcct gggcggctgc ggcggcgcag tgccgctatg    2340
gggacctggc gagcctgcat ggcgcgggtg cagcgggacc cggttctggg tcaccctcag    2400
ccgccgcttc ctcatcctgg cacactctct tcacagccga agaaggccag ttgtatggac    2460
cgtgtggtgg tggtggggt ggtggcggcg gcggcggcgg cggcggcggc ggcggcggcg    2520
gcggcggcgg cggcgaggcg ggagctgtag cccctacgg ctacactcgg ccccctcagg    2580
ggctggcggg ccaggaaagc gacttcaccg cacctgatgt gtggtaccct gcggcatgg    2640 tgagcagagt gccctatccc agtcccactt gtgtcaaaag cgaaatgggc cctggatgg    2700 atagctactc cggaccttac ggggacatgc gtttggagac tgccagggac catgttttgc    2760
ccattgacta ttactttcca ccccagaaga cctgcctgat ctgtggagat gaagcttctg    2820
ggtgtcacta tggagctctc acatgtggaa gctgcaaggt cttcttcaaa agagccgctg    2880
aagggaaaca gaagtacctg tgcgccagca gaaatgattg cactattgat aaattccgaa    2940
ggaaaaattg tccatcttgt cgtcttcgga atgttatga agcagggatg actctgggag    3000
cccggaagct gaagaaactt ggtaatctga actacaggtc ggaaggagag cttccagca    3060 ccaccagccc cactgaggag acaacccaga agctgacagt gtcacacatt gaaggctatg    3120
aatgtcagcc catctttctg aatgtcctgg aagccattga gccaggtgta gtgtgtgctg    3180
gacacgacaa caaccagccc gactcctttg cagccttgct ctctagcctc aatgaactgg    3240
gagagagaca gcttgtacac gtggtcaagt gggccaaggc cttgcctggc ttccgcaact    3300
tacacgtgga cgaccagatg gctgtcattc agtactcctg gatggggctc atggtgtttg    3360
ccatgggctg gcgatccttc accaatgtca actccaggat gctctacttc gcccctgatc    3420
tggttttcaa tgagtaccgc atgcacaagt cccggatgta cagccagtgt gtccgaatga    3480
ggcacctctc tcaagagttt ggatggctcc aaatcacccc ccaggaattc ctgtgcatga    3540
aagcactgct actcttcagc attattccag tggatgggct gaaaaatcaa aaattctttg    3600
atgaacttcg aatgaactac atcaaggaac tcgatcgtat cattgcatgc aaaagaaaaa    3660
atcccacatc ctgctcaaga cgcttctacc agctcaccaa gctcctggac tccgtgcagc    3720
ctattgcgag agagctgcat cagttcactt ttgacctgct aatcaagtca cacatggtga    3780
gcgtggactt tccggaaatg atggcagaga tcatctctgt gcaagtgccc aagatccttt    3840
ctgggaaagt caagcccatc tatttccaca cccagtgaag cattggaaac cctatttccc    3900 cacccccagct catgccccct ttcagatgtc ttctgcctgt ataactctg cactactcct    3960 ctgcagtgcc ttggggaatt tcctctattg atgtacagtc tgtcatgaac atgttcctga    4020
attctatttg ctgggctttt tttttctctt tctctccttt cttttctctc ttccctccct    4080
atctaaccct cccatggcac cttcagactt tgcttcccat tgtggctcct atctgtgttt    4140
tgaatggtgt tgtatgcctt taaatctgtg atgatcctca tatggcccag tgtcaagttg    4200
tgcttgttta cagcactact ctgtgccagc cacacaaacg tttacttatc ttatgccacg    4260
ggaagtttag agagctaaga ttatctgggg aaatcaaaac aaaaacaagc aaac        4314
```

<210> SEQ ID NO 13
<211> LENGTH: 2554
<212> TYPE: DNA
<213> ORGANISM: Homo sapiens

```
<400> SEQUENCE: 13
acaaggcagc ctcgctcgag cgcaggccaa tcggctttct agctagaggg tttaactcct      60
atttaaaaag aagaacctttt gaattctaac ggctgagctc ttggaagact tgggtccttg    120
ggtcgcaggt gggagccgac gggtgggtag accgtggggg atatctcagt ggcggacgag    180
gacggcgggg acaaggggcg gctggtcgga gtggcggagc gtcaagtccc ctgtcggttc    240
ctccgtccct gagtgtcctt ggcgctgcct tgtgcccgcc cagcgccttt gcatccgctc    300
ctgggcaccg aggcgccctg taggatactg cttgttactt attacagcta gagggtctca    360
ctccattgcc caggccagag tgcgggata tttgataaga aacttcagtg aaggccgggc      420
gcggtggctc atgcccgtaa tcccagcatt ttcggaggcc gaggctggag tgcaatggtg    480
tgatctcagc tcactgcaac ctctgcttcc tgggtttaag tgattctcct gcctcagcct    540
cccgagtagc tgggattaca ggcatcatgg accgatctaa agaaaactgc atttcaggac    600
ctgttaaggc tacagctcca gttggaggtc caaaacgtgt tctcgtgact cagcaatttc    660
cttgtcagaa tccattacct gtaaatagtg gccaggctca gcgggtcttg tgtccttcaa    720
attcttccca gcgcattcct ttgcaagcac aaaagcttgt ctccagtcac aagccggttc    780
agaatcagaa gcagaagcaa ttgcaggcaa ccagtgtacc tcatcctgtc tccaggccac    840
tgaataacac ccaaaagagc aagcagcccc tgccatcggc acctgaaaat aatcctgagg    900
aggaactggc atcaaaacag aaaaatgaag aatcaaaaaa gaggcagtgg gctttgaagg    960
actttgaaat tggtcgccct ctgggtaaag gaaagtttgg taatgtttat ttggcaagag   1020
aaaagcaaag caagtttatt ctggctctta agtgttatt taaagctcag ctggagaaag    1080
ccggagtgga gcatcagctc agaagagaag tagaaataca gtcccaccttt cggcatccta   1140 atattcttag actgtatggt tatttccatg atgctaccag agtctaccta attctggaat   1200
atgcaccact tggaacagtt tatagagaac ttcagaaact ttcaaagttt gatgagcaga    1260
gaactgctac ttatataaca gaattggcaa atgccctgtc ttactgtcat cgaagagag    1320 ttattcatag agacattaag ccagagaact tacttcttgg atcagctgga gagcttaaaa    1380
ttgcagattt tgggtggtca gtacatgctc catcttccag gaggaccact ctctgtggca    1440
ccctggacta cctgcccct gaaatgattg aaggtcggat gcatgatgag aaggtggatc    1500
tctggagcct tggagttctt tgctatgaat ttttagttgg gaagcctcct tttgaggcaa    1560
acacatacca agagacctac aaaagaatat cacgggttga attcacattc cctgactttg   1620
taacagaggg agccagggac ctcatttcaa gactgttgaa gcataatccc agccagaggc    1680
caatgctcag agaagtactt gaacaccct ggatcacagc aaattcatca aaaccatcaa      1740
attgccaaaa caagaatca gctagcaaac agtcttagga atcgtgcagg gggagaaatc      1800
cttgagccag ggctgccata taacctgaca ggaacatgct actgaagttt attttaccat    1860
tgactgctgc cctcaatcta gaacgctaca caagaaatat ttgttttact cagcaggtgt    1920
gccttaacct cccctattcag aaagctccac atcaataaac atgacactct gaagtgaaag    1980
tagccacgag aattgtgcta cttatactgg ttcataatct ggaggcaagg ttcgactgca    2040
gccgccccgt cagcctgtgc taggcatggt gtcttcacag gaggcaaatc cagagcctgg   2100
ctgtggggaa agtgaccact ctgccctgac cccgatcagt taaggagctg tgcaataacc    2160
ttcctagtac ctgagtgagt gtgtaactta ttgggttggc gaagcctggt aaagctgttg    2220
gaatgagtat gtgattcttt ttaagtatga aaataaagat atatgtacag acttgtatt    2280 tttctctggt ggcattcctt taggaatgct gtgtgtctgt ccggcacccc ggtaggcctg    2340
```

```
attgggtttc tagtcctcct taaccactta tctcccatat gagagtgtga aaaataggaa    2400
cacgtgctct acctccattt agggatttgc ttgggataca gaagaggcca tgtgtctcag    2460
agctgttaag ggcttatttt tttaaaacat tggagtcata gcatgtgtgt aaactttaaa    2520
tatgcaaata aataagtatc tatgtctaaa aaaa                                2554

<210> SEQ ID NO 14
<211> LENGTH: 1616
<212> TYPE: DNA
<213> ORGANISM: Homo sapiens

<400> SEQUENCE: 14
ctccctgtgt tggtggagga tgtctgcagc agcatttaaa ttctgggagg gcttggttgt      60
cagcagcagc aggaggaggc agagcacagc atcgtcggga ccagactcgt ctcaggccag     120
ttgcagcctt ctcagccaaa cgccgaccaa ggaaaactca ctaccatgag aattgcagtg     180
atttgctttt gcctcctagg catcacctgt gccataccag ttaaacaggc tgattctgga     240
agttctgagg aaaagcagct ttacaacaaa tacccagatg ctgtggccac atggctaaac     300
cctgacccat ctcagaagca gaatctccta gccccacaga cccttccaag taagtccaac     360
gaaagccatg accacatgga tgatatggat gatgaagatg atgatgacca tgtggacagc     420
caggactcca ttgactcgaa cgactctgat gatgtagatg acactgatga ttctcaccag     480
tctgatgagt ctcaccattc tgatgaatct gatgaactgg tcactgattt tcccacggac     540
ctgccagcaa ccgaagtttt cactccagtt gtccccacag tagacacata tgatggccga     600
ggtgatagtg tggtttatgg actgaggtca aaatctaaga gtttcgcag acctgacatc     660 cagtaccctg atgctacaga cgaggacatc acctcacaca tggaaagcga ggagttgaat     720
ggtgcataca aggccatccc cgttgcccag gacctgaacg cgccttctga ttgggacagc     780
cgtgggaagg acagttatga aacgagtcag ctggatgacc agagtgctga aacccacagc     840
cacaagcagt ccagattata taagcggaaa gccaatgatg agagcaatga gcattccgat     900
gtgattgata gtcaggaact ttccaaagtc agccgtgaat tccacagcca tgaatttcac     960
agccatgaag atatgctggt tgtagacccc aaaagtaagg aagaagataa acacctgaaa    1020
tttcgtattt ctcatgaatt agatagtgca tcttctgagg tcaattaaaa ggagaaaaaa    1080
tacaatttct cactttgcat ttagtcaaaa gaaaaaatgc tttatagcaa aatgaaagag    1140
aacatgaaat gcttctttct cagtttattg gttgaatgtg tatctatttg agtctggaaa    1200
taactaatgt gtttgataat tagtttagtt tgtggcttca tggaaactcc ctgtaaacta    1260
aaagcttcag ggttatgtct atgttcattc tatagaagaa atgcaaacta tcactgtatt    1320
ttaatatttg ttattctctc atgaatagaa atttatgtag aagcaaacaa aatactttta    1380
cccacttaaa aagagaatat aacattttat gtcactataa tcttttgttt tttaagttag    1440
tgtatatttt gttgtgatta tcttttgtg gtgtgaataa atcttttatc ttgaatgtaa    1500
taagaatttg gtggtgtcaa ttgcttattt gttttcccac ggttgtccag caattaataa    1560
aacataacct tttttactgc ctaaaaaaaa aaaaaaaaa aaaaaaaaaa aaaaaa          1616

<210> SEQ ID NO 15
<211> LENGTH: 2276
<212> TYPE: DNA
<213> ORGANISM: Homo sapiens

<400> SEQUENCE: 15
```

| | |
|---|---:|
| aagcccagca gccccggggc ggatggctcc ggccgcctgg ctccgcagcg cggccgcgcg | 60 |
| cgccctcctg cccccgatgc tgctgctgct gctccagccg ccgccgctgc tggcccgggc | 120 |
| tctgccgccg gacgcccacc acctccatgc cgagaggagg gggccacagc cctggcatgc | 180 |
| agccctgccc agtagcccgg cacctgcccc tgccacgcag gaagcccccc ggcctgccag | 240 |
| cagcctcagg cctccccgct gtggcgtgcc cgacccatct gatgggctga gtgcccgcaa | 300 |
| ccgacagaag aggttcgtgc tttctggcgg gcgctgggag aagacggacc tcacctacag | 360 |
| gatccttcgg ttcccatggc agttggtgca ggagcaggtg cggcagacga tggcagaggc | 420 |
| cctaaaggta tggagcgatg tgacgccact cacctttact gaggtgcacg agggccgtgc | 480 |
| tgacatcatg atcgacttcg ccaggtactg catggggac gacctgccgt ttgatgggcc | 540 |
| tgggggcatc ctgcccatg ccttcttccc caagactcac cgagaagggg atgtccactt | 600 |
| cgactatgat gagacctgga ctatcgggga tgaccagggc acagacctgc tgcaggtggc | 660 |
| agcccatgaa tttggccacg tgctggggct gcagcacaca acagcagcca aggccctgat | 720 |
| gtccgccttc tacacctttc gctacccact gagtctcagc ccagatgact gcaggggcgt | 780 |
| tcaacaccta tatggccagc cctggcccac tgtcacctcc aggaccccag ccctgggccc | 840 |
| ccaggctggg atagacacca atgagattgc accgctggag ccagacgccc cgccagatgc | 900 |
| ctgtgaggcc tcctttgacg cggtctccac catccgaggc gagctctttt tcttcaaagc | 960 |
| gggctttgtg tggcgcctcc gtggggggcca gctgcagccc ggctacccag cattggcctc | 1020 |
| tcgccactgg caggggactgc ccagccctgt ggacgctgcc ttcgaggatg cccagggcca | 1080 |
| catttggttc ttccaaggtg ctcagtactg ggtgtacgac ggtgaaaagc cagtcctggg | 1140 |
| ccccgcaccc ctcaccgagc tgggcctggt gaggttcccg gtccatgctg ccttggtctg | 1200 |
| gggtcccgag aagaacaaga tctacttctt ccgaggcagg gactactggc gtttccaccc | 1260 |
| cagcacccgg cgtgtagaca gtcccgtgcc ccgcagggcc actgactgga gagggtgcc | 1320 |
| ctctgagatc gacgctgcct tccaggatgc tgatggctat gcctacttcc tgcgcggccg | 1380 |
| cctctactgg aagtttgacc ctgtgaaggt gaaggctctg gaaggcttcc cccgtctcgt | 1440 |
| gggtcctgac ttctttggct gtgccagcc tgccaacact ttcctctgac catggcttgg | 1500 |
| atgccctcag gggtgctgac ccctgccagg ccacgaatat caggctagag acccatggcc | 1560 |
| atctttgtgg ctgtgggcac caggcatggg actgagccca tgtctcctca ggggatgggg | 1620 |
| gtggggtaca accaccatga caactgccgg gagggccacg caggtcgtgg tcacctgcca | 1680 |
| gcgactgtct cagactgggc agggaggctt tggcatgact taagaggaag ggcagtcttg | 1740 |
| ggcccgctat gcaggtcctg gcaaacctgg ctgccctgtc tccatccctg tccctcaggg | 1800 |
| tagcaccatg gcaggactgg gggaactgga gtgtccttgc tgtatccctg ttgtgaggtt | 1860 |
| ccttccaggg gctggcactg aagcaagggt gctggggccc catggccttc agccctggct | 1920 |
| gagcaactgg gctgtagggc agggccactt cctgaggtca ggtcttggta ggtgcctgca | 1980 |
| tctgtctgcc ttctggctga caatcctgga aatctgttct ccagaatcca ggccaaaaag | 2040 |
| ttcacagtca aatggggagg ggtattcttc atgcaggaga ccccaggccc tggaggctgc | 2100 |
| aacatacctc aatcctgtcc caggccggat cctcctgaag cccttttcgc agcactgcta | 2160 |
| tcctccaaag ccattgtaaa tgtgtgtaca gtgtgtataa accttcttct tctttttttt | 2220 |
| tttttaaact gaggattgtc attaaacaca gttgttttct aaaaaaaaaa aaaaaa | 2276 |

```
<210> SEQ ID NO 16
<211> LENGTH: 3035
```

<212> TYPE: DNA
<213> ORGANISM: Homo sapiens

<400> SEQUENCE: 16

| | | | | | |
|---|---|---|---|---|---|
| agagccagag | caggatggag | aggagacgca | tcacctccgc | tgctcgccgc | tcctacgtct | 60 |
| cctcagggga | gatgatggtg | gggggcctgg | ctcctggccg | ccgtctgggt | cctggcaccc | 120 |
| gcctctccct | ggctcgaatg | cccctccac | tcccgacccg | ggtggatttc | tccctggctg | 180 |
| gggcactcaa | tgctggcttc | aaggagaccc | gggccagtga | gcgggcagag | atgatggagc | 240 |
| tcaatgaccg | ctttgccagc | tacatcgaga | aggttcgctt | cctggaacag | caaaacaagg | 300 |
| cgctggctgc | tgagctgaac | cagctgcggg | ccaaggagcc | caccaagctg | gcagacgtct | 360 |
| accaggctga | gctgcgagag | ctgcggctgc | ggctcgatca | actcaccgcc | aacagcgccc | 420 |
| ggctggaggt | tgagagggac | aatctggcac | aggacctggc | cactgtgagg | cagaagctcc | 480 |
| aggatgaaac | caacctgagg | ctggaagccg | agaacaacct | ggctgcctat | agacaggaag | 540 |
| cagatgaagc | caccctggcc | cgtctggatc | tggagaggaa | gattgagtcg | ctggaggagg | 600 |
| agatccggtt | cttgaggaag | atccacgagg | aggaggttcg | ggaactccag | gagcagctgg | 660 |
| cccgacagca | ggtccatgtg | gagcttacg | tggccaagcc | agacctcacc | gcagccctga | 720 |
| aagagatccg | cacgcagtat | gaggcaatgg | cgtccagcaa | catgcatgaa | gccgaagagt | 780 |
| ggtaccgctc | caagtttgca | gacctgacag | acgctgctgc | ccgcaacgcg | gagctgctcc | 840 |
| gccaggccaa | gcacgaagcc | aacgactacc | ggcgccagtt | gcagtccttg | acctgcgacc | 900 |
| tggagtctct | gcgcggcacg | aacgagtccc | tggagaggca | gatgcgcgag | caggaggagc | 960 |
| ggcacgtgcg | ggaggcggcc | agttatcagg | aggcgctggc | gcggctggag | aagaggggc | 1020 |
| agagcctcaa | ggacgagatg | gcccgccact | gcaggagta | ccaggacctg | ctcaatgtca | 1080 |
| agctggccct | ggacatcgag | atcgccacct | acaggaagct | gctagagggc | gaggagaacc | 1140 |
| ggatcaccat | tcccgtgcag | accttctcca | acctgcagat | tcgagaaacc | agcctggaca | 1200 |
| ccaagtctgt | gtcagaaggc | cacctcaaga | ggaacatcgt | ggtgaagacc | gtggagatgc | 1260 |
| gggatggaga | ggtcattaag | gagtccaagc | aggagcacaa | ggatgtgatg | tgaggcagga | 1320 |
| cccacctggt | ggcctctgcc | ccgtctcatg | aggggcccga | gcagaagcag | gatagttgct | 1380 |
| ccgcctctgc | tggcacattt | ccccagacct | gagctcccca | ccaccccagc | tgctcccctc | 1440 |
| cctcctctgt | ccctaggtca | gcttgctgcc | ctaggctccg | tcagtatcag | gcctgccaga | 1500 |
| cggcacccac | ccagcaccca | gcaactccaa | ctaacaagaa | actcaccccc | aaggggcagt | 1560 |
| ctggagggga | atggccagca | gcttgcgtta | gaatgaggag | gaaggagaga | aggggaggag | 1620 |
| ggcgggggc | acctactaca | tcgccctcca | catccctgat | tcctgttgtt | atggaaactg | 1680 |
| ttgccagaga | tggaggttct | ctcggagtat | ctggaactg | tgcctttgag | tttcctcagg | 1740 |
| ctgctggagg | aaaactgaga | ctcagacagg | aaagggaagg | ccccacagac | aaggtagccc | 1800 |
| tggccagagg | cttgttttgt | cttttggttt | ttatgaggtg | ggatatccct | atgctgccta | 1860 |
| ggctgacctt | gaactcctgg | gctcaagcag | tctacccacc | tcagcctcct | gtgtagctgg | 1920 |
| gattatagat | tggagccacc | atgcccagct | cagagggttg | ttctcctaga | ctgaccctga | 1980 |
| tcagtctaag | atgggtgggg | acgtcctgcc | acctgggca | gtcacctgcc | cagatcccag | 2040 |
| aaggacctcc | tgagcgatga | ctcaagtgtc | tcagtccacc | tgagctgcca | tccagggatg | 2100 |
| ccatctgtgg | gcacgctgtg | ggcaggtggg | agcttgattc | tcagcacttg | ggggatctgt | 2160 |
| tgtgtacgtg | gagagggatg | aggtgctggg | agggatagag | gggggctgcc | tggcccccag | 2220 |

-continued

```
ctgtgggtac agagaggtca agcccaggag gactgccccg tgcagactgg aggggacgct    2280
ggtagagatg gaggaggagg caattgggat ggcgctaggc atacaagtag gggttgtggg    2340
tgaccagttg cacttggcct ctggattgtg gaattaagg  aagtgactca tcctcttgaa    2400
gatgctgaaa caggagagaa aggggatgta tccatggggg cagggcatga ctttgtccca    2460
tttctaaagg cctcttcctt gctgtgtcat accaggccgc cccagcctct gagcccctgg    2520
gactgctgct tcttaacccc agtaagccac tgccacacgt ctgaccctct ccaccccata    2580
gtgaccggct gcttttccct aagccaaggg cctcttgcgg tcccttctta ctcacacaca    2640
aaatgtaccc agtattctag gtagtgccct attttacaat tgtaaaactg aggcacgagc    2700
aaagtgaaga cactggctca tattcctgca gcctggaggc cgggtgctca gggctgacac    2760
gtccacccca gtgcacccac tctgctttga ctgagcagac tggtgagcag actggtggga    2820
tctgtgccca gagatgggac tgggagggcc cacttcaggg ttctcctctc ccctctaagg    2880
ccgaagaagg gtccttccct ctccccaaga cttggtgtcc tttccctcca cttcctcctg    2940
ccacctgctg ctgctgctgc tgctaatctt cagggcactg ctgctgcctt tagtcgctga    3000
ggaaaaataa agacaaatgc tgcgcccttc cccag                              3035
```

<210> SEQ ID NO 17
<211> LENGTH: 525
<212> TYPE: PRT
<213> ORGANISM: Homo sapiens

<400> SEQUENCE: 17

```
Met Arg Arg Arg Arg Arg Asp Gly Phe Tyr Pro Ala Pro Asp Phe
1               5                   10                  15

Arg Asp Arg Glu Ala Glu Asp Met Ala Gly Val Phe Asp Ile Asp Leu
            20                  25                  30

Asp Gln Pro Glu Asp Ala Gly Ser Glu Asp Glu Leu Glu Glu Gly Gly
        35                  40                  45

Gln Leu Asn Glu Ser Met Asp His Gly Gly Val Gly Pro Tyr Glu Leu
    50                  55                  60

Gly Met Glu His Cys Glu Lys Phe Glu Ile Ser Glu Thr Ser Val Asn
65                  70                  75                  80

Arg Gly Pro Glu Lys Ile Arg Pro Glu Cys Phe Glu Leu Leu Arg Val
                85                  90                  95

Leu Gly Lys Gly Gly Tyr Gly Lys Val Phe Gln Val Arg Lys Val Thr
            100                 105                 110

Gly Ala Asn Thr Gly Lys Ile Phe Ala Met Lys Val Leu Lys Lys Ala
        115                 120                 125

Met Ile Val Arg Asn Ala Lys Asp Thr Ala His Thr Lys Ala Glu Arg
    130                 135                 140

Asn Ile Leu Glu Glu Val Lys His Pro Phe Ile Val Asp Leu Ile Tyr
145                 150                 155                 160

Ala Phe Gln Thr Gly Gly Lys Leu Tyr Leu Ile Leu Glu Tyr Leu Ser
                165                 170                 175

Gly Gly Glu Leu Phe Met Gln Leu Glu Arg Glu Gly Ile Phe Met Glu
            180                 185                 190

Asp Thr Ala Cys Phe Tyr Leu Ala Glu Ile Ser Met Ala Leu Gly His
        195                 200                 205

Leu His Gln Lys Gly Ile Ile Tyr Arg Asp Leu Lys Pro Glu Asn Ile
    210                 215                 220

Met Leu Asn His Gln Gly His Val Lys Leu Thr Asp Phe Gly Leu Cys
```

```
                225                 230                 235                 240
        Lys Glu Ser Ile His Asp Gly Thr Val Thr His Thr Phe Cys Gly Thr
                        245                 250                 255

Ile Glu Tyr Met Ala Pro Glu Ile Leu Met Arg Ser Gly His Asn Arg
                    260                 265                 270

Ala Val Asp Trp Trp Ser Leu Gly Ala Leu Met Tyr Asp Met Leu Thr
                    275                 280                 285

Gly Ala Pro Pro Phe Thr Gly Glu Asn Arg Lys Thr Ile Asp Lys
                290                 295                 300

Ile Leu Lys Cys Lys Leu Asn Leu Pro Pro Tyr Leu Thr Gln Glu Ala
        305                 310                 315                 320

Arg Asp Leu Leu Lys Leu Leu Lys Arg Asn Ala Ala Ser Arg Leu
                        325                 330                 335

Gly Ala Gly Pro Gly Asp Ala Gly Glu Val Gln Ala His Pro Phe Phe
                        340                 345                 350

Arg His Ile Asn Trp Glu Glu Leu Leu Ala Arg Lys Val Glu Pro Pro
                        355                 360                 365

Phe Lys Pro Leu Leu Gln Ser Glu Glu Asp Val Ser Gln Phe Asp Ser
                370                 375                 380

Lys Phe Thr Arg Gln Thr Pro Val Asp Ser Pro Asp Asp Ser Thr Leu
        385                 390                 395                 400

Ser Glu Ser Ala Asn Gln Val Phe Leu Gly Phe Thr Tyr Val Ala Pro
                        405                 410                 415

Ser Val Leu Glu Ser Val Lys Glu Lys Phe Ser Phe Glu Pro Lys Ile
                    420                 425                 430

Arg Ser Pro Arg Arg Phe Ile Gly Ser Pro Arg Thr Pro Val Ser Pro
                    435                 440                 445

Val Lys Phe Ser Pro Gly Asp Phe Trp Gly Arg Gly Ala Ser Ala Ser
                450                 455                 460

Thr Ala Asn Pro Gln Thr Pro Val Glu Tyr Pro Met Glu Thr Ser Gly
        465                 470                 475                 480

Ile Glu Gln Met Asp Val Thr Met Ser Gly Glu Ala Ser Ala Pro Leu
                        485                 490                 495

Pro Ile Arg Gln Pro Asn Ser Gly Pro Tyr Lys Lys Gln Ala Phe Pro
                    500                 505                 510

Met Ile Ser Lys Arg Pro Glu His Leu Arg Met Asn Leu
                    515                 520                 525

<210> SEQ ID NO 18
<211> LENGTH: 249
<212> TYPE: PRT
<213> ORGANISM: Homo sapiens

<400> SEQUENCE: 18

Met Lys Leu Asn Ile Ser Phe Pro Ala Thr Gly Cys Gln Lys Leu Ile
1               5                   10                  15

Glu Val Asp Asp Glu Arg Lys Leu Arg Thr Phe Tyr Glu Lys Arg Met
                20                  25                  30

Ala Thr Glu Val Ala Ala Asp Ala Leu Gly Glu Glu Trp Lys Gly Tyr
            35                  40                  45

Val Val Arg Ile Ser Gly Gly Asn Asp Lys Gln Gly Phe Pro Met Lys
        50                  55                  60

Gln Gly Val Leu Thr His Gly Arg Val Arg Leu Leu Leu Ser Lys Gly
65                  70                  75                  80
```

His Ser Cys Tyr Arg Pro Arg Arg Thr Gly Glu Arg Lys Arg Lys Ser
            85                  90                  95

Val Arg Gly Cys Ile Val Asp Ala Asn Leu Ser Val Leu Asn Leu Val
        100                 105                 110

Ile Val Lys Lys Gly Glu Lys Asp Ile Pro Gly Leu Thr Asp Thr Thr
        115                 120                 125

Val Pro Arg Arg Leu Gly Pro Lys Arg Ala Ser Arg Ile Arg Lys Leu
130                 135                 140

Phe Asn Leu Ser Lys Glu Asp Asp Val Arg Gln Tyr Val Val Arg Lys
145                 150                 155                 160

Pro Leu Asn Lys Glu Gly Lys Lys Pro Arg Thr Lys Ala Pro Lys Ile
                165                 170                 175

Gln Arg Leu Val Thr Pro Arg Val Leu Gln His Lys Arg Arg Arg Ile
            180                 185                 190

Ala Leu Lys Lys Gln Arg Thr Lys Lys Asn Lys Glu Glu Ala Ala Glu
        195                 200                 205

Tyr Ala Lys Leu Leu Ala Lys Arg Met Lys Glu Ala Lys Glu Lys Arg
    210                 215                 220

Gln Glu Gln Ile Ala Lys Arg Arg Arg Leu Ser Ser Leu Arg Ala Ser
225                 230                 235                 240

Thr Ser Lys Ser Glu Ser Ser Gln Lys
                245

<210> SEQ ID NO 19
<211> LENGTH: 480
<212> TYPE: PRT
<213> ORGANISM: Homo sapiens

<400> SEQUENCE: 19

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

```
Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
                260                 265                 270

Arg Asp Leu Lys Leu Glu Asn Leu Met Leu Asp Lys Asp Gly His Ile
            275                 280                 285

Lys Ile Thr Asp Phe Gly Leu Cys Lys Glu Gly Ile Lys Asp Gly Ala
        290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Gly Thr Ala
465                 470                 475                 480

<210> SEQ ID NO 20
<211> LENGTH: 2549
<212> TYPE: PRT
<213> ORGANISM: Homo sapiens

<400> SEQUENCE: 20

Met Leu Gly Thr Gly Pro Ala Ala Ala Thr Thr Ala Ala Thr Thr Ser
1               5                   10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
```

```
                100                 105                 110
Asn Leu Leu Pro Ser Asn Asp Pro Val Val Met Glu Met Ala Ser Lys
            115                 120                 125

Ala Ile Gly Arg Leu Ala Met Ala Gly Asp Thr Phe Thr Ala Glu Tyr
            130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
                180                 185                 190

Asn Ile Phe Val Ala Val Trp Asp Pro Lys Gln Ala Ile Arg Glu Gly
            195                 200                 205

Ala Val Ala Ala Leu Arg Ala Cys Leu Ile Leu Thr Thr Gln Arg Glu
            210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
                260                 265                 270

Arg Ile Ser Ser Met Glu Gly Glu Arg Leu Arg Glu Glu Met Glu Glu
            275                 280                 285

Ile Thr Gln Gln Gln Leu Val His Asp Lys Tyr Cys Lys Asp Leu Met
            290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
                340                 345                 350

Lys Ser Thr Leu Val Glu Ser Arg Cys Cys Arg Asp Leu Met Glu Glu
            355                 360                 365

Lys Phe Asp Gln Val Cys Gln Trp Val Leu Lys Cys Arg Asn Ser Lys
            370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
                420                 425                 430

Ala Phe Gln Ala Leu Gly Leu Leu Ser Val Ala Val Arg Ser Glu Phe
            435                 440                 445

Lys Val Tyr Leu Pro Arg Val Leu Asp Ile Ile Arg Ala Ala Leu Pro
            450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
                500                 505                 510

Leu Ser Pro Ala Leu Thr Ala Val Leu Tyr Asp Leu Ser Arg Gln Ile
            515                 520                 525
```

```
Pro Gln Leu Lys Lys Asp Ile Gln Asp Gly Leu Leu Lys Met Leu Ser
    530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
            565                 570                 575

Ser Asp Val Gly Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
        595                 600                 605

His Phe Leu Asn Ser Glu His Lys Glu Ile Arg Met Glu Ala Ala Arg
    610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Ala Asp Val Leu
            645                 650                 655

Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
            675                 680                 685

Gln Ala Glu Asn Leu Gln Ala Leu Phe Val Ala Leu Asn Asp Gln Val
        690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
            740                 745                 750

Ser Ala Arg Met Leu Gly His Leu Val Ser Asn Ala Pro Arg Leu Ile
            755                 760                 765

Arg Pro Tyr Met Glu Pro Ile Leu Lys Ala Leu Ile Leu Lys Leu Lys
    770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
            805                 810                 815

Val Asp Glu Leu Phe Ile Ile Met Asp Met Leu Gln Asp Ser Ser
            820                 825                 830

Leu Leu Ala Lys Arg Gln Val Ala Leu Trp Thr Leu Gly Gln Leu Val
        835                 840                 845

Ala Ser Thr Gly Tyr Val Val Glu Pro Tyr Arg Lys Tyr Pro Thr Leu
    850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                885                 890                 895

Tyr Lys His Lys Val Asn Ile Gly Met Ile Asp Gln Ser Arg Asp Ala
            900                 905                 910

Ser Ala Val Ser Leu Ser Glu Ser Lys Ser Ser Gln Asp Ser Ser Asp
            915                 920                 925

Tyr Ser Thr Ser Glu Met Leu Val Asn Met Gly Asn Leu Pro Leu Asp
    930                 935                 940
```

-continued

```
Glu Phe Tyr Pro Ala Val Ser Met Val Ala Leu Met Arg Ile Phe Arg
945                 950                 955                 960
Asp Gln Ser Leu Ser His His Thr Met Val Val Gln Ala Ile Thr
                965                 970                 975
Phe Ile Phe Lys Ser Leu Gly Leu Lys Cys Val Gln Phe Leu Pro Gln
            980                 985                 990
Val Met Pro Thr Phe Leu Asn Val Ile Arg Val Cys Asp Gly Ala Ile
        995                 1000                1005
Arg Glu Phe Leu Phe Gln Gln Leu Gly Met Leu Val Ser Phe Val
    1010                1015                1020
Lys Ser His Ile Arg Pro Tyr Met Asp Glu Ile Val Thr Leu Met
    1025                1030                1035
Arg Glu Phe Trp Val Met Asn Thr Ser Ile Gln Ser Thr Ile Ile
    1040                1045                1050
Leu Leu Ile Glu Gln Ile Val Val Ala Leu Gly Gly Glu Phe Lys
    1055                1060                1065
Leu Tyr Leu Pro Gln Leu Ile Pro His Met Leu Arg Val Phe Met
    1070                1075                1080
His Asp Asn Ser Pro Gly Arg Ile Val Ser Ile Lys Leu Leu Ala
    1085                1090                1095
Ala Ile Gln Leu Phe Gly Ala Asn Leu Asp Asp Tyr Leu His Leu
    1100                1105                1110
Leu Leu Pro Pro Ile Val Lys Leu Phe Asp Ala Pro Glu Ala Pro
    1115                1120                1125
Leu Pro Ser Arg Lys Ala Ala Leu Glu Thr Val Asp Arg Leu Thr
    1130                1135                1140
Glu Ser Leu Asp Phe Thr Asp Tyr Ala Ser Arg Ile Ile His Pro
    1145                1150                1155
Ile Val Arg Thr Leu Asp Gln Ser Pro Glu Leu Arg Ser Thr Ala
    1160                1165                1170
Met Asp Thr Leu Ser Ser Leu Val Phe Gln Leu Gly Lys Lys Tyr
    1175                1180                1185
Gln Ile Phe Ile Pro Met Val Asn Lys Val Leu Val Arg His Arg
    1190                1195                1200
Ile Asn His Gln Arg Tyr Asp Val Leu Ile Cys Arg Ile Val Lys
    1205                1210                1215
Gly Tyr Thr Leu Ala Asp Glu Glu Asp Pro Leu Ile Tyr Gln
    1220                1225                1230
His Arg Met Leu Arg Ser Gly Gln Gly Asp Ala Leu Ala Ser Gly
    1235                1240                1245
Pro Val Glu Thr Gly Pro Met Lys Lys Leu His Val Ser Thr Ile
    1250                1255                1260
Asn Leu Gln Lys Ala Trp Gly Ala Ala Arg Arg Val Ser Lys Asp
    1265                1270                1275
Asp Trp Leu Glu Trp Leu Arg Arg Leu Ser Leu Glu Leu Leu Lys
    1280                1285                1290
Asp Ser Ser Ser Pro Ser Leu Arg Ser Cys Trp Ala Leu Ala Gln
    1295                1300                1305
Ala Tyr Asn Pro Met Ala Arg Asp Leu Phe Asn Ala Ala Phe Val
    1310                1315                1320
Ser Cys Trp Ser Glu Leu Asn Glu Asp Gln Gln Asp Glu Leu Ile
    1325                1330                1335
Arg Ser Ile Glu Leu Ala Leu Thr Ser Gln Asp Ile Ala Glu Val
```

```
                    1340                1345                1350

Thr Gln Thr Leu Leu Asn Leu Ala Glu Phe Met Glu His Ser Asp
        1355                1360                1365

Lys Gly Pro Leu Pro Leu Arg Asp Asp Asn Gly Ile Val Leu Leu
        1370                1375                1380

Gly Glu Arg Ala Ala Lys Cys Arg Ala Tyr Ala Lys Ala Leu His
        1385                1390                1395

Tyr Lys Glu Leu Glu Phe Gln Lys Gly Pro Thr Pro Ala Ile Leu
        1400                1405                1410

Glu Ser Leu Ile Ser Ile Asn Asn Lys Leu Gln Gln Pro Glu Ala
        1415                1420                1425

Ala Ala Gly Val Leu Glu Tyr Ala Met Lys His Phe Gly Glu Leu
        1430                1435                1440

Glu Ile Gln Ala Thr Trp Tyr Glu Lys Leu His Glu Trp Glu Asp
        1445                1450                1455

Ala Leu Val Ala Tyr Asp Lys Lys Met Asp Thr Asn Lys Asp Asp
        1460                1465                1470

Pro Glu Leu Met Leu Gly Arg Met Arg Cys Leu Glu Ala Leu Gly
        1475                1480                1485

Glu Trp Gly Gln Leu His Gln Gln Cys Cys Glu Lys Trp Thr Leu
        1490                1495                1500

Val Asn Asp Glu Thr Gln Ala Lys Met Ala Arg Met Ala Ala Ala
        1505                1510                1515

Ala Ala Trp Gly Leu Gly Gln Trp Asp Ser Met Glu Glu Tyr Thr
        1520                1525                1530

Cys Met Ile Pro Arg Asp Thr His Asp Gly Ala Phe Tyr Arg Ala
        1535                1540                1545

Val Leu Ala Leu His Gln Asp Leu Phe Ser Leu Ala Gln Gln Cys
        1550                1555                1560

Ile Asp Lys Ala Arg Asp Leu Leu Asp Ala Glu Leu Thr Ala Met
        1565                1570                1575

Ala Gly Glu Ser Tyr Ser Arg Ala Tyr Gly Ala Met Val Ser Cys
        1580                1585                1590

His Met Leu Ser Glu Leu Glu Glu Val Ile Gln Tyr Lys Leu Val
        1595                1600                1605

Pro Glu Arg Arg Glu Ile Ile Arg Gln Ile Trp Trp Glu Arg Leu
        1610                1615                1620

Gln Gly Cys Gln Arg Ile Val Glu Asp Trp Gln Lys Ile Leu Met
        1625                1630                1635

Val Arg Ser Leu Val Val Ser Pro His Glu Asp Met Arg Thr Trp
        1640                1645                1650

Leu Lys Tyr Ala Ser Leu Cys Gly Lys Ser Gly Arg Leu Ala Leu
        1655                1660                1665

Ala His Lys Thr Leu Val Leu Leu Leu Gly Val Asp Pro Ser Arg
        1670                1675                1680

Gln Leu Asp His Pro Leu Pro Thr Val His Pro Gln Val Thr Tyr
        1685                1690                1695

Ala Tyr Met Lys Asn Met Trp Lys Ser Ala Arg Lys Ile Asp Ala
        1700                1705                1710

Phe Gln His Met Gln His Phe Val Gln Thr Met Gln Gln Gln Ala
        1715                1720                1725

Gln His Ala Ile Ala Thr Glu Asp Gln Gln His Lys Gln Glu Leu
        1730                1735                1740
```

```
His Lys Leu Met Ala Arg Cys Phe Leu Lys Leu Gly Glu Trp Gln
    1745                1750                1755

Leu Asn Leu Gln Gly Ile Asn Glu Ser Thr Ile Pro Lys Val Leu
    1760                1765                1770

Gln Tyr Tyr Ser Ala Ala Thr Glu His Asp Arg Ser Trp Tyr Lys
    1775                1780                1785

Ala Trp His Ala Trp Ala Val Met Asn Phe Glu Ala Val Leu His
    1790                1795                1800

Tyr Lys His Gln Asn Gln Ala Arg Asp Glu Lys Lys Lys Leu Arg
    1805                1810                1815

His Ala Ser Gly Ala Asn Ile Thr Asn Ala Thr Thr Ala Ala Thr
    1820                1825                1830

Thr Ala Ala Thr Ala Thr Thr Thr Ala Ser Thr Glu Gly Ser Asn
    1835                1840                1845

Ser Glu Ser Glu Ala Glu Ser Thr Glu Asn Ser Pro Thr Pro Ser
    1850                1855                1860

Pro Leu Gln Lys Lys Val Thr Glu Asp Leu Ser Lys Thr Leu Leu
    1865                1870                1875

Met Tyr Thr Val Pro Ala Val Gln Gly Phe Phe Arg Ser Ile Ser
    1880                1885                1890

Leu Ser Arg Gly Asn Asn Leu Gln Asp Thr Leu Arg Val Leu Thr
    1895                1900                1905

Leu Trp Phe Asp Tyr Gly His Trp Pro Asp Val Asn Glu Ala Leu
    1910                1915                1920

Val Glu Gly Val Lys Ala Ile Gln Ile Asp Thr Trp Leu Gln Val
    1925                1930                1935

Ile Pro Gln Leu Ile Ala Arg Ile Asp Thr Pro Arg Pro Leu Val
    1940                1945                1950

Gly Arg Leu Ile His Gln Leu Leu Thr Asp Ile Gly Arg Tyr His
    1955                1960                1965

Pro Gln Ala Leu Ile Tyr Pro Leu Thr Val Ala Ser Lys Ser Thr
    1970                1975                1980

Thr Thr Ala Arg His Asn Ala Ala Asn Lys Ile Leu Lys Asn Met
    1985                1990                1995

Cys Glu His Ser Asn Thr Leu Val Gln Gln Ala Met Met Val Ser
    2000                2005                2010

Glu Glu Leu Ile Arg Val Ala Ile Leu Trp His Glu Met Trp His
    2015                2020                2025

Glu Gly Leu Glu Glu Ala Ser Arg Leu Tyr Phe Gly Glu Arg Asn
    2030                2035                2040

Val Lys Gly Met Phe Glu Val Leu Glu Pro Leu His Ala Met Met
    2045                2050                2055

Glu Arg Gly Pro Gln Thr Leu Lys Glu Thr Ser Phe Asn Gln Ala
    2060                2065                2070

Tyr Gly Arg Asp Leu Met Glu Ala Gln Glu Trp Cys Arg Lys Tyr
    2075                2080                2085

Met Lys Ser Gly Asn Val Lys Asp Leu Thr Gln Ala Trp Asp Leu
    2090                2095                2100

Tyr Tyr His Val Phe Arg Arg Ile Ser Lys Gln Leu Pro Gln Leu
    2105                2110                2115

Thr Ser Leu Glu Leu Gln Tyr Val Ser Pro Lys Leu Leu Met Cys
    2120                2125                2130
```

```
Arg Asp Leu Glu Leu Ala Val Pro Gly Thr Tyr Asp Pro Asn Gln
2135                2140                2145

Pro Ile Ile Arg Ile Gln Ser Ile Ala Pro Ser Leu Gln Val Ile
2150                2155                2160

Thr Ser Lys Gln Arg Pro Arg Lys Leu Thr Leu Met Gly Ser Asn
2165                2170                2175

Gly His Glu Phe Val Phe Leu Leu Lys Gly His Glu Asp Leu Arg
2180                2185                2190

Gln Asp Glu Arg Val Met Gln Leu Phe Gly Leu Val Asn Thr Leu
2195                2200                2205

Leu Ala Asn Asp Pro Thr Ser Leu Arg Lys Asn Leu Ser Ile Gln
2210                2215                2220

Arg Tyr Ala Val Ile Pro Leu Ser Thr Asn Ser Gly Leu Ile Gly
2225                2230                2235

Trp Val Pro His Cys Asp Thr Leu His Ala Leu Ile Arg Asp Tyr
2240                2245                2250

Arg Glu Lys Lys Lys Ile Leu Leu Asn Ile Glu His Arg Ile Met
2255                2260                2265

Leu Arg Met Ala Pro Asp Tyr Asp His Leu Thr Leu Met Gln Lys
2270                2275                2280

Val Glu Val Phe Glu His Ala Val Asn Asn Thr Ala Gly Asp Asp
2285                2290                2295

Leu Ala Lys Leu Leu Trp Leu Lys Ser Pro Ser Ser Glu Val Trp
2300                2305                2310

Phe Asp Arg Arg Thr Asn Tyr Thr Arg Ser Leu Ala Val Met Ser
2315                2320                2325

Met Val Gly Tyr Ile Leu Gly Leu Gly Asp Arg His Pro Ser Asn
2330                2335                2340

Leu Met Leu Asp Arg Leu Ser Gly Lys Ile Leu His Ile Asp Phe
2345                2350                2355

Gly Asp Cys Phe Glu Val Ala Met Thr Arg Glu Lys Phe Pro Glu
2360                2365                2370

Lys Ile Pro Phe Arg Leu Thr Arg Met Leu Thr Asn Ala Met Glu
2375                2380                2385

Val Thr Gly Leu Asp Gly Asn Tyr Arg Ile Thr Cys His Thr Val
2390                2395                2400

Met Glu Val Leu Arg Glu His Lys Asp Ser Val Met Ala Val Leu
2405                2410                2415

Glu Ala Phe Val Tyr Asp Pro Leu Leu Asn Trp Arg Leu Met Asp
2420                2425                2430

Thr Asn Thr Lys Gly Asn Lys Arg Ser Arg Thr Arg Thr Asp Ser
2435                2440                2445

Tyr Ser Ala Gly Gln Ser Val Glu Ile Leu Asp Gly Val Glu Leu
2450                2455                2460

Gly Glu Pro Ala His Lys Lys Thr Gly Thr Thr Val Pro Glu Ser
2465                2470                2475

Ile His Ser Phe Ile Gly Asp Gly Leu Val Lys Pro Glu Ala Leu
2480                2485                2490

Asn Lys Lys Ala Ile Gln Ile Ile Asn Arg Val Arg Asp Lys Leu
2495                2500                2505

Thr Gly Arg Asp Phe Ser His Asp Asp Thr Leu Asp Val Pro Thr
2510                2515                2520

Gln Val Glu Leu Leu Ile Lys Gln Ala Thr Ser His Glu Asn Leu
```

```
            2525                2530                 2535
   Cys Gln  Cys Tyr Ile Gly Trp  Cys Pro Phe Trp
       2540                2545

<210> SEQ ID NO 21
<211> LENGTH: 403
<212> TYPE: PRT
<213> ORGANISM: Homo sapiens

<400> SEQUENCE: 21

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350
```

-continued

```
Glu Pro Ser Asn Pro Glu Ala Ser Ser Thr Ser Val Thr Pro Asp
            355                 360                 365
Val Ser Asp Asn Glu Pro Asp His Tyr Arg Tyr Ser Asp Thr Thr Asp
370                 375                 380
Ser Asp Pro Glu Asn Glu Pro Phe Asp Glu Asp Gln His Thr Gln Ile
385                 390                 395                 400
Thr Lys Val
```

<210> SEQ ID NO 22
<211> LENGTH: 393
<212> TYPE: PRT
<213> ORGANISM: Homo sapiens

<400> SEQUENCE: 22

```
Met Pro Lys Lys Pro Thr Pro Ile Gln Leu Asn Pro Ala Pro Asp
1               5                   10                  15
Gly Ser Ala Val Asn Gly Thr Ser Ser Ala Glu Thr Asn Leu Glu Ala
                20                  25                  30
Leu Gln Lys Lys Leu Glu Glu Leu Glu Leu Asp Glu Gln Gln Arg Lys
            35                  40                  45
Arg Leu Glu Ala Phe Leu Thr Gln Lys Gln Lys Val Gly Glu Leu Lys
50                  55                  60
Asp Asp Asp Phe Glu Lys Ile Ser Glu Leu Gly Ala Gly Asn Gly Gly
65                  70                  75                  80
Val Val Phe Lys Val Ser His Lys Pro Ser Gly Leu Val Met Ala Arg
                85                  90                  95
Lys Leu Ile His Leu Glu Ile Lys Pro Ala Ile Arg Asn Gln Ile Ile
                100                 105                 110
Arg Glu Leu Gln Val Leu His Glu Cys Asn Ser Pro Tyr Ile Val Gly
            115                 120                 125
Phe Tyr Gly Ala Phe Tyr Ser Asp Gly Glu Ile Ser Ile Cys Met Glu
130                 135                 140
His Met Asp Gly Gly Ser Leu Asp Gln Val Leu Lys Lys Ala Gly Arg
145                 150                 155                 160
Ile Pro Glu Gln Ile Leu Gly Lys Val Ser Ile Ala Val Ile Lys Gly
                165                 170                 175
Leu Thr Tyr Leu Arg Glu Lys His Lys Ile Met His Arg Asp Val Lys
                180                 185                 190
Pro Ser Asn Ile Leu Val Asn Ser Arg Gly Glu Ile Lys Leu Cys Asp
            195                 200                 205
Phe Gly Val Ser Gly Gln Leu Ile Asp Ser Met Ala Asn Ser Phe Val
210                 215                 220
Gly Thr Arg Ser Tyr Met Ser Pro Glu Arg Leu Gln Gly Thr His Tyr
225                 230                 235                 240
Ser Val Gln Ser Asp Ile Trp Ser Met Gly Leu Ser Leu Val Glu Met
                245                 250                 255
Ala Val Gly Arg Tyr Pro Ile Pro Pro Asp Ala Lys Glu Leu Glu
                260                 265                 270
Leu Met Phe Gly Cys Gln Val Glu Gly Asp Ala Ala Glu Thr Pro Pro
            275                 280                 285
Arg Pro Arg Thr Pro Gly Arg Pro Leu Ser Ser Tyr Gly Met Asp Ser
290                 295                 300
Arg Pro Pro Met Ala Ile Phe Glu Leu Leu Asp Tyr Ile Val Asn Glu
305                 310                 315                 320
```

```
Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
        355                 360                 365

Val Asp Phe Ala Gly Trp Leu Cys Ser Thr Ile Gly Leu Asn Gln Pro
370                 375                 380

Ser Thr Pro Thr His Ala Ala Gly Val
385                 390

<210> SEQ ID NO 23
<211> LENGTH: 360
<212> TYPE: PRT
<213> ORGANISM: Homo sapiens

<400> SEQUENCE: 23

Met Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
            20                  25                  30

Glu Gly Ala Tyr Gly Met Val Cys Ser Ala Tyr Asp Asn Val Asn Lys
        35                  40                  45

Val Arg Val Ala Ile Lys Lys Ile Ser Pro Phe Glu His Gln Thr Tyr
50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Thr Glu Tyr Val Ala Thr Arg Trp
            180                 185                 190

Tyr Arg Ala Pro Glu Ile Met Leu Asn Ser Lys Gly Tyr Thr Lys Ser
        195                 200                 205

Ile Asp Ile Trp Ser Val Gly Cys Ile Leu Ala Glu Met Leu Ser Asn
210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
                245                 250                 255

Asn Leu Lys Ala Arg Asn Tyr Leu Leu Ser Leu Pro His Lys Asn Lys
            260                 265                 270

Val Pro Trp Asn Arg Leu Phe Pro Asn Ala Asp Ser Lys Ala Leu Asp
        275                 280                 285

Leu Leu Asp Lys Met Leu Thr Phe Asn Pro His Lys Arg Ile Glu Val
290                 295                 300
```

```
Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
                325                 330                 335

Asp Leu Pro Lys Glu Lys Leu Lys Glu Leu Ile Phe Glu Thr Ala
            340                 345                 350

Arg Phe Gln Pro Gly Tyr Arg Ser
        355                 360

<210> SEQ ID NO 24
<211> LENGTH: 374
<212> TYPE: PRT
<213> ORGANISM: Homo sapiens

<400> SEQUENCE: 24

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
                20                  25                  30

Val Phe Gln Glu Glu Thr Val Thr Leu His Cys Glu Val Leu His Leu
            35                  40                  45

Pro Gly Ser Ser Ser Thr Gln Trp Phe Leu Asn Gly Thr Ala Thr Gln
        50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
```

```
            305                 310                 315                 320
Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Leu Lys
                340                 345                 350

Cys Gln Glu Gln Lys Glu Gln Leu Gln Glu Gly Val His Arg Lys
                355                 360                 365

Glu Pro Gln Gly Ala Thr
            370

<210> SEQ ID NO 25
<211> LENGTH: 1210
<212> TYPE: PRT
<213> ORGANISM: Homo sapiens

<400> SEQUENCE: 25

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300
```

```
Gly Ser Cys Val Arg Ala Cys Gly Ala Asp Ser Tyr Glu Met Glu Glu
305                 310                 315                 320

Asp Gly Val Arg Lys Cys Lys Cys Glu Gly Pro Cys Arg Lys Val
            325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
            690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
```

-continued

```
            725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
            755                 760                 765
Val Asp Asn Pro His Val Cys Arg Leu Leu Gly Ile Cys Leu Thr Ser
            770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                    805                 810                 815
Trp Cys Val Gln Ile Ala Lys Gly Met Asn Tyr Leu Glu Asp Arg Arg
                    820                 825                 830
Leu Val His Arg Asp Leu Ala Ala Arg Asn Val Leu Val Lys Thr Pro
                    835                 840                 845
Gln His Val Lys Ile Thr Asp Phe Gly Leu Ala Lys Leu Leu Gly Ala
                    850                 855                 860
Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                    885                 890                 895
Val Trp Ser Tyr Gly Val Thr Val Trp Glu Leu Met Thr Phe Gly Ser
                    900                 905                 910
Lys Pro Tyr Asp Gly Ile Pro Ala Ser Glu Ile Ser Ser Ile Leu Glu
                    915                 920                 925
Lys Gly Glu Arg Leu Pro Gln Pro Ile Cys Thr Ile Asp Val Tyr
                    930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                    965                 970                 975
Arg Tyr Leu Val Ile Gln Gly Asp Glu Arg Met His Leu Pro Ser Pro
                    980                 985                 990
Thr Asp Ser Asn Phe Tyr Arg Ala Leu Met Asp Glu Glu Asp Met Asp
                    995                 1000                1005
Asp Val Val Asp Ala Asp Glu Tyr Leu Ile Pro Gln Gln Gly Phe
                    1010                1015                1020
Phe Ser Ser Pro Ser Thr Ser Arg Thr Pro Leu Leu Ser Ser Leu
                    1025                1030                1035
Ser Ala Thr Ser Asn Asn Ser Thr Val Ala Cys Ile Asp Arg Asn
                    1040                1045                1050
Gly Leu Gln Ser Cys Pro Ile Lys Glu Asp Ser Phe Leu Gln Arg
                    1055                1060                1065
Tyr Ser Ser Asp Pro Thr Gly Ala Leu Thr Glu Asp Ser Ile Asp
                    1070                1075                1080
Asp Thr Phe Leu Pro Val Pro Glu Tyr Ile Asn Gln Ser Val Pro
                    1085                1090                1095
Lys Arg Pro Ala Gly Ser Val Gln Asn Pro Val Tyr His Asn Gln
                    1100                1105                1110
Pro Leu Asn Pro Ala Pro Ser Arg Asp Pro His Tyr Gln Asp Pro
                    1115                1120                1125
His Ser Thr Ala Val Gly Asn Pro Glu Tyr Leu Asn Thr Val Gln
                    1130                1135                1140
```

-continued

```
Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 26
<211> LENGTH: 1225
<212> TYPE: PRT
<213> ORGANISM: Homo sapiens

<400> SEQUENCE: 26

Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
                20                  25                  30

Thr Tyr Leu Pro Thr Asn Ala Ser Leu Ser Phe Leu Gln Asp Ile Gln
            35                  40                  45

Glu Val Gln Gly Tyr Val Leu Ile Ala His Asn Gln Val Arg Gln Val
        50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
    130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205

Gln Cys Ala Ala Gly Cys Thr Gly Pro Lys His Ser Asp Cys Leu Ala
    210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
        275                 280                 285

Asn Gln Glu Val Thr Ala Glu Asp Gly Thr Gln Arg Cys Glu Lys Cys
```

```
            290                 295                 300
Ser Lys Pro Cys Ala Arg Val Cys Tyr Gly Leu Gly Met Glu His Leu
305                 310                 315                 320
Arg Glu Val Arg Ala Val Thr Ser Ala Asn Ile Gln Glu Phe Ala Gly
                325                 330                 335
Cys Lys Lys Ile Phe Gly Ser Leu Ala Phe Leu Pro Glu Ser Phe Asp
                340                 345                 350
Gly Asp Pro Ala Ser Asn Thr Ala Pro Leu Gln Pro Glu Gln Leu Gln
                355                 360                 365
Val Phe Glu Thr Leu Glu Glu Ile Thr Gly Tyr Leu Tyr Ile Ser Ala
370                 375                 380
Trp Pro Asp Ser Leu Pro Asp Leu Ser Val Phe Gln Asn Leu Gln Val
385                 390                 395                 400
Ile Arg Gly Arg Ile Leu His Asn Gly Ala Tyr Ser Leu Thr Leu Gln
                405                 410                 415
Gly Leu Gly Ile Ser Trp Leu Gly Leu Arg Ser Leu Arg Glu Leu Gly
                420                 425                 430
Ser Gly Leu Ala Leu Ile His His Asn Thr His Leu Cys Phe Val His
                435                 440                 445
Thr Val Pro Trp Asp Gln Leu Phe Arg Asn Pro His Gln Ala Leu Leu
                450                 455                 460
His Thr Ala Asn Arg Pro Glu Asp Glu Cys Val Gly Glu Gly Leu Ala
465                 470                 475                 480
Cys His Gln Leu Cys Ala Arg Gly His Cys Trp Gly Pro Gly Pro Thr
                485                 490                 495
Gln Cys Val Asn Cys Ser Gln Phe Leu Arg Gly Gln Glu Cys Val Glu
                500                 505                 510
Glu Cys Arg Val Leu Gln Gly Leu Pro Arg Glu Tyr Val Asn Ala Arg
                515                 520                 525
His Cys Leu Pro Cys His Pro Glu Cys Gln Pro Gln Asn Gly Ser Val
                530                 535                 540
Thr Cys Phe Gly Pro Glu Ala Asp Gln Cys Val Ala Cys Ala His Tyr
545                 550                 555                 560
Lys Asp Pro Pro Phe Cys Val Ala Arg Cys Pro Ser Gly Val Lys Pro
                565                 570                 575
Asp Leu Ser Tyr Met Pro Ile Trp Lys Phe Pro Asp Glu Glu Gly Ala
                580                 585                 590
Cys Gln Pro Cys Pro Ile Asn Cys Thr His Ser Cys Val Asp Leu Asp
                595                 600                 605
Asp Lys Gly Cys Pro Ala Glu Gln Arg Ala Ser Pro Leu Thr Ser Ile
                610                 615                 620
Ile Ser Ala Val Val Gly Ile Leu Leu Val Val Leu Gly Val Val
625                 630                 635                 640
Phe Gly Ile Leu Ile Lys Arg Arg Gln Gln Lys Ile Arg Lys Tyr Thr
                645                 650                 655
Met Arg Arg Leu Leu Gln Glu Thr Glu Leu Val Glu Pro Leu Thr Pro
                660                 665                 670
Ser Gly Ala Met Pro Asn Gln Ala Gln Met Arg Ile Leu Lys Glu Thr
                675                 680                 685
Glu Leu Arg Lys Val Lys Val Leu Gly Ser Gly Ala Phe Gly Thr Val
                690                 695                 700
Tyr Lys Gly Ile Trp Ile Pro Asp Gly Glu Asn Val Lys Ile Pro Val
705                 710                 715                 720
```

-continued

```
Ala Ile Lys Val Leu Arg Glu Asn Thr Ser Pro Lys Ala Asn Lys Glu
            725                 730                 735

Ile Leu Asp Glu Ala Tyr Val Met Ala Gly Val Gly Ser Pro Tyr Val
            740                 745                 750

Ser Arg Leu Leu Gly Ile Cys Leu Thr Ser Thr Val Gln Leu Val Thr
            755                 760                 765

Gln Leu Met Pro Tyr Gly Cys Leu Leu Asp His Val Arg Glu Asn Arg
770                 775                 780

Gly Arg Leu Gly Ser Gln Asp Leu Leu Asn Trp Cys Met Gln Ile Ala
785                 790                 795                 800

Lys Gly Met Ser Tyr Leu Glu Asp Val Arg Leu Val His Arg Asp Leu
                805                 810                 815

Ala Ala Arg Asn Val Leu Val Lys Ser Pro Asn His Val Lys Ile Thr
            820                 825                 830

Asp Phe Gly Leu Ala Arg Leu Leu Asp Ile Asp Glu Thr Glu Tyr His
            835                 840                 845

Ala Asp Gly Gly Lys Val Pro Ile Lys Trp Met Ala Leu Glu Ser Ile
850                 855                 860

Leu Arg Arg Arg Phe Thr His Gln Ser Asp Val Trp Ser Tyr Gly Val
865                 870                 875                 880

Thr Val Trp Glu Leu Met Thr Phe Gly Ala Lys Pro Tyr Asp Gly Ile
                885                 890                 895

Pro Ala Arg Glu Ile Pro Asp Leu Leu Glu Lys Gly Glu Arg Leu Pro
            900                 905                 910

Gln Pro Pro Ile Cys Thr Ile Asp Val Tyr Met Ile Met Val Lys Cys
            915                 920                 925

Trp Met Ile Asp Ser Glu Cys Arg Pro Arg Phe Arg Glu Leu Val Ser
930                 935                 940

Glu Phe Ser Arg Met Ala Arg Asp Pro Gln Arg Phe Val Val Ile Gln
945                 950                 955                 960

Asn Glu Asp Leu Gly Pro Ala Ser Pro Leu Asp Ser Thr Phe Tyr Arg
                965                 970                 975

Ser Leu Leu Glu Asp Asp Asp Met Gly Asp Leu Val Asp Ala Glu Glu
            980                 985                 990

Tyr Leu Val Pro Gln Gln Gly Phe Phe Cys Pro Asp Pro Ala Pro Gly
            995                 1000                1005

Ala Gly Gly Met Val His His Arg His Arg Ser Ser Ser Thr Arg
    1010                1015                1020

Ser Gly Gly Gly Asp Leu Thr Leu Gly Leu Glu Pro Ser Glu Glu
    1025                1030                1035

Glu Ala Pro Arg Ser Pro Leu Ala Pro Ser Glu Gly Ala Gly Ser
    1040                1045                1050

Asp Val Phe Asp Gly Asp Leu Gly Met Gly Ala Ala Lys Gly Leu
    1055                1060                1065

Gln Ser Leu Pro Thr His Asp Pro Ser Pro Leu Gln Arg Tyr Ser
    1070                1075                1080

Glu Asp Pro Thr Val Pro Leu Pro Ser Glu Thr Asp Gly Tyr Val
    1085                1090                1095

Ala Pro Leu Thr Cys Ser Pro Gln Pro Glu Tyr Val Asn Gln Pro
    1100                1105                1110

Asp Val Arg Pro Gln Pro Pro Ser Pro Arg Glu Gly Pro Leu Pro
    1115                1120                1125
```

-continued

```
Ala Ala Arg Pro Ala Gly Ala Thr Leu Glu Arg Pro Lys Thr Leu
    1130                1135                1140

Ser Pro Gly Lys Asn Gly Val Val Lys Asp Val Phe Ala Phe Gly
    1145                1150                1155

Gly Ala Val Glu Asn Pro Glu Tyr Leu Thr Pro Gln Gly Gly Ala
    1160                1165                1170

Ala Pro Gln Pro His Pro Pro Ala Phe Ser Pro Ala Phe Asp
    1175                1180                1185

Asn Leu Tyr Tyr Trp Asp Gln Asp Pro Pro Glu Arg Gly Ala Pro
    1190                1195                1200

Pro Ser Thr Phe Lys Gly Thr Pro Thr Ala Glu Asn Pro Glu Tyr
    1205                1210                1215

Leu Gly Leu Asp Val Pro Val
    1220                1225

<210> SEQ ID NO 27
<211> LENGTH: 595
<212> TYPE: PRT
<213> ORGANISM: Homo sapiens

<400> SEQUENCE: 27

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270
```

Asp Gly Glu Gly Arg Gly Glu Val Gly Ser Ala Gly Asp Met Arg Ala
    275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                    325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
                355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                    405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
    435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                    485                 490                 495

Leu Gln Gln Gln His Gln Arg Leu Ala Gln Leu Leu Leu Ile Leu Ser
                500                 505                 510

His Ile Arg His Met Ser Asn Lys Gly Met Glu His Leu Tyr Ser Met
    515                 520                 525

Lys Cys Lys Asn Val Val Pro Leu Tyr Asp Leu Leu Leu Glu Met Leu
530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                    565                 570                 575

His Ser Leu Gln Lys Tyr Tyr Ile Thr Gly Glu Ala Glu Gly Phe Pro
                580                 585                 590

Ala Thr Val
        595

<210> SEQ ID NO 28
<211> LENGTH: 920
<212> TYPE: PRT
<213> ORGANISM: Homo sapiens

<400> SEQUENCE: 28

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
                20                  25                  30

Val Ile Gln Asn Pro Gly Pro Arg His Pro Glu Ala Ala Ser Ala Ala

```
                35                  40                  45
Pro Pro Gly Ala Ser Leu Leu Leu Gln Gln Gln Gln Gln Gln
 50                  55                  60
Gln Gln Gln Gln Gln Gln Gln Gln Gln Gln Gln Gln Gln Gln
 65                  70                  75                  80
Glu Thr Ser Pro Arg Gln Gln Gln Gln Gly Glu Asp Gly Ser
                 85                  90                  95
Pro Gln Ala His Arg Arg Gly Pro Thr Gly Tyr Leu Val Leu Asp Glu
                100                 105                 110
Glu Gln Gln Pro Ser Gln Pro Gln Ser Ala Leu Glu Cys His Pro Glu
                115                 120                 125
Arg Gly Cys Val Pro Glu Pro Gly Ala Ala Val Ala Ala Ser Lys Gly
130                 135                 140
Leu Pro Gln Gln Leu Pro Ala Pro Pro Asp Glu Asp Ser Ala Ala
145                 150                 155                 160
Pro Ser Thr Leu Ser Leu Leu Gly Pro Thr Phe Pro Gly Leu Ser Ser
                165                 170                 175
Cys Ser Ala Asp Leu Lys Asp Ile Leu Ser Glu Ala Ser Thr Met Gln
                180                 185                 190
Leu Leu Gln Gln Gln Gln Gln Glu Ala Val Ser Glu Gly Ser Ser Ser
                195                 200                 205
Gly Arg Ala Arg Glu Ala Ser Gly Ala Pro Thr Ser Ser Lys Asp Asn
210                 215                 220
Tyr Leu Gly Gly Thr Ser Thr Ile Ser Asp Asn Ala Lys Glu Leu Cys
225                 230                 235                 240
Lys Ala Val Ser Val Ser Met Gly Leu Gly Val Glu Ala Leu Glu His
                245                 250                 255
Leu Ser Pro Gly Glu Gln Leu Arg Gly Asp Cys Met Tyr Ala Pro Leu
                260                 265                 270
Leu Gly Val Pro Pro Ala Val Arg Pro Thr Pro Cys Ala Pro Leu Ala
                275                 280                 285
Glu Cys Lys Gly Ser Leu Leu Asp Asp Ser Ala Gly Lys Ser Thr Glu
290                 295                 300
Asp Thr Ala Glu Tyr Ser Pro Phe Lys Gly Gly Tyr Thr Lys Gly Leu
305                 310                 315                 320
Glu Gly Glu Ser Leu Gly Cys Ser Gly Ser Ala Ala Gly Ser Ser
                325                 330                 335
Gly Thr Leu Glu Leu Pro Ser Thr Leu Ser Leu Tyr Lys Ser Gly Ala
                340                 345                 350
Leu Asp Glu Ala Ala Ala Tyr Gln Ser Arg Asp Tyr Tyr Asn Phe Pro
                355                 360                 365
Leu Ala Leu Ala Gly Pro Pro Pro Pro Pro Pro Pro His Pro His
                370                 375                 380
Ala Arg Ile Lys Leu Glu Asn Pro Leu Asp Tyr Gly Ser Ala Trp Ala
385                 390                 395                 400
Ala Ala Ala Ala Gln Cys Arg Tyr Gly Asp Leu Ala Ser Leu His Gly
                405                 410                 415
Ala Gly Ala Ala Gly Pro Gly Ser Gly Ser Pro Ser Ala Ala Ala Ser
                420                 425                 430
Ser Ser Trp His Thr Leu Phe Thr Ala Glu Glu Gly Gln Leu Tyr Gly
                435                 440                 445
Pro Cys Gly Gly Gly Gly Gly Gly Gly Gly Gly Gly Gly Gly
                450                 455                 460
```

```
Gly Gly Gly Gly Gly Gly Gly Gly Glu Ala Gly Val Ala Pro
465                 470                 475                 480

Tyr Gly Tyr Thr Arg Pro Pro Gln Gly Leu Ala Gly Gln Glu Ser Asp
                    485                 490                 495

Phe Thr Ala Pro Asp Val Trp Tyr Pro Gly Gly Met Val Ser Arg Val
            500                 505                 510

Pro Tyr Pro Ser Pro Thr Cys Val Lys Ser Glu Met Gly Pro Trp Met
            515                 520                 525

Asp Ser Tyr Ser Gly Pro Tyr Gly Asp Met Arg Leu Glu Thr Ala Arg
            530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
            595                 600                 605

Arg Lys Asn Cys Pro Ser Cys Arg Leu Arg Lys Cys Tyr Glu Ala Gly
            610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
                645                 650                 655

Thr Gln Lys Leu Thr Val Ser His Ile Glu Gly Tyr Glu Cys Gln Pro
            660                 665                 670

Ile Phe Leu Asn Val Leu Glu Ala Ile Glu Pro Gly Val Val Cys Ala
            675                 680                 685

Gly His Asp Asn Asn Gln Pro Asp Ser Phe Ala Ala Leu Leu Ser Ser
            690                 695                 700

Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala
                725                 730                 735

Val Ile Gln Tyr Ser Trp Met Gly Leu Met Val Phe Ala Met Gly Trp
            740                 745                 750

Arg Ser Phe Thr Asn Val Asn Ser Arg Met Leu Tyr Phe Ala Pro Asp
            755                 760                 765

Leu Val Phe Asn Glu Tyr Arg Met His Lys Ser Arg Met Tyr Ser Gln
            770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
                805                 810                 815

Ile Pro Val Asp Gly Leu Lys Asn Gln Lys Phe Phe Asp Glu Leu Arg
            820                 825                 830

Met Asn Tyr Ile Lys Glu Leu Asp Arg Ile Ile Ala Cys Lys Arg Lys
            835                 840                 845

Asn Pro Thr Ser Cys Ser Arg Arg Phe Tyr Gln Leu Thr Lys Leu Leu
            850                 855                 860

Asp Ser Val Gln Pro Ile Ala Arg Glu Leu His Gln Phe Thr Phe Asp
865                 870                 875                 880
```

```
Leu Leu Ile Lys Ser His Met Val Ser Val Asp Phe Pro Glu Met Met
                885                 890                 895

Ala Glu Ile Ile Ser Val Gln Val Pro Lys Ile Leu Ser Gly Lys Val
            900                 905                 910

Lys Pro Ile Tyr Phe His Thr Gln
        915                 920

<210> SEQ ID NO 29
<211> LENGTH: 403
<212> TYPE: PRT
<213> ORGANISM: Homo sapiens

<400> SEQUENCE: 29

Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Phe Pro
            20                  25                  30

Cys Gln Asn Pro Leu Pro Val Asn Ser Gly Gln Ala Gln Arg Val Leu
        35                  40                  45

Cys Pro Ser Asn Ser Ser Gln Arg Ile Pro Leu Gln Ala Gln Lys Leu
    50                  55                  60

Val Ser Ser His Lys Pro Val Gln Asn Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
            100                 105                 110

Glu Leu Ala Ser Lys Gln Lys Asn Glu Glu Ser Lys Lys Arg Gln Trp
        115                 120                 125

Ala Leu Glu Asp Phe Glu Ile Gly Arg Pro Leu Gly Lys Gly Lys Phe
    130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
        195                 200                 205

Ile Leu Glu Tyr Ala Pro Leu Gly Thr Val Tyr Arg Glu Leu Gln Lys
    210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
            260                 265                 270

Ala Asp Phe Gly Trp Ser Val His Ala Pro Ser Ser Arg Arg Thr Thr
        275                 280                 285

Leu Cys Gly Thr Leu Asp Tyr Leu Pro Pro Glu Met Ile Glu Gly Arg
    290                 295                 300

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335
```

```
Thr Tyr Lys Arg Ile Ser Arg Val Glu Phe Thr Phe Pro Asp Phe Val
            340                 345                 350

Thr Glu Gly Ala Arg Asp Leu Ile Ser Arg Leu Leu Lys His Asn Pro
            355                 360                 365

Ser Gln Arg Pro Met Leu Arg Glu Val Leu His Pro Trp Ile Thr
        370                 375                 380

Ala Asn Ser Ser Lys Pro Ser Asn Cys Gln Asn Lys Glu Ser Ala Ser
385                 390                 395                 400

Lys Gln Ser

<210> SEQ ID NO 30
<211> LENGTH: 300
<212> TYPE: PRT
<213> ORGANISM: Homo sapiens

<400> SEQUENCE: 30

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Thr Leu Pro Ser Lys Ser
    50                  55                  60

Asn Glu Ser His Asp His Met Asp Asp Met Asp Asp Glu Asp Asp Asp
65                  70                  75                  80

Asp His Val Asp Ser Gln Asp Ser Ile Asp Ser Asn Asp Ser Asp Asp
                85                  90                  95

Val Asp Asp Thr Asp Asp Ser His Gln Ser Asp Glu Ser His His Ser
            100                 105                 110

Asp Glu Ser Asp Glu Leu Val Thr Asp Phe Pro Thr Asp Leu Pro Ala
        115                 120                 125

Thr Glu Val Phe Thr Pro Val Val Pro Thr Val Asp Thr Tyr Asp Gly
    130                 135                 140

Arg Gly Asp Ser Val Val Tyr Gly Leu Arg Ser Lys Ser Lys Lys Phe
145                 150                 155                 160

Arg Arg Pro Asp Ile Gln Tyr Pro Asp Ala Thr Asp Glu Asp Ile Thr
                165                 170                 175

Ser His Met Glu Ser Glu Glu Leu Asn Gly Ala Tyr Lys Ala Ile Pro
            180                 185                 190

Val Ala Gln Asp Leu Asn Ala Pro Ser Asp Trp Asp Ser Arg Gly Lys
        195                 200                 205

Asp Ser Tyr Glu Thr Ser Gln Leu Asp Asp Gln Ser Ala Glu Thr His
    210                 215                 220

Ser His Lys Gln Ser Arg Leu Tyr Lys Arg Lys Ala Asn Asp Glu Ser
225                 230                 235                 240

Asn Glu His Ser Asp Val Ile Asp Ser Gln Glu Leu Ser Lys Val Ser
                245                 250                 255

Arg Glu Phe His Ser His Glu Phe His Ser His Glu Asp Met Leu Val
            260                 265                 270

Val Asp Pro Lys Ser Lys Glu Glu Asp Lys His Leu Lys Phe Arg Ile
        275                 280                 285

Ser His Glu Leu Asp Ser Ala Ser Ser Glu Val Asn
    290                 295                 300
```

```
<210> SEQ ID NO 31
<211> LENGTH: 488
<212> TYPE: PRT
<213> ORGANISM: Homo sapiens

<400> SEQUENCE: 31

Met Ala Pro Ala Ala Trp Leu Arg Ser Ala Ala Arg Ala Leu Leu
1               5                   10                  15

Pro Pro Met Leu Leu Leu Leu Gln Pro Pro Leu Leu Ala Arg
            20                  25                  30

Ala Leu Pro Pro Asp Ala His His Leu His Ala Glu Arg Arg Gly Pro
        35                  40                  45

Gln Pro Trp His Ala Ala Leu Pro Ser Ser Pro Ala Pro Ala
50                  55                  60

Thr Gln Glu Ala Pro Arg Pro Ala Ser Ser Leu Arg Pro Pro Arg Cys
65                  70                  75                  80

Gly Val Pro Asp Pro Ser Asp Gly Leu Ser Ala Arg Asn Arg Gln Lys
                85                  90                  95

Arg Phe Val Leu Ser Gly Gly Arg Trp Glu Lys Thr Asp Leu Thr Tyr
                100                 105                 110

Arg Ile Leu Arg Phe Pro Trp Gln Leu Val Gln Glu Val Arg Gln
            115                 120                 125

Thr Met Ala Glu Ala Leu Lys Val Trp Ser Asp Val Thr Pro Leu Thr
130                 135                 140

Phe Thr Glu Val His Glu Gly Arg Ala Asp Ile Met Ile Asp Phe Ala
145                 150                 155                 160

Arg Tyr Trp His Gly Asp Asp Leu Pro Phe Asp Gly Pro Gly Gly Ile
                165                 170                 175

Leu Ala His Ala Phe Phe Pro Lys Thr His Arg Glu Gly Asp Val His
                180                 185                 190

Phe Asp Tyr Asp Glu Thr Trp Thr Ile Gly Asp Asp Gln Gly Thr Asp
            195                 200                 205

Leu Leu Gln Val Ala Ala His Glu Phe Gly His Val Leu Gly Leu Gln
210                 215                 220

His Thr Thr Ala Ala Lys Ala Leu Met Ser Ala Phe Tyr Thr Phe Arg
225                 230                 235                 240

Tyr Pro Leu Ser Leu Ser Pro Asp Asp Cys Arg Gly Val Gln His Leu
                245                 250                 255

Tyr Gly Gln Pro Trp Pro Thr Val Thr Ser Arg Thr Pro Ala Leu Gly
            260                 265                 270

Pro Gln Ala Gly Ile Asp Thr Asn Glu Ile Ala Pro Leu Glu Pro Asp
        275                 280                 285

Ala Pro Pro Asp Ala Cys Glu Ala Ser Phe Asp Ala Val Ser Thr Ile
290                 295                 300

Arg Gly Glu Leu Phe Phe Phe Lys Ala Gly Phe Val Trp Arg Leu Arg
305                 310                 315                 320

Gly Gly Gln Leu Gln Pro Gly Tyr Pro Ala Leu Ala Ser Arg His Trp
                325                 330                 335

Gln Gly Leu Pro Ser Pro Val Asp Ala Ala Phe Glu Asp Ala Gln Gly
            340                 345                 350

His Ile Trp Phe Phe Gln Gly Ala Gln Tyr Trp Val Tyr Asp Gly Glu
        355                 360                 365

Lys Pro Val Leu Gly Pro Ala Pro Leu Thr Glu Leu Gly Leu Val Arg
```

```
                    370                 375                 380

Phe Pro Val His Ala Ala Leu Val Trp Gly Pro Glu Lys Asn Lys Ile
385                 390                 395                 400

Tyr Phe Phe Arg Gly Arg Asp Tyr Trp Arg Phe His Pro Ser Thr Arg
                    405                 410                 415

Arg Val Asp Ser Pro Val Pro Arg Arg Ala Thr Asp Trp Arg Gly Val
                420                 425                 430

Pro Ser Glu Ile Asp Ala Ala Phe Gln Asp Ala Asp Gly Tyr Ala Tyr
            435                 440                 445

Phe Leu Arg Gly Arg Leu Tyr Trp Lys Phe Asp Pro Val Lys Val Lys
        450                 455                 460

Ala Leu Glu Gly Phe Pro Arg Leu Val Gly Pro Asp Phe Phe Gly Cys
465                 470                 475                 480

Ala Glu Pro Ala Asn Thr Phe Leu
                485

<210> SEQ ID NO 32
<211> LENGTH: 432
<212> TYPE: PRT
<213> ORGANISM: Homo sapiens

<400> SEQUENCE: 32

Met Glu Arg Arg Ile Thr Ser Ala Ala Arg Ser Tyr Val Ser
1               5                   10                  15

Ser Gly Glu Met Met Val Gly Gly Leu Ala Pro Gly Arg Arg Leu Gly
                20                  25                  30

Pro Gly Thr Arg Leu Ser Leu Ala Arg Met Pro Pro Pro Leu Pro Thr
            35                  40                  45

Arg Val Asp Phe Ser Leu Ala Gly Ala Leu Asn Ala Gly Phe Lys Glu
        50                  55                  60

Thr Arg Ala Ser Glu Arg Ala Glu Met Met Glu Leu Asn Asp Arg Phe
65                  70                  75                  80

Ala Ser Tyr Ile Glu Lys Val Arg Phe Leu Glu Gln Gln Asn Lys Ala
                85                  90                  95

Leu Ala Ala Glu Leu Asn Gln Leu Arg Ala Lys Glu Pro Thr Lys Leu
                100                 105                 110

Ala Asp Val Tyr Gln Ala Glu Leu Arg Glu Leu Arg Leu Arg Leu Asp
            115                 120                 125

Gln Leu Thr Ala Asn Ser Ala Arg Leu Glu Val Glu Arg Asp Asn Leu
        130                 135                 140

Ala Gln Asp Leu Ala Thr Val Arg Gln Lys Leu Gln Asp Glu Thr Asn
145                 150                 155                 160

Leu Arg Leu Glu Ala Glu Asn Asn Leu Ala Ala Tyr Arg Gln Glu Ala
                165                 170                 175

Asp Glu Ala Thr Leu Ala Arg Leu Asp Leu Glu Arg Lys Ile Glu Ser
            180                 185                 190

Leu Glu Glu Glu Ile Arg Phe Leu Arg Lys Ile His Glu Glu Glu Val
        195                 200                 205

Arg Glu Leu Gln Glu Gln Leu Ala Arg Gln Gln Val His Val Glu Leu
    210                 215                 220

Asp Val Ala Lys Pro Asp Leu Thr Ala Ala Leu Lys Glu Ile Arg Thr
225                 230                 235                 240

Gln Tyr Glu Ala Met Ala Ser Ser Asn Met His Glu Ala Glu Glu Trp
                245                 250                 255
```

-continued

```
Tyr Arg Ser Lys Phe Ala Asp Leu Thr Asp Ala Ala Ala Arg Asn Ala
            260                 265                 270

Glu Leu Leu Arg Gln Ala Lys His Glu Ala Asn Asp Tyr Arg Arg Gln
        275                 280                 285

Leu Gln Ser Leu Thr Cys Asp Leu Glu Ser Leu Arg Gly Thr Asn Glu
    290                 295                 300

Ser Leu Glu Arg Gln Met Arg Glu Gln Glu Glu Arg His Val Arg Glu
305                 310                 315                 320

Ala Ala Ser Tyr Gln Glu Ala Leu Ala Arg Leu Glu Glu Glu Gly Gln
            325                 330                 335

Ser Leu Lys Asp Glu Met Ala Arg His Leu Gln Glu Tyr Gln Asp Leu
            340                 345                 350

Leu Asn Val Lys Leu Ala Leu Asp Ile Glu Ile Ala Thr Tyr Arg Lys
        355                 360                 365

Leu Leu Glu Gly Glu Glu Asn Arg Ile Thr Ile Pro Val Gln Thr Phe
    370                 375                 380

Ser Asn Leu Gln Ile Arg Glu Thr Ser Leu Asp Thr Lys Ser Val Ser
385                 390                 395                 400

Glu Gly His Leu Lys Arg Asn Ile Val Val Lys Thr Val Glu Met Arg
            405                 410                 415

Asp Gly Glu Val Ile Lys Glu Ser Lys Gln Glu His Lys Asp Val Met
            420                 425                 430
```

GENE AND PROTEIN EXPRESSION PROFILES ASSOCIATED WITH THE THERAPEUTIC EFFICACY OF EGFR-TK INHIBITORS

RELATED APPLICATIONS

This application is a Continuation of U.S. application Ser. No. 12/284,397, filed Sep. 22, 2008 which is a Divisional application of Ser. No. 12/072,651 filed Feb. 27, 2008 which claims priority under 35 U.S.C. §119(e) to U.S. Provisional Application Ser. No. 60/903,694 filed Feb. 27, 2007, the entirety of which is incorporated herein by reference.

REFERENCE TO SEQUENCE LISTING

The present application is being filed along with a Sequence Listing in electronic format. The Sequence Listing is provided as a file entitled NUC003USSeqList.txt created on Dec. 22, 2011 which is 178,504 bytes in size. The information in electronic format of the sequence listing is incorporated herein by reference in its entirety.

BACKGROUND OF THE INVENTION

Patients diagnosed with cancer are faced with costly and often painful treatment options. These treatments may be ineffective in a subpopulation of patients, and as a result, these patients endure these treatments without little or no therapeutic benefit. Some patients may react adversely to certain agents causing additional suffering and possibly death.

Ineffective treatment also is problematic because time is a key variable when treating cancer. A treatment provider has a far greater chance of containing and managing the disease if the cancer is diagnosed at an early stage and treated with a therapeutically effective agent. An agent may provide great therapeutic benefits if administered at an early stage of the disease; however, with the passage of time, the same agent may cease to be effective.

Lung cancer is an example of a condition where early diagnosis is key for effective treatment. Most lung cancers fall into one of two categories: small cell lung cancer and non-small cell lung cancer (NSCLC). NSCLC is the most common type of lung cancer. There are three main subgroups of NSCLC: adenocarcinoma, squamous cell carcinoma and large cell undifferentiated carcinoma.

Chemotherapy often is used for treating NSCLC. Erlotinib (TARCEVA®) is a chemotherapeutic agent indicated for second-line therapy of NSCLC after failure of at least one prior chemotherapy regimen and gefitinib (IRESSA®) is indicated for continued treatment of NSCLC after failure of platinum-based and docetaxel chemotherapies. As with many chemotherapeutic agents, administration of these drugs often causes deleterious side effects for the patient, and some patients do not respond well, or respond at all, to the treatment. Some patients thus undergo treatment with erlotinib or gefitinib and suffer the painful side effects only to later realize that the agent has not been therapeutically beneficial to their condition. In addition to the unnecessary suffering, critical time is lost in determining an alternative treatment.

SUMMARY OF THE INVENTION

The present invention provides gene and protein expression profiles and methods for using them to identify those patients who are likely to respond to treatment with compounds that inhibit the intracellular phosphorylation of tyrosine kinase (TK) associated with epidermal growth factor receptor (EGFR), including erlotinib and gefitinib (these patients are referred to as "responders"), as well as those patients who are not likely to benefit from such treatment (these patients are referred to as "non-responders"). The present invention allows a treatment provider to identify those patients who are responders to treatment with compounds that inhibit the intracellular phosphorylation of EGFR-associated tyrosine kinase, including erlotinib and gefitinib, and those who are non-responders to such treatment, prior to administration of the agent. Compounds such as erlotinib and gefitinib that inhibit the intracellular phosphorylation of EGFR-associated tyrosine kinase are referred to hereinafter as EGFR-TK inhibitors.

The present invention comprises protein expression profiles, as well as the corresponding gene expression profiles (also referred to as "gene signatures") that are indicative of the tendency of a patient afflicted with lung cancer, particularly NSCLC, to respond to treatment with an EGFR-TK inhibitor. The protein expression profile comprises at least one, and preferably a plurality, of proteins selected from the group consisting of p70S6K, phospho-p70S6, phospho-S6, phospho-AKT, phospho-mTOR, phospho-pTEN, phospho MEK, phospho MAPK, phospho-IGFR/InR, EGFR, phospho-EGFR, phospho-HER2/ErbB2, phospho-ER, phospho-AR, AIK, osteopontin, MMP11 and GFAP. This group of proteins is referred to herein as the "EGFR-TK Inhibitor Responder Proteins". According to the invention, some or all of these proteins are differentially expressed (e.g., up-regulated or down-regulated) in patients who are responders to EGFR-TK inhibitor therapy. Specifically, p70S6K, phospho-S6, phospho-AKT, phospho-mTOR, phospho-pTEN, EGFR, phospho-ER, phospho-AR, AIK, osteopontin, MMP11 and GFAP are up-regulated (over-expressed) and phospho-p70S6, phospho MEK, phospho MAPK, phospho-IGFR/InR, phospho-EGFR and phospho-HER2/ErbB2 are down-regulated (under expressed) in patients who are responders to EGFR-TK inhibitors.

The present invention further comprises gene expression profiles (also referred to as "gene signatures") that are indicative of the tendency of a patient afflicted with NSCLC to respond to treatment with an EGFR-TK inhibitor. The gene expression profile comprises at least one, and preferably a plurality, of genes that encode the proteins selected from the group consisting of p70S6K, phospho-p70S6, phospho-S6, phospho-AKT, phospho-mTOR, phospho-pTEN, phospho MEK, phospho MAPK, phospho-IGFR/InR, EGFR, phospho-EGFR, phospho-HER2/ErbB2, phospho-ER, phospho-AR, AIK, osteopontin, MMP11 and GFAP. This group of genes is referred to herein as the "EGFR-TK Inhibitor Responder Genes". According to the invention, some or all of theses genes are differentially expressed (e.g., up-regulated or down-regulated) in patients who are responders to EGFR-TK inhibitor therapy. Specifically, the genes encoding p70S6K, phospho-S6, phospho-AKT, phospho-mTOR, phospho-pTEN, EGFR, phospho-ER, phospho-AR, AIK, osteopontin, MMP11 and GFAP are up-regulated (over-expressed) and the genes encoding phospho-p70S6, phospho MEK, phospho MAPK, phospho-IGFR/lnR, phospho-EGFR and phospho-HER2/ErbB2 are down-regulated (under expressed) in patients who are responders to EGFR-TK inhibitors.

The present invention further comprises a method of determining if a patient is a responder or non-responder to treatment with an EGFR-TK inhibitor. The method comprises obtaining a tumor sample from the patient, determining the protein and/or gene expression profile of the sample, and determining from the gene expression profile whether at least one protein selected from the to EGFR-TK inhibitor Responder Proteins and/or the EGFR-TK Inhibitor Responder Genes is over- or under-expressed in the sample. From this information, the treatment provider can ascertain whether the patient is likely to benefit from to EGFR-TK inhibitor therapy.

The present invention further comprises an assay for determining the protein and/or gene expression profile in a patient's sample, and instructions for using the assay.

DETAILED DESCRIPTION

The present invention provides gene and protein expression profiles (GPEPs), and their use for predicting a patient's responsiveness to a cancer treatment. More specifically, the present gene and protein expression profiles are indicative of whether a patient afflicted with non small cell lung cancer (NSCLC) is a responder or a non-responder to treatment with a compound which is an EGFR-TK inhibitor, in particular, erlotinib (TARCEVA®) or gefitinib (IRESSA®).

Erlotinib and gefitinib are chemotherapeutic agents which belong to the group of medicines called antineoplastics. These compounds act by inhibiting the intracellular phoshorylation of tyrosine kinase associated with transmembrane cell surface receptors, including EGFR, a receptor expressed on the cell surface of normal cells and cancer cells. These compounds interfere with the growth of cancer cells, which are eventually destroyed.

Significant improvements in the outcomes of NSCLC in some patients treated with erlotinib or gefitinib have been reported. However, the growth of normal cells often is affected by these medicines, causing unwanted and/or unpleasant effects. These other effects may include: diarrhea, rash, acne, dry skin, nausea (feeling sick) and vomiting, loss of appetite and weight loss, asthenia and pruritis and abdominal pain. The present invention provides biomarkers that are associated with those patients that have benefited from treatment with erlotinib and/or gefitinib. The present invention thus enables the treatment provider to determine in advance those NSCLC patients likely to benefit from treatment with erlotinib or gefitinib, and to consider alternative treatment options for non-responders.

In one embodiment, the present invention provides protein expression profiles that are indicative of whether a patient is likely to be a responder or non-responder to EGFR-TK inhibitor therapy. The proteins comprising the expression profile disclosed herein are selected from the group consisting of p70S6K, phospho-p70S6, phospho-S6, phospho-AKT, phospho-mTOR, phospho-pTEN, phospho MEK, phospho MAPK, phospho-IGFR/InR, EGFR, phospho-EGFR, phospho-HER2/ErbB2, phospho-ER, phospho-AR, AIK, osteopontin, MMP11 and GFAP. This group of proteins is referred to herein as the "EGFR-TK Inhibitor Responder Proteins". According to the invention, some or all of these proteins are differentially expressed (e.g., up-regulated or down-regulated) in patients who are responders to EGFR-TK inhibitor therapy. Specifically, p70S6K, phospho-S6, phospho-AKT, phospho-mTOR, phospho-pTEN, EGFR, phospho-ER, phospho-AR, AIK, osteopontin, MMP11 and GFAP are up-regulated (over-expressed) and phospho-p70S6, phospho MEK, phospho MAPK, phospho-IGFR/lnR, phospho-EGFR and phospho-HER2/ErbB2 are down-regulated (under expressed) in patients who are responders to EGFR-TK inhibitors.

Table 1 identifies the EGFR-TK inhibitor Responder Proteins, and indicates whether expression of these proteins is up- or down-regulated in patients that are responders to therapy with an EGFR-TK inhibitor.

TABLE 1

| Protein* Accession No. | Over Expression | Under Expression | SEQ ID No. of Protein |
|---|---|---|---|
| Total p70S6K NP_003152 | Pos | | 17 |
| Phospho-p70S6 Same as above | | Pos | |
| Phospho-S6 NP_001001 | Pos | | 18 |
| Phospho-AKT NP_005154 | Pos | | 19 |
| Phospho-mTOR NP_004949 | Pos | | 20 |
| Phospho-PTEN NP_000305 | Pos | | 21 |
| Phospho MEK NP_002746 | | Pos | 22 |
| Phospho MAPK NP_002736 | | Pos | 23 |
| Phospho-IGFR1/InR NP_000557 | | Pos | 24 |
| Total EGFR NP_005219 | Pos | | 25 |
| Phospho-EGFR Same as above | | Pos | |
| Phospho-HER2(ErbB2) NP_001005862 | | Pos | 26 |
| Phospho-ER NP_000116 | Pos | | 27 |
| Phospho-AR NP_000035 | Pos | | 28 |
| AIK NP_940835 | Pos | | 29 |
| Osteopontin NP_000573 | Pos | | 30 |
| MMP11 NP_005931 | Pos | | 31 |
| GFAP NP_002046 | Pos | | 32 |

*Accession No. refers to non-phosphorylated protein

The present invention further comprises gene expression profiles that are indicative of the tendency of a patient afflicted with NSCLC to respond to treatment with EGFR-TK inhibitors. The gene expression profile comprises at least one, and preferably a plurality, of genes that encode the proteins selected from the group consisting of p70S6K, phospho-p70S6, phospho-S6, phospho-AKT, phospho-mTOR, phospho-pTEN, phospho MEK, phospho MAPK, phospho-IGFR/InR, EGFR, phospho-EGFR, phospho-HER2/ErbB2, phospho-ER, phospho-AR, AIK, osteopontin, MMP11 and GFAP. This group of proteins is referred to herein as the "EGFR-TK Inhibitor Responder Genes". According to the invention, some or all of theses genes are differentially expressed (e.g., up-regulated or down-regulated) in patients who are responders to EGFR-TK inhibitor therapy. Specifically, the genes encoding p70S6K, phospho-S6, phospho-AKT, phospho-mTOR, phospho-pTEN, EGFR, phospho-ER, phospho-AR, AIK, osteopontin, MMP11 and GFAP are up-regulated (over-expressed) and the genes encoding phospho-p70S6, phospho MEK, phospho MAPK, phospho-IGFR/lnR, phospho-EGFR and phospho-HER2/ErbB2 are down-regulated (under expressed) in patients who are responders to EGFR-TK inhibitors. Accordingly, it is possible to determine in advance if a patient is likely to benefit form such therapy by obtaining a gene expression profile from the patient's tissue, and determining whether one or more of the genes in the EGFR-TK inhibitor Responder Genes is up- or down-regulated.

Table 2 identifies the EGFR-TK Inhibitor Responder Genes and indicates whether expression of these genes is up- or down-regulated in patients that are responders to therapy with an EGFR-TK inhibitor. Table 2 also sets forth the NCBI Accession Number of at least one variant of these genes.

TABLE 2

| Gene Accession Number | Encoded Protein | Over Expression | Under Expression | SEQ ID. No. of Genes |
|---|---|---|---|---|
| RPS6KB1 NM_003161 | Total p70S6K | Pos | | 1 |
| Same as above | Phospho-p70S6 | | Pos | |
| RPS6 NM_001010 | Phospho-S6 | Pos | | 2 |
| AKT1 NM_005163 | Phospho-AKT | Pos | | 3 |
| FRAP1 NM_004958 | Phospho-mTOR | Pos | | 4 |
| PTEN NM_000314 | Phospho-PTEN | Pos | | 5 |
| MAP2K1 NM_002755 | Phospho MEK | | Pos | 6 |
| MAPK1 NM_002745 | Phospho MAPK | | Pos | 7 |
| FCGR1A NM_000566 | Phospho-IGFR1/InR | | Pos | 8 |
| EGFR NM_005228 | Total EGFR | Pos | | 9 |
| Same as above | Phospho-EGFR | | Pos | |
| ERBB2 NM_001005862 | Phospho-HER2(ErbB2) | | Pos | 10 |
| ESR1 NM_000125 | Phospho-ER | Pos | | 11 |
| AR NM_000044 | Phospho-AR | Pos | | 12 |
| AURKA NM_198433 | AIK | Pos | | 13 |
| SPP1 NM_000582 | Osteopontin | Pos | | 14 |
| MMP11 NM_005940 | MMP11 | Pos | | 15 |
| GFAP NM_002055 | GFAP | Pos | | 16 |

Other variants of these genes exist (e.g., see the gene databases available through the NCBI Entrez website (www.ncbi.nlm.nih.gov/gquery), and these variants are encompassed by the present invention.

In a preferred aspect of the present invention, the protein expression profiles of the present invention comprise at least about four, preferably between about four and nine, and more preferably between about nine and eighteen of the EGFR-TK Inhibitor Responder Proteins that are up- or down-regulated as applicable. In a currently preferred embodiment, the protein expression profile comprises at least about four, and preferably about six to twelve, of the EGFR-TK Inhibitor Responder Proteins that are up-regulated, and at least about two, and preferably about four to six, of the EGFR-TK Inhibitor Responder Proteins that are down-regulated.

In a preferred aspect of the present invention, the gene expression profiles of the present invention comprise at least about four, preferably between about four and nine, and more preferably between about nine and sixteen of the EGFR-TK Inhibitor Responder Genes that are up- or down-regulated as applicable. In a currently preferred embodiment, the gene expression profile comprises at least about four, and preferably about six to twelve, of the EGFR-TK Inhibitor Responder Genes that are up-regulated, and at least about two, and preferably about four to six, of the EGFR-TK Inhibitor Responder Genes that are down-regulated.

The protein and/or gene expression profiles of the invention can be used to predict the responsiveness of a NSCLC patient to therapy with an EGFR-TK inhibitor, in particular, erlotinib or gefitinib. In one aspect, the present method comprises (a) obtaining a protein or gene expression profile from a tumor sample of a patient afflicted with NSCLC; (b) determining from the protein or gene expression profile whether expression of one or more of the following proteins is up-regulated (over-expressed): p70S6K, phospho-S6, phospho-AKT, phospho-mTOR, phospho-pTEN, EGFR, phospho-ER, phospho-AR, AIK, osteopontin, MMP11 and GFAP; and/or whether expression of at least one of the following proteins is down-regulated (under-expressed): phospho-p70S6, phospho MEK, phospho MAPK, phospho-IGFR/InR, phoso-EGFR and phospho-HER2(ErbB2). The predictive value of the protein or gene profile for determining response to these compounds increases with the number of these proteins or the associated genes that are found to be up- or down-regulated in accordance with the invention. Preferably, at least about four, more preferably between about four and nine, and most preferably between about nine and eighteen of the EGFR-TK Responder Proteins or Genes are differentially expressed.

Definitions:

For convenience, the meaning of certain terms and phrases employed in the specification, examples, and appended claims are provided below. The definitions are not meant to be limiting in nature and serve to provide a clearer understanding of certain aspects of the present invention.

The term "genome" is intended to include the entire DNA complement of an organism, including the nuclear DNA component, chromosomal or extrachromosomal DNA, as well as the cytoplasmic domain (e.g., mitochondrial DNA).

The term "gene" refers to a nucleic acid sequence that comprises control and coding sequences necessary for producing a polypeptide or precursor. The polypeptide may be encoded by a full length coding sequence or by any portion of the coding sequence. The gene may be derived in whole or in part from any source known to the art, including a plant, a fungus, an animal, a bacterial genome or episome, eukaryotic, nuclear or plasmid DNA, cDNA, viral DNA, or chemically synthesized DNA. A gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. The gene may constitute an uninterrupted coding sequence or it may include one or more introns, bound by the appropriate splice junctions. The Term "gene" as used herein includes variants of the genes identified in Table 1.

The term "gene expression" refers to the process by which a nucleic acid sequence undergoes successful transcription and translation such that detectable levels of the nucleotide sequence are expressed.

The terms "gene expression profile" or "gene signature" refer to a group of genes expressed by a particular cell or tissue type wherein presence of the genes taken together or the differential expression of such genes, is indicative/predictive of a certain condition.

The term "nucleic acid" as used herein, refers to a molecule comprised of one or more nucleotides, i.e., ribonucleotides, deoxyribonucleotides, or both. The term includes monomers and polymers of ribonucleotides and deoxyribonucleotides, with the ribonucleotides and/or deoxyribonucleotides being bound together, in the case of the polymers, via 5' to 3' linkages. The ribonucleotide and deoxyribonucleotide polymers may be single or double-stranded. However, linkages may include any of the linkages known in the art including, for example, nucleic acids comprising 5' to 3' linkages. The nucleotides may be naturally occurring or may be synthetically produced analogs that are capable of forming base-pair relationships with naturally occurring base pairs. Examples of non-naturally occurring bases that are capable of forming base-pairing relationships include, but are not limited to, aza and deaza pyrimidine analogs, aza and deaza purine analogs, and other heterocyclic base analogs, wherein one or more of the carbon and nitrogen atoms of the pyrimidine rings have been substituted by heteroatoms, e.g., oxygen, sulfur, selenium, phosphorus, and the like. Furthermore, the term "nucleic acid sequences" contemplates the complementary sequence and specifically includes any nucleic acid sequence that is substantially homologous to the both the nucleic acid sequence and its complement.

The terms "array" and "microarray" refer to the type of genes or proteins represented on an array by oligonucleotides or protein-capture agents, and where the type of genes or proteins represented on the array is dependent on the intended purpose of the array (e.g., to monitor expression of human genes or proteins). The oligonucleotides or protein-capture agents on a given array may correspond to the same type, category, or group of genes or proteins. Genes or proteins may be considered to be of the same type if they share some common characteristics such as species of origin (e.g., human, mouse, rat); disease state (e.g., cancer); functions (e.g., protein kinases, tumor suppressors); or same biological process (e.g., apoptosis, signal transduction, cell cycle regulation, proliferation, differentiation). For example, one array type may be a "cancer array" in which each of the array oligonucleotides or protein-capture agents correspond to a gene or protein associated with a cancer. An "epithelial array" may be an array of oligonucleotides or protein-capture agents corresponding to unique epithelial genes or proteins. Similarly, a "cell cycle array" may be an array type in which the oligonucleotides or protein-capture agents correspond to unique genes or proteins associated with the cell cycle.

The term "cell type" refers to a cell from a given source (e.g., a tissue, organ) or a cell in a given state of differentiation, or a cell associated with a given pathology or genetic makeup.

The term "activation" as used herein refers to any alteration of a signaling pathway or biological response including, for example, increases above basal levels, restoration to basal levels from an inhibited state, and stimulation of the pathway above basal levels.

The term "differential expression" refers to both quantitative as well as qualitative differences in the temporal and tissue expression patterns of a gene or a protein in diseased tissues or cells versus normal adjacent tissue. For example, a differentially expressed gene may have its expression activated or completely inactivated in normal versus disease conditions, or may be up-regulated (over-expressed) or down-regulated (under-expressed) in a disease condition versus a normal condition. Such a qualitatively regulated gene may exhibit an expression pattern within a given tissue or cell type that is detectable in either control or disease conditions, but is not detectable in both. Stated another way, a gene or protein is differentially expressed when expression of the gene or protein occurs at a higher or lower level in the diseased tissues or cells of a patient relative to the level of its expression in the normal (disease-free) tissues or cells of the patient and/or control tissues or cells.

The term "detectable" refers to an RNA expression pattern which is detectable via the standard techniques of polymerase chain reaction (PCR), reverse transcriptase-(RT) PCR, differential display, and Northern analyses, which are well known to those of skill in the art. Similarly, protein expression patterns may be "detected" via standard techniques such as Western blots.

The term "complementary" refers to the topological compatibility or matching together of the interacting surfaces of a probe molecule and its target. The target and its probe can be described as complementary, and furthermore, the contact surface characteristics are complementary to each other. Hybridization or base pairing between nucleotides or nucleic acids, such as, for example, between the two strands of a double-stranded DNA molecule or between an oligonucleotide probe and a target are complementary.

The term "biological sample" refers to a sample obtained from an organism (e.g., a human patient) or from components (e.g., cells) of an organism. The sample may be of any biological tissue or fluid. The sample may be a "clinical sample" which is a sample derived from a patient. Such samples include, but are not limited to, sputum, blood, blood cells (e.g., white cells), amniotic fluid, plasma, semen, bone marrow, and tissue or fine needle biopsy samples, urine, peritoneal fluid, and pleural fluid, or cells therefrom. Biological samples may also include sections of tissues such as frozen sections taken for histological purposes. A biological sample may also be referred to as a "patient sample."

A "protein" means a polymer of amino acid residues linked together by peptide bonds. The term, as used herein, refers to proteins, polypeptides, and peptides of any size, structure, or function. Typically, however, a protein will be at least six amino acids long. If the protein is a short peptide, it will be at least about 10 amino acid residues long. A protein may be naturally occurring, recombinant, or synthetic, or any combination of these. A protein may also comprise a fragment of a naturally occurring protein or peptide. A protein may be a single molecule or may be a multi-molecular complex. The term protein may also apply to amino acid polymers in which one or more amino acid residues is an artificial chemical analogue of a corresponding naturally occurring amino acid.

A "fragment of a protein," as used herein, refers to a protein that is a portion of another protein. For example, fragments of proteins may comprise polypeptides obtained by digesting full-length protein isolated from cultured cells. In one embodiment, a protein fragment comprises at least about six amino acids. In another embodiment, the fragment comprises at least about ten amino acids. In yet another embodiment, the protein fragment comprises at least about sixteen amino acids.

As used herein, an "expression product" is a biomolecule, such as a protein, which is produced when a gene in an organism is expressed. An expression product may comprise post-translational modifications.

The term "protein expression" refers to the process by which a nucleic acid sequence undergoes successful transcription and translation such that detectable levels of the amino acid sequence or protein are expressed.

The terms "protein expression profile" or "protein expression signature" refer to a group of proteins expressed by a particular cell or tissue type (e.g., neuron, coronary artery endothelium, or disease tissue), wherein presence of the proteins taken together or the differential expression of such proteins, is indicative/predictive of a certain condition.

The term "antibody" means an immunoglobulin, whether natural or partially or wholly synthetically produced. All derivatives thereof that maintain specific binding ability are also included in the term. The term also covers any protein having a binding domain that is homologous or largely homologous to an immunoglobulin binding domain. An antibody may be monoclonal or polyclonal. The antibody may be a member of any immunoglobulin class, including any of the human classes: IgG, IgM, IgA, IgD, and IgE.

The term "antibody fragment" refers to any derivative of an antibody that is less than full-length. In one aspect, the antibody fragment retains at least a significant portion of the full-length antibody's specific binding ability, specifically, as a binding partner. Examples of antibody fragments include, but are not limited to, Fab, Fab', F(ab')$_2$, scFv, Fv, dsFv diabody, and Fd fragments. The antibody fragment may be produced by any means. For example, the antibody fragment may be enzymatic ally or chemically produced by fragmentation of an intact antibody or it may be recombinantly produced from a gene encoding the partial antibody sequence. Alternatively, the antibody fragment may be wholly or partially synthetically produced. The antibody fragment may comprise a single chain antibody fragment. In another embodiment, the fragment may comprise multiple chains that are linked together, for example, by disulfide linkages. The fragment may also comprise a multimolecular complex. A functional antibody fragment may typically comprise at least about 50 amino acids and more typically will comprise at least about 200 amino acids.

Determination of Gene Expression Profiles

The following method was used to identify and validate gene expression profiles indicative of whether the patient will respond to treatment with an EGFR-TK inhibitor. Other methods for identifying gene and/or protein expression profiles are known; any of these alternative methods also could be used. See, e.g., Chen et al., *NEJM*, 356(1):11-20 (2007); Lu et al., *PLOS Med.*, 3(12):e467 (2006); Golub et al., *Science*, 286:531-537 (1999).

The present method utilizes parallel testing in which, in one track, those genes which are over-/under-expressed as compared to normal (non-cancerous) tissue samples are identified, and, in a second track, those genes comprising chromosomal insertions or deletions as compared to normal samples are identified, from the same samples. These two tracks of analysis produce two sets of data. The data are analyzed using an algorithm which identifies the genes of the gene expression profile (i.e., those genes that are differentially expressed in cancer tissue). Positive and negative controls may be employed to normalize the results, including eliminating those genes and proteins that also are differentially expressed in normal tissues from the same patients, and confirming that the gene expression profile is unique to the cancer of interest.

In the present instance, as an initial step, biological samples from about two hundred fifty (250) patients afflicted with NSCLC were acquired. Approximately five-hundred (500) tissue samples obtained from NSCLC cancer patients were used, including tumor tissue and adjacent normal (undiseased) lung tissue. The tissue samples were obtained from patients suffering from various stages of NSCLC cancer. The samples included tumor tissue from patients who had been treated with erlotinib or gefitinib; some of the patients were responders to these compounds and others were non-responders. Clinical information associated with each sample, including treatment with erlotinib or gefitinib and the outcome of the treatment (e.g., length of survival), was recorded in a database. Clinical information also includes information such as age, sex, medical history, treatment history, symptoms, family history, recurrence (yes/no), etc. Control samples, including samples of normal (non-cancerous) lung tissue from the same patients, and other types of cancerous tissue from other patients (e.g., from a tissue repository) also were acquired. Samples of normal undiseased lung tissue from a set of healthy individuals were used as positive controls, and tumor samples from NSCLC patients who were non-responders to with erlotinib or gefitinib therapy were used as negative controls.

Gene expression profiles (GEPs) then were generated from the biological samples based on total RNA according to well-established methods. Briefly, a typical method involves isolating total RNA from the biological sample, amplifying the RNA, synthesizing cDNA, labeling the cDNA with a detectable label, hybridizing the cDNA with a genomic array, such as the Affymetrix U133 GeneChip, and determining binding of the labeled cDNA with the genomic array by measuring the intensity of the signal from the detectable label bound to the array. See, e.g., the methods described in Lu, et al., Chen, et al. and Golub, et al., supra, and the references cited therein, which are incorporated herein by reference. The resulting expression data are input into a database.

MRNAs in the tissue samples can be analyzed using commercially available or customized probes or oligonucleotide arrays, such as cDNA or oligonucleotide arrays. The use of these arrays allows for the measurement of steady-state mRNA levels of thousands of genes simultaneously, thereby presenting a powerful tool for identifying effects such as the onset, arrest or modulation of uncontrolled cell proliferation. Hybridization and/or binding of the probes on the arrays to the nucleic acids of interest from the cells can be determined by detecting and/or measuring the location and intensity of the signal received from the labeled probe or used to detect a DNA/RNA sequence from the sample that hybridizes to a nucleic acid sequence at a known location on the microarray. The intensity of the signal is proportional to the quantity of cDNA or mRNA present in the sample tissue. Numerous arrays and techniques are available and useful. Methods for determining gene and/or protein expression in sample tissues are described, for example, in U.S. Pat. Nos. 6,271,002; 6,218,122; 6,218,114; and U.S. Pat. No. 6,004,755; and in Wang et al., *J. Clin. Oncol.*, 22(9):1564-1671 (2004); Golub et al, (supra); and Schena et al., *Science*, 270:467-470 (1995); all of which are incorporated herein by reference.

The gene analysis aspect utilized in the present method investigates gene expression as well as insertion/deletion data. As a first step, RNA was isolated from the tissue samples and labeled. Parallel processes were run on the sample to develop two sets of data: (1) over-/under-expression of genes based on mRNA levels; and (2) chromosomal insertion/deletion data. These two sets of data were then correlated by means of an algorithm. Over-/under-expression of the genes in each cancer tissue sample were compared to gene expression in the normal (non-cancerous) samples, and a subset of genes that were differentially expressed in the cancer tissue was identified. Preferably, levels of up- and down-regulation are distinguished based on fold changes of the intensity measurements of hybridized microarray probes. A difference of about 2.0 fold or greater is preferred for making such distinctions, or a p-value of less than about 0.05. That is, before a gene is said to be differentially expressed in diseased versus normal cells, the diseased cell is found to yield at least about 2 times greater or less intensity of expression than the normal cells. Generally, the greater the fold difference (or the lower the p-value), the more preferred is the gene for use as a diagnostic or prognostic tool. Genes selected for the gene signatures of the present invention have expression levels that result in the generation of a signal that is distinguishable from those of the normal or non-modulated genes by an amount that exceeds background using clinical laboratory instrumentation.

Statistical values can be used to confidently distinguish modulated from non-modulated genes and noise. Statistical tests can identify the genes most significantly differentially expressed between diverse groups of samples. The Student's t-test is an example of a robust statistical test that can be used to find significant differences between two groups. The lower the p-value, the more compelling the evidence that the gene is showing a difference between the different groups. Nevertheless, since microarrays allow measurement of more than one gene at a time, tens of thousands of statistical tests may be asked at one time. Because of this, it is unlikely to observe small p-values just by chance, and adjustments using a Sidak correction or similar step as well as a randomization/permutation experiment can be made. A p-value less than about 0.05 by the t-test is evidence that the expression level of the gene is significantly different. More compelling evidence is a p-value less then about 0.05 after the Sidak correction is factored in. For a large number of samples in each group, a p-value less than about 0.05 after the randomization/permutation test is the most compelling evidence of a significant difference.

Another parameter that can be used to select genes that generate a signal that is greater than that of the non-modulated gene or noise is the measurement of absolute signal difference. Preferably, the signal generated by the differentially expressed genes differs by at least about 20% from those of the normal or non-modulated gene (on an absolute basis). It is even more preferred that such genes produce expression patterns that are at least about 30% different than those of normal or non-modulated genes.

This differential expression analysis can be performed using commercially available arrays, for example, Affymetrix U133 GeneChip® arrays (Affymetrix, Inc., www.affymetrix.com). These arrays have probe sets for the whole human genome immobilized on the chip, and can be used to determine up- and down-regulation of genes in test samples. Other substrates having affixed thereon human genomic DNA or probes capable of detecting expression products, such as those available from Affymetrix, Agilent Technologies, Inc. (www.agilent.com) or Illumina, Inc. (www.illumina.com), also may be used. Currently preferred gene microarrays for use in the present invention include Affymetrix U133 GeneChip® arrays and Agilent Technologies genomic cDNA microarrays. Instruments and reagents for performing gene expression analysis are commercially available. See, e.g., Affymetrix GeneChip® System (www.affymetrix.com). The expression data obtained from the analysis then is input into the database.

In the second arm of the present method, chromosomal insertion/deletion data for the genes of each sample as compared to samples of normal tissue was obtained. The insertion/deletion analysis was generated using an array-based comparative genomic hybridization ("CGH"). Array CGH measures copy-number variations at multiple loci simultaneously, providing an important tool for studying cancer and developmental disorders and for developing diagnostic and therapeutic targets. Microchips for performing array CGH are commercially available, e.g., from Agilent Technologies. The Agilent chip is a chromosomal array which shows the location of genes on the chromosomes and provides additional data for the gene signature. The insertion/deletion data from this testing is input into the database.

The analyses are carried out on the same samples from the same patients to generate parallel data. The same chips and sample preparation are used to reduce variability.

The expression of certain genes known as "reference genes" "control genes" or "housekeeping genes" also is determined, preferably at the same time, as a means of ensuring the veracity of the expression profile. Reference genes are genes that are consistently expressed in many tissue types, including cancerous and normal tissues, and thus are useful to normalize gene expression profiles. See, e.g., Silvia et al., *BMC Cancer,* 6:200 (2006); Lee et al., *Genome Research,* 12(2):292-297 (2002); Zhang et al., *BMC Mol. Biol.,* 6:4 (2005). Determining the expression of reference genes in parallel with the genes in the unique gene expression profile provides further assurance that the techniques used for determination of the gene expression profile are working properly. Any reference genes can be used in the present method and assay, including, for example, ACTB, GAPD, GUSB, RPLP0 and/or TRFC.

Data Correlation

The differential expression data and the insertion/deletion data in the database are correlated with the clinical outcomes information associated with each tissue sample also in the database by means of an algorithm to determine a gene expression profile for determining therapeutic efficacy of irinotecan, as well as late recurrence of disease and/or disease-related death associated with irinotecan therapy. Various algorithms are available which are useful for correlating the data and identifying the predictive gene signatures. For example, algorithms such as those identified in Xu et al., A Smooth Response Surface Algorithm For Constructing A Gene Regulatory Network, *Physiol. Genomics* 11:11-20 (2002), the entirety of which is incorporated herein by reference, may be used for the practice of the embodiments disclosed herein.

Another method for identifying gene expression profiles is through the use of optimization algorithms such as the mean variance algorithm widely used in establishing stock portfolios. One such method is described in detail in the patent application US Patent Application Publication No. 2003/0194734. Essentially, the method calls for the establishment of a set of inputs expression as measured by intensity) that will optimize the return (signal that is generated) one receives for using it while minimizing the variability of the return. The algorithm described in Irizarry et al., *Nucleic Acids Res.,* 31:e15 (2003) also may be used. The currently preferred algorithm is the JMP Genomics algorithm available from JMP Software (www.jmp.com).

The process of selecting gene expression profiles also may include the application of heuristic rules. Such rules are formulated based on biology and an understanding of the technology used to produce clinical results, and are applied to output from the optimization method. For example, the mean variance method of gene signature identification can be applied to microarray data for a number of genes differentially expressed in subjects with cancer. Output from the method would be an optimized set of genes that could include some genes that are expressed in peripheral blood as well as in diseased tissue. If samples used in the testing method are obtained from peripheral blood and certain genes differentially expressed in instances of cancer could also be differentially expressed in peripheral blood, then a heuristic rule can be applied in which a portfolio is selected from the efficient frontier excluding those that are differentially expressed in peripheral blood. Of course, the rule can be applied prior to the formation of the efficient frontier by, for example, applying the rule during data pre-selection.

Other heuristic rules can be applied that are not necessarily related to the biology in question. For example, one can apply a rule that only a certain percentage of the portfolio can be represented by a particular gene or group of genes. Commercially available software such as the Wagner software readily accommodates these types of heuristics (Wagner Associates Mean-Variance Optimization Application, www.wagner.com). This can be useful, for example, when factors other than accuracy and precision have an impact on the desirability of including one or more genes.

As an example, the algorithm may be used for comparing gene expression profiles for various genes (or portfolios) to ascribe prognoses. The gene expression profiles of each of the genes comprising the portfolio are fixed in a medium such as a computer readable medium. This can take a number of forms. For example, a table can be established into which the range of signals (e.g., intensity measurements) indicative of disease is input. Actual patient data can then be compared to the values in the table to determine whether the patient samples are normal or diseased. In a more sophisticated embodiment, patterns of the expression signals (e.g., fluorescent intensity) are recorded digitally or graphically. The gene expression patterns from the gene portfolios used in conjunction with patient samples are then compared to the expression patterns. Pattern comparison software can then be used to determine whether the patient samples have a pattern indicative of recurrence of the disease. Of course, these comparisons can also be used to determine whether the patient is not likely to experience disease recurrence. The expression profiles of the samples are then compared to the profile of a control cell. If the sample expression patterns are consistent with the expression pattern for recurrence of cancer then (in the absence of countervailing medical considerations) the patient is treated as one would treat a relapse patient. If the sample expression patterns are consistent with the expression pattern from the normal/control cell then the patient is diagnosed negative for the cancer.

A method for analyzing the gene signatures of a patient to determine prognosis of cancer is through the use of a Cox hazard analysis program. The analysis may be conducted using S-Plus software (commercially available from Insightful Corporation, www.insightful.com). Using such methods, a gene expression profile is compared to that of a profile that confidently represents relapse (i.e., expression levels for the combination of genes in the profile is indicative of relapse). The Cox hazard model with the established threshold is used to compare the similarity of the two profiles (known relapse versus patient) and then determines whether the patient profile exceeds the threshold. If it does, then the patient is classified as one who will relapse and is accorded treatment such as adjuvant therapy. If the patient profile does not exceed the threshold then they are classified as a non-relapsing patient. Other analytical tools can also be used to answer the same question such as, linear discriminate analysis, logistic regression and neural network approaches. See, e.g., software available from JMP statistical software (www.jmp.com).

Numerous other well-known methods of pattern recognition are available. The following references provide some examples:

Weighted Voting: Golub, T R., Slonim, D K., Tamaya, P., Huard, C., Gaasenbeek, M., Mesirov, J P., Coller, H., Loh, L., Downing, J R., Caligiuri, M A., Bloomfield, C D., Lander, E S. Molecular classification of cancer: class discovery and class prediction by gene expression monitoring. Science 286: 531-537, 1999.

Support Vector Machines: Su, A I., Welsh, J B., Sapinoso, L M., Kern, S G., Dimitrov, P., Lapp, H., Schultz, P G., Powell, S M., Moskaluk, C A., Frierson, H F. Jr., Hampton, G M. Molecular classification of human carcinomas by use of gene expression signatures. Cancer Research 61:7388-93, 2001. Ramaswamy, S., Tamayo, P., Rifkin, R., Mukherjee, S., Yeang, C H., Angelo, M., Ladd, C., Reich, M., Latulippe, E., Mesirov, J P., Poggio, T., Gerald, W., Loda, M., Lander, E S., Gould, T R. Multiclass cancer diagnosis using tumor gene expression signatures Proceedings of the National Academy of Sciences of the USA 98:15149-15154, 2001.

K-nearest Neighbors: Ramaswamy, S., Tamayo, P., Rifkin, R., Mukherjee, S., Yeang, C H., Angelo, M., Ladd, C., Reich, M., Latulippe, E., Mesirov, J P., Poggio, T., Gerald, W., Loda, M., Lander, E S., Gould, T R. Multiclass cancer diagnosis using tumor gene expression signatures Proceedings of the National Academy of Sciences of the USA 98:15149-15154, 2001.

Correlation Coefficients: van't Veer L J, Dai H, van de Vijver M J, He Y D, Hart A, Mao M, Peterse H L, van der Kooy K, Marton M J, Witteveen A T, Schreiber G J, Kerkhoven R M, Roberts C, Linsley P S, Bernards R, Friend S H. Gene expression profiling predicts clinical outcome of breast cancer, Nature. 2002 Jan. 31;415(6871):530-6.

The gene expression analysis identifies a gene expression profile (GEP) unique to the cancer samples, that is, those genes which are differentially expressed by the cancer cells. This GEP then is validated, for example, using real-time quantitative polymerase chain reaction (RT-qPCR), which may be carried out using commercially available instruments and reagents, such as those available from Applied Biosystems (www.appliedbiosystems.com).

In the present instance, the results of the gene expression analysis showed that in NSCLC cancer patients who were responsive to treatment with an EGFR-TK inhibitor, the genes encoding p70S6K, phospho-S6, phospho-AKT, phospho-mTOR, phospho-pTEN, EGFR, phospho-ER, phospho-AR, AIK, osteopontin, MMP11 and GFAP are up-regulated (over-expressed) and the genes encoding phospho-p70S6, phospho MEK, phospho MAPK, phospho-IGFR/lnR, phospho-EGFR and phospho-HER2/ErbB2 are down-regulated (under expressed) in patients who are responders to EGFR-TK inhibitors, compared with expression of these genes in the normal lung tissue samples from these patients, and from the negative control patients, i.e., the tissue samples from patients that had experienced a recurrence of their cancer after treatment with an EGFR-TK inhibitor. The reference genes used in the present invention, ACTB, GAPD, GUSB, RPLP0 and TRFC, all were up-regulated.

Determination of Protein Expression Profiles

Not all genes expressed by a cell are translated into proteins, therefore, once a GEP has been identified, it is desirable to ascertain whether proteins corresponding to some or all of the differentially expressed genes in the GEP also are differentially expressed by the same cells or tissue. Therefore, protein expression profiles (PEPs) are generated from the same cancer and control tissues used to identify the GEPs. PEPs also are used to validate the GEP in other colon cancer patients.

The preferred method for generating PEPs according to the present invention is by immunohistochemistry (IHC) analysis. In this method antibodies specific for the proteins in the PEP are used to interrogate tissue samples from cancer patients. Other methods for identifying PEPs are known, e.g. in situ hybridization (ISH) using protein-specific nucleic acid probes. See, e.g., Hofer et al., *Clin. Can. Res.,* 11(16):5722 (2005); Volm et al., *Clin. Exp. Metas.,* 19(5):385 (2002). Any of these alternative methods also could be used.

In the present instance, samples of tumor tissue and normal tissue were obtained from patients afflicted with NSCLC who had undergone successful treatment with gefitinib or with 5-FU, docetaxal or cisplatin, these are the same samples used for identifying the GEP. The tissue samples were arrayed on tissue microarrays (TMAs) to enable simultaneous analysis. TMAs consist of substrates, such as glass slides, on which up to about 1000 separate tissue samples are assembled in array fashion to allow simultaneous histological analysis. The tissue samples may comprise tissue obtained from preserved biopsy samples, e.g., paraffin-embedded or frozen tissues. Techniques for making tissue microarrays are well-known in the art. See, e.g., Simon et al., *BioTechniques,* 36(1):98-105 (2004); Kallioniemi et al, WO 99/44062; Kononen et al., *Nat. Med.,* 4:844-847 (1998). In the present instance, a hollow needle was used to remove tissue cores as small as 0.6 mm in diameter from regions of interest in paraffin embedded tissues. The "regions of interest" are those that have been identified by a pathologist as containing the desired diseased or normal tissue. These tissue cores then were inserted in a recipient paraffin block in a precisely spaced array pattern. Sections from this block were cut using a microtome, mounted on a microscope slide and then analyzed by standard histological analysis. Each microarray block can be cut into approximately 100 to approximately 500 sections, which can be subjected to independent tests.

The TMAs were prepared using two tissue samples from each patient: one of NSCLC tumor tissue and one of normal lung tissue. Control arrays also were prepared; in a currently preferred embodiment, the following control TMAs were used: an array containing normal lung tissue samples from healthy, cancer-free individuals; an array of "positive controls" containing tumor tissues from cancer patients afflicted with cancers other than NSCLC, e.g., breast cancer, colon cancer, and prostate cancer; and an array of "negative controls" containing tumor samples from NSCLC cancer patients that had experienced recurrences of the cancer after treatment with an EGFR-TK inhibitor—that is, patients who were "non-responders" to the therapy.

Proteins in the tissue samples may be analyzed by interrogating the TMAs using protein-specific agents, such as antibodies or nucleic acid probes, such as aptamers. Antibodies are preferred for this purpose due to their specificity and availability. The antibodies may be monoclonal or polyclonal antibodies, antibody fragments, and/or various types of synthetic antibodies, including chimeric antibodies, or fragments thereof. Antibodies are commercially available from a number of sources (e.g., Abcam (www.abcam.com), Cell Signaling Technology (www.cellsignal.com), Santa Cruz Biotechnology (www.santacruz.com)), or may be generated using techniques well-known to those skilled in the art. The antibodies typically are equipped with detectable labels, such as enzymes, chromogens or quantum dots, which permit the antibodies to be detected. The antibodies may be conjugated or tagged directly with a detectable label, or indirectly with one member of a binding pair, of which the other member contains a detectable label. Detection systems for use with are described, for example, in the website of Ventana Medical Systems, Inc. (www.ventanamed.com). Quantum dots are particularly useful as detectable labels. The use of quantum dots is described, for example, in the following references: Jaiswal et al., *Nat. Biotechnol.,* 21:47-51 (2003); Chan et al., *Curr. Opin. Biotechnol.,* 13:40-46 (2002); Chan et al., *Science,* 281:435-446 (1998).

The use of antibodies to identify proteins of interest in the cells of a tissue, referred to as immunohistochemistry (IHC), is well established. See, e.g., Simon et al., *BioTechniques,* 36(1):98 (2004); Haedicke et al., *BioTechniques,* 35(1):164 (2003), which are hereby incorporated by reference. The IHC assay can be automated using commercially available instruments, such as the Benchmark instruments available from Ventana Medical Systems, Inc. (www.ventanamed.com).

In the present instance, the TMAs were contacted with antibodies specific for the proteins encoded by the genes identified in the gene expression study as being up- or down-regulated in NSCLC cancer patients who were responders to therapy with an EGFR-Tk inhibitor in order to determine expression of these proteins in each type of tissue. The results of the immunohistochemical assay showed the following:

In NSCLC patients that were responsive to treatment with an EGFR-TK inhibitor, the following proteins were up-regulated: p70S6K, phospho-S6, phospho-AKT, phospho-mTOR, phospho-pTEN, EGFR, phospho-ER, phospho-AR. AIK, osteopontin, MMP11 and GFAP; and the following proteins were down-regulated: phospho-p70S6, phospho-MEK, phospho-MAPK, phospho-IGFR1/InR, phospho-EGFR and phospho-HER2, compared with an expression of these proteins in normal lung tissue from these patients and the normal lung tissue from other patients;

A majority of the EGFR-TK Inhibitor Responder Proteins were not up- or down-regulated in the positive control tissue samples; and The EGFR-TK Inhibitor Responder Proteins were not up- or down-regulated in the negative control tissue, i.e., in the tissue samples from NSCLC patients that had experienced a recurrence of their cancer after treatment with an EGFR-TK inhibitor, specifically gefitinib (IRESSA®).

These results demonstrate that the present protein expression profiles are indicative of therapeutic efficacy of erlotinib or gefitinib in those NSCLC patients having tumors consistent with the expression profile.

Using the techniques described above, protein and gene expression profiles were generated from NSCLC patient samples, and expression profiles unique to patients responsive to therapy with erlotinib or gefitinib were identified. Fifteen proteins identified as being associated with therapeutic efficacy of these compounds are listed in Table 1 above.

Assays

The present invention further comprises methods and assays for determining whether an NSCLC patient is likely to respond to treatment with an EGFR-TK inhibitor, including erlotinib or gefitinib. According to one aspect, a formatted IHC assay can be used for determining if a tumor of an NSCLC patient cancer tumor exhibits the present GPEP. The assays may be formulated into kits that include all or some of the materials needed to conduct the analysis, including reagents (antibodies, detectable labels, etc.) and instructions.

The assay method of the invention comprises contacting a tumor sample from an NSCLC patient with a group of antibodies specific for some or all of the genes or proteins in the present GPEP, and determining the occurrence of up- or down-regulation of these genes or proteins in the samples. The use of TMAs allows numerous samples, including control samples, to be assayed simultaneously.

In a preferred embodiment, the method comprises contacting a tumor sample from an NSCLC patient with a group of antibodies specific for some or all of the proteins in the present GPEP, and determining the occurrence of up- or down-regulation of these proteins. Up-regulation of one or more of the following proteins: p70S6K, phospho-S6, phospho-AKT, phospho-mTOR, phospho-pTEN, EGFR, phospho-ER, phospho-AR, AIK, osteopontin, MMP11 and GFAP; and down-regulation of one or more of the following proteins: phospho-p70S6, phospho-MEK, phospho-MAPK, phospho-IGFR1/InR, phospho-EGFR and phospho-HER2, is indicative of the patient's responsiveness to an EGFR-TK inhibitor, such as erlotinib or gefitinib. Preferably, at least four, preferably between four and nine, and most preferably between nine and eighteen antibodies are used in the present method.

The method preferably also includes detecting and/or quantitating control or "reference proteins". Detecting and/or quantitating the reference proteins in the samples normalizes the results and thus provides further assurance that the assay is working properly. In a currently preferred embodiment, antibodies specific for one or more of the following reference proteins are included: ACTB, GAPD, GUSB, RPLP0 and/or TRFC.

The present invention further comprises a kit containing reagents for conducting an IHC analysis of tissue samples or cells from NSCLC cancer patients, including antibodies specific for at least about four of the proteins in the GPEP and for any reference proteins. The antibodies are preferably tagged with means for detecting the binding of the antibodies to the proteins of interest, e.g., detectable labels. Preferred detectable labels include fluorescent compounds or quantum dots, however other types of detectable labels may be used. Detectable labels for antibodies are commercially available, e.g. from Ventana Medical Systems, Inc. (www.ventanamed.com).

Immunohistochemical methods for detecting protein expression in tissue samples are well known. Any method that permits the determination of expression of several different proteins can be used. See. e.g., Signoretti et al., "Her-2-neu Expression and Progression Toward Androgen Independence in Human Prostate Cancer," *J. Natl. Cancer Instit.*, 92(23): 1918-25 (2000); Gu et al., "Prostate stem cell antigen (PSCA) expression increases with high gleason score, advanced stage and bone metastasis in prostate cancer," *Oncogene,* 19:1288-96 (2000). Such methods can be efficiently carried out using automated instruments designed for immunohistochemical (IHC) analysis. Instruments for rapidly performing such assays are commercially available, e.g., from Ventana Molecular Discovery Systems (www.ventanadiscovery.com) or Lab Vision Corporation (www.labvision.com). Methods according to the present invention using such instruments are carried out according to the manufacturer's instructions.

Protein specific antibodies for use in such methods or assays are readily available or can be prepared using well-established techniques. Antibodies specific for the proteins in the present GPEP can be obtained, for example, from Cell Signaling Technology, Inc. (www.cellsignal.com) or Santa Cruz Biotechnology, Inc. (www.santacruzbiotechnology.com). A comprehensive catalog of commercially available antibodies is available at www.abcam.com.

The present invention is illustrated further by the following non-limiting Example.

EXAMPLE

Clinical Studies

A multicenter clinical trial in the United States evaluated the tumor response rate of gefitinib (IRESSA®) at dosages of 250 and 500 mg/day in patients with advanced non-small cell lung cancer (NSCLC) whose disease had progressed after at least two prior chemotherapy regimens including a platinum drug and docetaxel. IRESSA® was taken once daily at approximately the same time each day.

Two hundred and sixteen patients received IRESSA®; 102 (47%) received a 250 mg dose and 114 (53%) received a 500 mg daily dose. Study patient demographics and disease characteristics are summarized in Table A.

TABLE A

| Scope of study | |
| --- | --- |
| Patient Sample Numbers | Treatment |
| 102 Patients (47%) | 250 mg Iressa |
| 114 Patients (53%) | 500 mg Iressa |
| 142 Patients | Platinum and docetaxel therapies |
| 142 Patients | Positive disease progression |

Forty-one percent of the patients had received two prior treatment regimens, 33% had received three prior treatment regimens, and 25% had received four or more prior treatment regimens. Effectiveness of IRESSA® as third line therapy was determined in the 142 evaluable patients with documented disease progression on platinum and docetaxel therapies or who had had unacceptable toxicity on these agents.

Tissue MicroArrays

Tissue samples obtained from the NSCLC patients in the clinical study were obtained and used to prepare tissue micro arrays (TMAs); other TMAs were prepared as controls. The TMAs used in this study are described in Table B:

TABLE B

| Tissue Micro Arrays | |
| --- | --- |
| Normal Screening Array | This array contained samples of normal (non-cancerous) lung tissue from 200 patients (2 samples per patient) |
| Lung Treatment EGFR | This array contained 500 patient samples obtained from the NSCLC patients who had been treated with IRESSA ®): 250 tumor samples and 250 normal lung tissue samples from the same patients. |
| Cancer screening survey array | Positive control array. This array contained 200 tumor samples for cancers other than lung cancer: 50 breast cancer, 50 colon cancer, 50 prostate cancer and 50 lung cancer. |
| Lung Progression | Negative control array. This array contained samples from the NSCLC patients who progressed to the next stage of lung cancer or experience a recurrence of NSCLC after treatment with gefitinib (IRESSA ®). |

The TMAs were constructed according to the following procedure:

Tissue cores from donor block containing the patient tissue samples were inserted into a recipient paraffin block. These tissue cores are punched with a thin walled, sharpened borer. An X-Y precision guide allowed the orderly placement of these tissue samples in an array format.

Presentation: TMA sections were cut at 4 microns and are mounted on positively charged glass microslides. Individual elements were 0.6 mm in diameter, spaced 0.2 mm apart.

Elements: In addition to TMAs containing the NSCLC samples, screening arrays were produced made up of pancreatic cancers, lymphoma, head and neck cancer, breast cancers and colon cancers tissue samples, 2 each from a different patient. Additional normal tissue samples were included for quality control purposes.

Specificity: The TMAs were designed for use with the specialty staining and immunohistochemical methods described below for gene expression screening purposes, by using monoclonal and polyclonal antibodies over a wide range of characterized tissue types.

Accompanying each array was an array locator map and spreadsheet containing patient diagnostic, histologic and demographic data for each element.

Immunohistochemical Staining

Immunohistochemical staining techniques were used for the visualization of tissue (cell) proteins present in the tissue samples. These techniques were based on the immunoreactivity of antibodies and the chemical properties of enzymes or enzyme complexes, which react with colorless substrate-chromogens to produce a colored end product. Initial immunoenzymatic stains utilized the direct method, which conjugated directly to an antibody with known antigenic specificity (primary antibody).

A modified labeled avidin-biotin technique was employed in which a biotinylated secondary antibody formed a complex with peroxidase-conjugated streptavidin molecules. Endogenous peroxidase activity was quenched by the addition of 3% hydrogen peroxide. The specimens then were incubated with the primary antibodies followed by sequential incubations with the biotinylated secondary link antibody (containing anti-rabbit or anti-mouse immunoglobulins) and peroxidase labeled streptavidin. The primary antibody, secondary antibody, and avidin enzyme complex is then visualized utilizing a substrate-chromogen that produces a brown pigment at the antigen site that is visible by light microscopy. Table C lists the antibodies used in this example.

TABLE C

| Antibody | CST # |
| --- | --- |
| Phospho-p70S6 | CST #9206 |
| Total p70S6 Kinase | CST #9202 |
| Phospho-S6 | CST #2211 |
| Phospho-AKT | CST #3787 |
| Phospho-mTOR | CST #2971 |
| Phospho-pTEN | CST #9554 |
| Phospho MEK | CST #9121 |
| Phospho MAPK | CST #9106 |
| Phospho-IGFR/InR | CST #3021 |
| Total EGFR | CST #2232 |
| Phospho-EGFR | CST #2234 |
| Phospho-HER2(ErbB2) | CST #2241 |
| Phospho-AR | SC #26406-R |
| AIK | CST #4718 |
| Phospho-ER | CST #2511 |

CST refers to Cell Signaling Technology, Inc.
SC refers to Santa Cruz Biotechnology, Inc.

Automated Immunohistochemistry Staining Procedure (IHC):
1. Heat-induced epitope retrieval (HIER) using 10 mM Citrate buffer solution, pH 6.0, was performed as follows:
   a. Deparaffinized and rehydrated sections were placed in a slide staining rack.
   b. The rack was placed in a microwaveable pressure cooker; 750 ml of 10 mM Citrate buffer pH 6.0 was added to cover the slides.
   c. The covered pressure cooker was placed in the microwave on high power for 15 minutes.
   d. The pressure cooker was removed from the microwave and cooled until the pressure indicator dropped and the cover could be safely removed.
   e. The slides were allowed to cool to room temperature, and immunohistochemical staining was carried out.
2. Slides were treated with 3% $H_2O_2$ for 10 min. at RT to quench endogenous peroxidase activity.
3. Slides were rinsed gently with phosphate buffered saline (PBS).
4. The primary antibodies were applied at the predetermined dilution (according to Cell Signaling Technology's Specifications) for 30 min at room temperature. Normal mouse or rabbit serum 1:750 dilution was applied to negative control slides.
5. Slides were rinsed with phosphate buffered saline (PBS).
6. Secondary biotinylated link antibodies* were applied for 30 min at room temperature.
   *Secondary antibody: biotinylated anti-chicken and anti-mouse immunoglobulins in phosphate buffered saline (PBS), containing carrier protein and 15 mM sodium azide.
7. Slides were rinsed with phosphate buffered saline (PBS).
8. The slides were treated with streptavidin-HRP (streptavidin conjugated to horseradish peroxidase)** for 30 min at room temperature.
   **Streptavidin-HRP in PBS containing carrier protein and anti-microbial agents from Ventana,
9. Slides were rinsed with phosphate buffered saline (PBS).
10. The slides were treated with substrate/chromogen*** for 10 min at room temperature.
    ***Substrate-Chromogen is substrate-imidazole-HCl buffer pH 7.5 containing $H_2O_2$ and anti-microbial agents, DAB-3,3'-diaminobenzidine in chromogen solution from Ventana.
11. Slides were raised with distilled water.
12. Counterstain in Hematoxylin was applied for 1 min.
13. Slides were washed in running water for 2 min.
14. The slides were then dehydrated, cleared and the coverglass was mounted Experiment Notes:

All primary antibodies were titrated to dilutions according to manufacturer's specifications. Staining of TE30 Test Array slides (described below) was performed with and without epitope retrieval (HIER). The slides were screened by a pathologist to determine the optimal working dilution. Pretreatment with HIER provided strong specific staining with little to no background. The above immunohistochemical staining was carried out using a Benchmark instrument from Ventana Medical Systems, Inc.

Scoring Criteria:

Staining was scored on a 0-3+ scale, with 0= no staining, and trace (tr) being less than 1+ but greater than 0. The scoring procedures are described in Signoretti et al., J. Nat. Cancer Inst., Vol. 92, No. 23, p. 1918 (December 2000) and Gu et al., Oncogene, 19, 1288-1296 (2000). Grades of 1+ to 3+ represent increased intensity of staining with 3+ being strong, dark brown staining Scoring criteria was also based on total percentage of staining 0=0%, 1=less than 25%, 2=25-50% and 3=greater than 50%. The percent positivity and the intensity of staining for both Nuclear and Cytoplasmic as well as sub-cellular components were analyzed. Both the intensity and percentage positive scores were multiplied to produce one number 0-9. 3+ staining was determined from known expression of the antigen from the positive controls either Breast Adenocarcinoma and/or LNCAP cells.

Positive, Negative and Isotype Matched Controls and Reproducibility:

Positive tissue controls were defined via western blot analysis using the antibodies listed in Table C. This experiment was performed to confirm the level of protein expression in each given control. Negative controls were also defined by the same. The positive controls consisted of Breast, Prostate, Colon and Lung cancer samples.

Positive expression was also confirmed using a Xenograft array. To make this array, SCID mice were injected with tumor cells derived from NSCLC tumors of patients shown to be responsive to gefitinib (IRESSA®), and tumors were allowed to grow. The mice then were injected with 200 mg/kg of IRESSA®, and the mice were monitored to observe responsiveness to the drug.

As a result of treatment with IRESSA®, the tumors formed in the SCID mice were reduced or eliminated. The tumors were found to have the same gene expression profile as that identified in human patients who were responders to gefitinib therapy.

Reproducibility:

All runs were grouped by antibody and tissue arrays which ensured that the runs were normalized, meaning that all of the tissue arrays were stained under the same conditions with the same antibody on the same run. A test array containing thirty negative control samples (TE 30) comprising non-cancerous tissues derived from different (non-lung) organs also was provided. This TE 30 was compared to the previous antibody run and scored accordingly. The reproducibility was compared and validated.

Results:

In tumor samples obtained from those NSCLC patients that were responsive to treatment with an EGFR-TK inhibitor, gefitinib, the following proteins were up-regulated: p70S6K, phospho-S6, phospho-AKT, phospho-mTOR, phospho-pTEN, EGFR, phospho-ER, phospho-AR and AIK; and the following proteins were down-regulated: phospho-p70S6, phospho-MEK, phospho-MAPK, phospho-IGFR1/InR, phospho-EGFR and phospho-HER2, compared with an expression of these proteins in normal lung tissue from these patients and the normal lung tissue from other patients. In contrast, most of these proteins were not up- or down-regulated in the positive control tissue samples. These proteins also were not up- or down-regulated in the negative control tissue, i.e., in the tissue samples from NSCLC patients that had experienced a recurrence of their cancer after treatment with gefitinib. NSCLC patients with tumors exhibiting the present gene and/or protein expression profiles had survived for a longer period of time after treatment with gefitinib compared with NSCLC patients whose tumors did not exhibit the present gene and/or protein expression profiles.

These results show that the present protein expression profile is indicative of therapeutic efficacy of erlotinib or gefitinib in those NSCLC patients having tumors consistent with the expression profile. These data support a potential role for this signature as a determinant of EGFR activity in NSCLC tumor cells and expression as a novel biomarkers for predicting clinical activity of the EGFR inhibitors erlotinib and gefitinib in NSCLC patients.

What is claimed is:

1. A method of determining if a patient diagnosed with non-small cell lung cancer (NSCLC) is a responder to treatment with gefitinib comprising:
   a. obtaining lung cancer tissue from the patient diagnosed with non-small cell lung cancer;
   b. determining the levels of expression in the lung cancer tissue or lung cancer cells of the four proteins: p70S6K comprising the amino acid sequence of SEQ ID NO. 17, phospho-S6 comprising the amino acid sequence of SEQ ID NO. 18, phospho-mTOR comprising the amino acid sequence of SEQ ID NO. 20, and EGFR comprising the amino acid sequence of SEQ ID NO. 25; and
   c. determining that the patient is a responder to treatment with an EGFR-TK inhibitor if the levels of expression of p70S6K, phospho-S6, phospho-mTOR and EGFR are elevated in the lung cancer tissue or lung cancer cells as compared to the corresponding levels in normal lung tissue or normal lung cells.

2. The method of claim 1, further comprising determining the level of expression of at least one reference protein in said lung cancer tissue or lung cancer cells and in said normal lung tissue or normal lung cells.

3. The method of claim 1, wherein step (b) is performed using immunohistochemistry.

4. The method of claim 2, wherein the reference protein is selected from the group consisting of: ACTB, GAPD, GUSB, RPL0 and TRFC.

5. The method of claim 1, wherein at least four of the proteins selected from the group consisting of p70S6K, phospho-S6, phospho-AKT, phospho-mTOR, phospho-pTEN, EGFR, phospho-ER, phospho-AR, AIK, osteopontin, and MMP11 are elevated in the lung cancer tissue or lung cancer cells.

6. The method of claim 5, wherein the at least four proteins are p70S6K, phospho-S6, phospho-mTOR and EGFR.

7. The method of claim 1, wherein between four and nine of the proteins selected from the group consisting of p70S6K, phospho-S6, phospho-AKT, phospho-mTOR, phospho-pTEN, EGFR, phospho-ER, phospho-AR, AIK, osteopontin, and MMP11 are elevated in the lung cancer tissue or lung cancer cells as compared to the corresponding levels in normal lung tissue or normal lung cells.

8. The method of claim 7, wherein the elevated proteins consist of p70S6K, phospho-S6, phospho-mTOR, and EGFR.

9. The method of claim 5, further comprising determining that the patient is a responder to treatment with an EGFR-TK inhibitor if the levels of one or more of the proteins selected from the group consisting of phospho-MEK comprising the amino acid sequence of SEQ ID NO. 22, phospho-MAPK comprising the amino acid sequence of SEQ ID NO. 23, phospho-IGFR/InR comprising the amino acid sequence of SEQ ID NO. 24, and phospho-HER2 (ErbB2) comprising the amino acid sequence of SEQ ID NO. 26, are lower in the lung cancer tissue or lung cancer cells as compared to the corresponding levels in normal lung tissue or normal lung cells.

10. The method of claim 3, wherein the immunohistochemistry includes the use of antibodies having a detectable label.

11. The method of claim 10, wherein the antibodies are monoclonal.

12. The method of claim 10, wherein the detectable label is selected from the group consisting of enzymes, chromogens, fluorescent compounds and quantum dots.

13. The method of claim 1, wherein the patient diagnosed with non-small cell lung cancer (NSCLC) has previously undergone one or more chemotherapy regimens.

14. The method of claim 13, wherein said one or more chemotherapy regimens includes treatment with either or both a platinum drug or docetalex.

* * * * *